(12) United States Patent
Collins et al.

(10) Patent No.: US 6,498,174 B1
(45) Date of Patent: Dec. 24, 2002

(54) SUBSTITUTED OXAZOLES AND THIAZOLES DERIVATIVES AS HPPARγ AND HPPARα ACTIVATORS

(75) Inventors: Jon Loren Collins, Durham, NC (US); Milana Dezube, Chapel, NC (US); Jeffrey Alan Oplinger, Apex, NC (US); Timothy Mark Willson, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/762,445
(22) PCT Filed: Aug. 5, 1999
(86) PCT No.: PCT/EP99/05666
§ 371 (c)(1),
(2), (4) Date: Feb. 22, 2001
(87) PCT Pub. No.: WO00/08002
PCT Pub. Date: Feb. 17, 2000

(30) Foreign Application Priority Data

Aug. 7, 1998 (GB) .............................................. 9817118

(51) Int. Cl.$^7$ .................... C07D 263/32; C07D 263/38; C07D 277/22; A61K 31/427; A61K 31/422
(52) U.S. Cl. .................. 514/365; 514/374; 514/376; 514/369; 514/370; 548/187; 548/194; 548/204; 548/233; 548/235; 546/269.7; 546/27.1; 544/405
(58) Field of Search .................................. 548/187, 194, 548/204, 233, 235; 514/374, 376, 365, 369, 370; 546/269.7, 27.1; 544/405

(56) References Cited

FOREIGN PATENT DOCUMENTS

| EP | 0930229 A1 | 7/1999 |
|---|---|---|
| WO | WO91 19702 A | 12/1991 |
| WO | WO96 38415 A | 12/1996 |
| WO | WO97 31907 A | 9/1997 |

*Primary Examiner*—Mukund J. Shah
*Assistant Examiner*—Kahsay Habte
(74) *Attorney, Agent, or Firm*—Robert H. Brink

(57) ABSTRACT

The present invention discloses compounds of formula (I), and tautomeric forms, pharmaceutically acceptable salts, or solvates thereof. Preferably, the compounds of the invention are dual activators of hPPARγ and hPPARά.

14 Claims, No Drawings

SUBSTITUTED OXAZOLES AND THIAZOLES DERIVATIVES AS HPPARγ AND HPPARα ACTIVATORS

This application is filed pursuant to 35 U.S.C. §371 as a United States National Phase Application of International Application No. PCT/EP99/05666 filed Aug. 5, 1999, which claims priority from 9817118.4 filed Aug. 7, 1998.

The present invention relates to certain novel compounds, to processes for their preparation, to pharmaceutical compositions containing them and to their use in medicine. More particularly, it relates to compounds which exhibit activation, including dual agonist activity, to peroxisome proliferator-activated receptors gamma (PPARγ) and alpha (PPARα) thereby enabling them to modulate the blood glucose and lipid levels in mammals.

Treatment of type 2 diabetes mellitus usually begins with a combination of diet and exercise, with progression to oral hypoglycaemics (e.g. sulfonylureas) and in more severe cases, insulin. In the last decade a class of compounds known as thiazolidinediones (e.g. U.S. Pat. Nos. 5,089,514, 4,342,771, 4,367,234, 4,340,605, 5,306,726) have emerged as effective antidiabetic agents that enhance the insulin sensitivity of target tissues (skeletal muscle, liver, adipose) in animal models of type 2 diabetes mellitus and also reduce lipid and insulin levels in these animal models.

It has been reported that thiazolidinediones are potent and selective activators of PPARγ and bind directly to the PPARγ receptor (J. M. Lehmann et. al., *J. Biol. Chem.* 12953–12956, 270 (1995)), providing evidence that PPARγ is a possible target for the therapeutic actions of the thiazolidinediones.

PCT patent publication WO 97/31907 discloses certain novel compounds that bind to and activate PPARγ. These compounds are indicated to be useful for the treatment of type 2 diabetes mellitus and other diseases.

Activators of the nuclear receptor PPARγ, for example troglitazone, have been shown in the clinic to enhance insulin-action, reduce serum glucose and have small but significant effects on reducing serum triglyceride levels in patients with Type 2 diabetes. See, for example, D. E. Kelly et al., *Curr. Opin. Endocrinol. Diabetes*, 90–96, 5 (2), (1998); M. D. Johnson et al., *Ann. Pharmacother.*, 337–348, 32 (3), (1997); and M. Leutenegger et al., *Curr. Ther. Res.*, 403–416, 58 (7), (1997).

The mechanism for this triglyceride lowering effect appears to be predominantly increased clearance of very low density lipoproteins (VLDL) through induction of liporotein lipase (LPL) gene expression. See, for. example, B. Staels et al., *Arterioscler. Thromb., Vasc. Biol.*, 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., *Curr. Pharm. Des.*, 1–14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., *Atherosclerosis*, (Shannon, Irel.), S29–S37, 124 (Suppl), (1996).

In addition, a dual agonist of PPARα and PPARγ could be effective in reducing the dyslipidemia and hyperinsulinemia associated with impaired glucose tolerance (IGT) or metabolic syndrome and could be effective in patients with mixed hyperlipidemia. See, for example, U.S. Pat. Nos. 5,478,852.

PCT patent publication WO 98/05331 (Paterniti et al.) relates to methods for treating diabetes and cardiovascular disease using a PPARγ agonist in combination with a PPARα agonist, or a compound that activates both PPARγ and PPARα.

BRIEF DESCRIPTION

Briefly, in one aspect, the present invention provides compounds of formula (I), and tautomeric forms, pharmaceutically acceptable salts and solvates thereof,

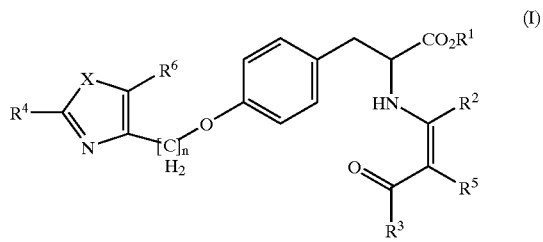

wherein;

$R^1$ is hydrogen or $C_{1-3}$alkyl;

$R^2$ is hydrogen, or $C_{1-8}$alkyl optionally substituted by one or more halogens;

$R^3$ is $C_{1-6}$alkyl, $C_{4-7}$cycloalkyl or cycloalkenyl, —$OC_{1-6}$alkyl, —NR'R' (where each R' is independently hydrogen or $C_{1-3}$alkyl), a 5 or 6 membered heterocyclic group containing at least one oxygen, nitrogen, or sulfur ring atom (optionally substituted by one or more halogen, $C_{1-6}$alkyl optionally substituted by one or more halogens, —$OC_{1-6}$alkyl optionally substituted by one or more halogens, —CN, or —$NO_2$), or phenyl (optionally substituted by one or more halogen, $C_{1-6}$alkyl optionally substituted by one or more halogens, —$OC_{1-6}$alkyl optionally substituted by one or more halogens, —CN, or —$NO_2$);

$R^4$ is a 5 or 6 membered heterocyclic group containing at least one oxygen, nitrogen, or sulfur ring atom (optionally substituted by one or more halogen, $C_{1-6}$alkyl optionally substituted by one or more halogens, —$OC_{1-6}$alkyl optionally substituted by one or more halogens, —CN, or —$NO_2$), or phenyl (optionally substituted by one or more halogen, $C_{1-6}$alkyl optionally substituted by one or more halogens, —$OC_{1-6}$alkyl optionally substituted by one or more halogens, —NR'R' (as defined above), —CN, or —$NO_2$);

$R^5$ is hydrogen, halogen, or $C_{1-3}$alkyl optionally substituted by one or more halogens;

$R^6$ is hydrogen or $C_{1-3}$alkyl;

X is O or S; and n is 1, 2, or 3.

Preferably, the compounds of this invention activate both the hPPARγ and hPPARα receptors.

In another aspect, the present invention provides pharmaceutical compositions comprising a compound of the invention. As used herein, "a compound of the invention" means a compound of formula (I) or a tautomeric form, pharmaceutically acceptable salt, or solvates thereof.

The invention further provides a compound of the invention for use in therapy, and in particular, in human medicine.

In another aspect, the present invention provides a method for treatment or prevention of a hPPARγ and/or hPPARα mediated disease, risk factor, or condition, comprising administration of a therapeutically effective amount of a compound of this invention.

According to another aspect, the present invention provides the use of a compound of the invention for the manufacture of a medicament for the is treatment or prevention of a hPPARγ and/or hPPARα mediated disease.

hPPARγ and/or hPPARα mediated diseases, risk factors, or conditions include hyperglycemia, dyslipidemia, type II diabetes mellitus including associated diabetic dyslipidemia, type I diabetes, hypertriglyceridemia, syndrome X, insulin resistance, heart failure, hyperlipidemia, hypercholesteremia, hypertension, cardiovascular disease, including atherosclerosis, regulation of appetite and food intake in subjects suffering from disorders such as obesity, anorexia bulimia, and anorexia nervosa. In particular, the compounds of the present invention are useful in the treatment or prevention of hyperglycaemia, dyslipidemia, and type II diabetes mellitus including associated diabetic dyslipidemia.

DETAILED DESCRIPTION

Preferably, $R^1$ is hydrogen or methyl. Most preferably, $R^1$ is hydrogen.

Preferably, $R^2$ is $C_{1-8}$alkyl optionally substituted by one or more halogens. Preferably, said halogen is fluorine. Most preferably, $R^2$ is straight-chain.

Preferably, $R^3$ is pyridine, pyrazine, thiophene, furan, thiazole, or phenyl (any of which may be optionally substituted by one or more halogen, $C_{1-6}$alkyl optionally substituted by one or more halogens, $-OC_{1-6}$alkyl optionally substituted by one or more halogens, $-CN$, or $-NO_2$), or $C_{4-7}$cycloalkyl. Most preferably, $R^3$ is phenyl (optionally substituted by one or more halogen, $C_{1-6}$alkyl optionally substituted by one or more halogens, $-OC_{1-6}$alkyl optionally substituted by one or more halogens, $-CN$, or $-NO_2$).

Preferably $R^4$ is phenyl (optionally substituted by one or more halogen, $C_{1-6}$alkyl optionally substituted by one or more halogens, or $-OC_{1-6}$alkyl optionally substituted by one or more halogens). Preferably, said halogen is fluorine. Most preferably $R^4$ is phenyl either unsubstituted or substituted with 1, 2, or 3 fluorine atoms.

Preferably, $R^5$ is hydrogen, halogen, or $C_{1-3}$alkyl optionally substituted by one or more halogens. Most preferably $R^5$ is hydrogen.

Preferably $R^6$ is methyl or ethyl.

Preferably n is 2.

Preferably, the carbon atom bonded to $CO_2R^1$ is in the S configuration. In other words, preferably, the absolute configuration around that carbon is:

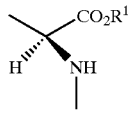

Suitable compounds of the present invention include:
(2S)-2-{[(Z)-1-methyl-3-oxo-3-phenyl-1-propenyl]amino}-3-{4-[2-(5-methyl-2-phenyl-1,3-oxazol-4-yl)ethoxy]phenyl}propanoic acid
(2S)-3-(4-{2-[2-(4-fluorophenyl)-5-methyl-1,3-oxazol-4-yl]ethoxy}phenyl)-2-({(Z)-1-methyl-3-oxo-3-[4-(trifluoromethyl)phenyl]-1-propenyl}amino)propanoic acid
(2S)-3-(4-{2-[2-(4-isopropoxyphenyl)-5-methyl-1,3-oxazol-4-yl]ethoxy}phenyl)-2-({(Z)-1-methyl-3-oxo-3-[4-(trifluoromethyl)phenyl]-1-propenyl}amino)propanoic acid
(2S)-3-(4-{2-[2-(4-methoxyphenyl)-5-methyl-1,3-oxazol-4-yl]ethoxy}phenyl)-2-({(Z)-1-methyl-3-oxo-3-[4-(trifluoromethyl)phenyl]-1-propenyl}amino)propanoic acid
(2S)-2-{[(Z)-1-ethyl-3-oxo-3-phenyl-1-propenyl]amino}-3-[4-(2-{5-methyl-2-[4 -(trifluoromethyl)phenyl]-1,3-oxazol-4-yl}ethoxy)phenyl]propanoic acid
(2S)-2-{[(Z)-1-ethyl-3-(4-fluorophenyl)-3-oxo-1-propenyl]amino}-3-(4-{2-[2-(4-methoxyphenyl)-5-methyl-1,3-oxazol-4-yl]ethoxy}phenyl)propanoic acid
(2S)-2-{[(Z)-1-methyl-3-oxo-3-phenyl-1-propenyl]amino}-3-[4-(2-{5-methyl-2-[4-(trifluoromethyl)phenyl]-1,3-oxazol-4-yl}ethoxy)phenyl]propanoic acid
(2S)-2-{[(Z)-1-ethyl-3-oxo-3-phenyl-1-propenyl]amino}-3-(4-{2-[2-(4-fluorophenyl)-5-methyl-1,3-oxazol-4-yl]ethoxy}phenyl)propanoic acid
(2S)-2-{[(Z)-1-ethyl-3-(4-fluorophenyl)-3-oxo-1-propenyl]amino}-3-(4-{2-[2-(4-fluorophenyl)-5-methyl-1,3-oxazol-4-yl]ethoxy}phenyl)propanoic acid
(2S)-2-({(Z)-1-methyl-3-oxo-3-[4-(trifluoromethyl)phenyl]-1-propenyl}amino)-3-{4-[2-(5-methyl-2-phenyl-1,3-thiazol-4-yl)ethoxy]phenyl}propanoic acid
(2S)-2-{[(Z)-3-(4-fluorophenyl)-1-methyl-3-oxo-1-propenyl]amino}-3-{4-[2-(5-methyl-2-phenyl-1,3-oxazol-4-yl)ethoxy]phenyl}propanoic acid
(2S)-2-{[(Z)-1-methyl-3-oxo-3-(2,3,4-trifluorophenyl)-1-propenyl]amino}-3-{4-[2-(5methyl-2-phenyl-1,3-oxazol-4-yl)ethoxy]phenyl}propanoic acid
(2S)-2-{[(Z)-1-methyl-3-(4-nitrophenyl)-3-oxo-1-propenyl]amino}-3-{4-[2-(5-methyl-2-phenyl-1,3-oxazol-4-yl)ethoxy]phenyl}propanoic acid
(2S)-2-({(Z)-1-methyl-3-oxo-3-[4-(trifluoromethyl)phenyl]-1-propenyl}amino)-3-{4-[2-(5-methyl-2-phenyl-1,3-oxazol-4-yl)ethoxy]phenyl}propanoic acid
(2S)-2-{[(Z)-1-ethyl-3-(4-fluorophenyl)-3-oxo-1-propenyl]amino}-3-(4-{2-[2-(4-isopropoxyphenyl)-5-methyl-1,3-oxazol-4-yl]ethoxy}phenyl)propanoic acid
(2S)-2-{[(Z)-1-methyl-3-oxo-3-(2,4,5-trifluorophenyl)-1-propenyl]amino}-3-{4-[2-(5-methyl-2-phenyl-1,3-oxazol-4-yl)ethoxy]phenyl}propanoic acid
(2S)-2-{[(Z)-1-ethyl-3-oxo-3-phenyl-1-propenyl]amino}-3-(4-{2-[2-(4-isopropoxyphenyl)-5-methyl-1,3-oxazol-4-yl]ethoxy}phenyl)propanoic acid
(2S)-2-{(Z)-1-ethyl-3-oxo-3-[4-(trifluoromethyl)phenyl]-1-propenyl}amino)-3-{4-([2-(5-methyl-2-phenyl-1,3-oxazol-4-yl)ethoxy]phenyl}propanoic acid
(2S)-2-{[(Z)-1-methyl-3-(4-methylphenyl)-3-oxo-1-propenyl]amino}-3-{4-[2-(5-methyl-2-phenyl-1,3-oxazol-4-yl)ethoxy]phenyl}propanoic acid
(2S)-2-{[(Z)-1-ethyl-3-oxo-3-phenyl-1-propenyl]amino}-3-{4-[2-(5-methyl-2-phenyl-1,3-oxazol-4-yl)ethoxy]phenyl}propanoic acid
(2S)-3-(4-{2-[2-(4-fluorophenyl)-5-methyl-1,3-thiazol-4-yl]ethoxy}phenyl)-2-({[(Z)-3-oxo-3-phenyl-1-(trifluoromethyl)-1-propenyl]amino}propanoic acid
(2S)-2-({(Z)-1-ethyl-3-oxo-3-[4-(trifluoromethyl)phenyl]-1-propenyl}amino)-3-(4-{2-[2-(4-fluorophenyl)-5-methyl-1,3-thiazol-4-yl]ethoxy}phenyl)propanoic acid
(2S)-2-{[(Z)-1-butyl-3-oxo-3-phenyl-1-propenyl]amino}-3-{4-[2-(5methyl-2-phenyl-1,3-oxazol-4-yl)ethoxy]phenyl}propanoic acid
(2S)-2-{[(Z)-3-(4-chlorophenyl)-1-methyl-3-oxo-1-propenyl]amino{-3-4-[2-(5-methyl-2-phenyl-1,3-oxazol-4-yl)ethoxy]phenyl}propanoic acid (2S)-2-{[(Z)-1-methyl-3-(3-nitrophenyl-3-oxo-1-propenyl]
amino}-3-{4-[2-(5-methyl-2-phenyl-1,3-oxazol-4-yl)
ethoxy]phenyl}propanoic acid (2S)-2-({(Z)-3-[2-fluoro-3-(trifluoromethyl)phenyl]-1-
methyl-3-oxo-1-propenyl}amino)-3-{4-[2-(5-methyl-2-
phenyl-1,3-oxazol-4-yl)ethoxy]phenyl}propanoic acid (2S)-2-{[(Z)-3-(4-isopropoxyphenyl)-1-methyl-3-oxo-1-
propenyl]amino}-3-{4-[2-(5-methyl-2-phenyl-1,3-
oxazol-4-yl)ethoxy]phenyl}propanoic acid (2S)-2-{[(Z)-3-(2-chlorophenylyl)-1-methyl-3-oxo-1-
propenyl]amino}-3-{4-[2-(5-methyl-2-phenyl-1,3-
oxazol-4-yl)ethoxy]phenyl}propanoic acid (2S)-2-{[(Z)-3-(2-furyl)-1-methyl-3-oxo-1-
propenylamino}-3-{4-[2-(5-methyl-2-phenyl-1,3-oxazol-
4-yl)ethoxy]phenyl}propanoic acid (2S)-2-{[(Z)-1-methyl-3-oxo-3-(2-pyrazinyl)-1-propenyl]
amino}-3-{4-[2-(5-methyl-2-phenyl-1,3-oxazol-4-yl)
ethoxy]phenyl}propanoic acid (2S)-2-{[(Z)-3-(2,4-difluorophenyl)-1-methyl-3-oxo-1-
propenyl]amino}-3-{4-[2-(5-methyl-2-phenyl-1,3-
oxazol-4-yl)ethoxy]phenyl}propanoic acid (2S)-2-{[(Z)-1-methyl-3-oxo-3-(1,3-thiazol-2-yl)-1-
propenyl]amino}-3-{4-[2-(5-methyl-2-phenyl-1,3-
oxazol-4-yl)ethoxy]phenyl}propanoic acid (2S)-2-{[(Z)-1-methyl-3-oxo-3-(3-thienyl)-1-propenyl]
amino}-3-{4-[2-(5-methyl-2-phenyl-1,3-oxazol-4-yl)
ethoxy]phenyl}propanoic acid (2S)-2-{[(Z)-1-methyl-3-oxo-3-(2-pyridinyl)-1-propenyl]
amino}-3-{4-[2-(5-methyl-2-phenyl-1,3-oxazol-4-yl)
ethoxy]phenyl}propanoic acid (2S)-2-{[(Z)-1-ethyl-3-(4-fluorophenyl)-3-oxo-1-propenyl]
amino}-3-{4-[2-(5-methyl-2-phenyl-1,3-oxazol-4-yl)
ethoxy]phenyl}propanoic acid (2S)-2-{[(Z)-1-methyl-3-oxo-3-phenyl-1-propenyl]amino}-
3-{4-[2-(5-methyl-2-phenyl-1,3-thiazol-4-yl)ethoxy]
phenyl}propanoic acid (2S)-2-{[(Z)-3-(2-fluorophenyl)-1-methyl-3-oxo-1-
propenyl]amino}-3-{4-[2-(5-methyl-2-phenyl-1,3-
oxazol-4-yl)ethoxy]phenyl}propanoic acid (2S)-2-{[(Z)-3-(2,3-difluorophenyl)-1-methyl-3-oxo-1-
propenyl]amino}-3-{4-[2-(5-methyl-2-phenyl-1,3-
oxazol-4-yl)ethoxy]phenyl}propanoic acid (2S)-2-{[(Z)-3-(2-hydroxyphenyl-1-methyl-3-oxo-1-
propenyl]amino}-3-{4-[2-methyl-2-phenyl-1,3-oxazol-4-
yl)ethoxy]phenyl}propanoic acid (2S)-3-{4-[2-(5-methyl-2-phenyl-1,3-oxazol-4-yl)ethoxy]
phenyl}-2-{[(Z)-3-oxo-3-phenyl-1-propyl-1-propenyl]
amino}propanoic acid (2S)-2-{[(Z)-3-(4-methoxyphenyl)-1-methyl-3-oxo-1-
propenyl]amino}-3-{4-[2-(5-methyl-2-phenyl-1,3-
oxazol-4-yl)ethoxy]phenyl}propanoic acid (2S)-3-(4-{2-[2-(4-methoxyphenyl)-5-methyl-1,3-oxazol-4-
yl]ethoxy}phenyl)-2-{[(Z)-1-methyl-3-oxo-3-phenyl-1-
propenyl]amino}propanoic acid (2S)-2-{[(Z)-3-cyclohexyl-1-methyl-3-oxo-1-propenyl]
amino}-3-{4-[2-(5-methyl-2-phenyl-1,3-oxazol-4-yl)
ethoxy]phenyl}propanoic acid (2S)-3-(4-{2-[2-(4-isopropoxyphenyl)-5methyl-1,3-oxazol-
4-yl]ethoxy}phenyl)-2-{[(Z)-1-methyl-3-oxo-3-phenyl-
1-propenyl]amino}propanoic acid (2S)-2-{[(Z)-1-heptyl-3-oxo-3-phenyl-1-propenyl]amino}-
3-{4-[2-(5-methyl-2-phenyl-1,3-oxazol-4-yl)ethoxy]
phenyl}propanoic acid (2S)-2-{[(Z)-1-methyl-3-(3-methylphenyl)-3-oxo-1-
propenyl]amino}-3-{4-[2-(5-methyl-2-phenyl-1,3-
oxazol-4-yl)ethoxy]phenyl}propanoic acid (2S)-2-{[(Z)-1-ethyl-3-oxo-3-phenyl-1-propenyl]amino}-3-
(4-{2-[2-(4-methoxyphenyl)-5-methyl-1,3-oxazol-4-yl]
ethoxy}phenyl)propanoic acid (2S)-3-{4-[2-(5-methyl-2-phenyl-1,3-oxazol-4-yl)ethoxy]
phenyl}-2-{-[(Z)-3-oxo-3-phenyl-1-(trifluoromethyl)-1-
propenyl]amino}propanoic acid (2S)-3-{4-[2-(5-methyl-2-phenyl-1,3-thiazol-4-yl)ethoxy]
phenyl}-2-{[(Z)-3-oxo-3-phenyl-1-(trifluoromethyl)-1-
propenyl]amino}propanoic acid (2S)-2-({(Z)-1-ethyl-3-oxo-3-[4-(trifluoromethyl)phenyl]-
1-propenyl}amino)-3-(4-{2-[2-(4-fluorophenyl)-5-
methyl-1,3-oxazol-4-yl]ethoxy}phenyl)propanoic acid (2S)-2-({(Z)-1-ethyl-3-oxo-3-[4-(trifluoromethyl)phenyl]-
1-propenyl}amino)-3-(4-{2-[2-(4-isopropoxyphenyl)-5-
methyl-1,3-oxazol-4-yl]ethoxy}phenyl)propanoic acid (2S)-2-({(Z)-1-ethyl-3-oxo-3-[4-(trifluoromethyl)phenyl]-
1-propenyl}amino)-3-(4-{2-[2-(4-methoxyphenyl)-5-
methyl-1,3-oxazol-4-yl]ethoxy}phenyl)propanoic acid (2S)-3-(4-{2-[2-(4-fluorophenyl)-5-methyl-1,3-oxazol-4-yl]
ethoxy}phenyl)-2-{[(Z)-3-oxo-3-phenyl-1-
(trifluoromethyl)-1-propenyl]amino}propanoic acid (2S)-2-{[(Z)-1-methyl-3-oxo-3-phenyl-1-propenyl]amino}-
3-{4-[(5-methyl-2-phenyl-1,3-oxazol-4-yl)methoxy]
phenyl}propanoic acid (2S)-3-{4-[2-(5-ethyl-2-phenyl-1,3-oxazol-4-yl)ethoxy]
phenyl}-2-{[(Z)-1-methyl-3-oxo-3-phenyl-1-propenyl]
amino}propanoic acid (2S)-2-{[(Z)-1-methyl-3-oxo-3-phenyl-1-propenyl]amino}-
3-{4-[2-(2-phenyl-5-propyl-1,3-oxazol-4-yl)ethoxy]
phenyl}propanoic acid (2S)-2-{[(Z)-1-methyl-3oxo-3-phenyl-1-propenyl]amino}-
3-{4-[3-(5-methyl-2-phenyl-1,3-oxazol-4-yl)propoxy]
phenyl}propanoic acid (2S)-3-{4-[2-(5-ethyl-2-phenyl-1,3-oxazol-4-yl)ethoxy]
phenyl}-2-{[(Z)-3-oxo-3-phenyl-1-(trifluoromethyl)-1-
propenyl]amino}propanoic acid (2S)-3-{4-[3-(5-methyl-2-phenyl-1,3-oxazol-4-yl)propoxy]
phenyl}-2-{[(Z)-3-oxo-3-phenyl-1-(trifluoromethyl)-1-
propenyl]amino}propanoic acid (2S)-3-{4-[(2-(5-ethyl-2-phenyl-1,3-thiazol-4-yl)ethoxy]
phenyl}-2-{[(Z)-3-oxo-3-phenyl-1-(trifluoromethyl)-1-
propenyl]amino}propanoic acid (2S)-3-(4-{2-[5-ethyl-2-(4-fluorophenyl)-1,3-oxazol-4yl]
ethoxy}phenyl)-2-{[(Z)-3-oxo-3-phenyl-1-
(trifluoromethyl)-1-propenyl]amino}propanoic acid (2S)-3-(4-{3-[5-ethyl-2-(4-fluorophenyl)-1,3-oxazol-4-yl]
propoxy}phenyl)-2-{[(Z)-3oxo-3-phenyl-1-
(trifluoromethyl)-1-propenyl]amino}propanoic acid (2S)-3-(4-{2-[5-ethyl-2-(4-fluorophenyl)-1,3-thiazol-4-yl]
ethoxy}phenyl)-2-{[(Z)-3-oxo-3-phenyl-1-
(trifluoromethyl)-1-propenyl]amino}propanoic acid (2S)-3-(4-{3-[5-ethyl-2-(4-fluorophenyl)-1,3-oxazol-4-yl]
propoxy}phenyl)-2-({(Z)-1-ethyl-3-oxo-3-[4-
(trifluoromethyl)phenyl]-1-propenyl}amino)propanoic
acid (2S)-2-({(Z)-1-ethyl-3-oxo-3-[4-(trifluoromethyl)phenyl]-
1-propenyl}amino)-3-{4-[3-(5-ethyl-2-phenyl-1,3-
oxazol-4-yl)propoxy]phenyl}propanoic acid (2S)-3-(4-{3-[5-ethyl-2-(4-fluorophenyl)-1,3-oxazol-4-yl]
propoxy}phenyl)-2-({(Z)-1-methyl-3-oxo-3-[4-
(trifluoromethyl)phenyl]-1-propenyl}amino)propanoic
acid (2S)-3-{4-[3-(5-ethyl-2-phenyl-1,3-oxazol-4-yl)propoxy]
phenyl}-2-({(Z)-1-methyl-3-oxo-3-[4-(trifluoromethyl)
phenyl]-1-propenyl}amino)propanoic acid (2S)-3-{4-[3-(5-ethyl-2-phenyl-1,3-oxazol-4-yl)propoxy]
phenyl}-2-{[(Z)-3-oxo-3-phenyl-1-(trifluoromethyl)-1-
propenyl]amino}propanoic acid (2S)-3-{4-[(5-ethyl-2-phenyl-1,3-thiazol-4-yl)methoxy]
phenyl}-2-{[(Z)-3-oxo-3-phenyl-1-(trifluoromethyl)-1-
propenyl]amino}propanoic acid (2S)-3-{4-[(5-ethyl-2-phenyl-1,3-thiazol-4-yl)methoxy]
  phenyl}-2-({(Z)-1-methyl-3-oxo-3-[4-(trifluoromethyl)
  phenyl]-1-propenyl}amino)propanoic acid
(2S)-3-{4-[(5-ethyl-2-phenyl-1,3-oxazol-4-yl)methoxy]
  phenyl}-2-{[(Z)-3-oxo-3-phenyl-1-(trifluoromethyl)-1-
  propenyl]amino}propanoic acid
(2S)-3-(4-{[5-ethyl-2-(4-fluorophenyl)-1,3-oxazol-4-yl]
  methoxy}phenyl)-2-{[(Z)-3-oxo-3-phenyl-1-
  (trifluoromethyl)-1-propenyl]amino}propanoic acid
(2S)-2-({(Z)-1-ethyl-3-oxo-3-[4-(trifluoromethyl)phenyl]-
  1-propenyl}amino)-3-{4-[(5ethyl-2-phenyl-1,3-oxazol-4-
  yl)methoxy]phenyl}propanoic acid
(2S)-3-(4-{[5-ethyl-2-(4-fluorophenyl)-1,3-oxazol-4-yl]
  methoxy}phenyl)-2-({(Z)-1-ethyl-3-oxo-3-[4-
  (trifluoromethyl)phenyl]-1-propenyl}amino)propanoic
  acid
(2S)-3-{4-[(5-ethyl-2-phenyl-1,3-oxazol-4-yl)methoxy]
  phenyl}-2-({(Z)-1-methyl-3-oxo-3-[4-(trifluoromethyl)
  phenyl]-1-propenyl}amino)propanoic acid
(2S)-3-(4-{[5ethyl-2-(4-fluorophenyl)-1,3-oxazol-4-yl]
  methoxy}phenyl)-2-({(Z)-1-methyl-3-oxo-3-[4-
  (trifluoromethyl)phenyl]-1-propenyl}amino)propanoic
  acid
(2S)-2-({(Z)-1-ethyl-3-oxo-3-[4-(trifluoromethyl)phenyl]-
  1-propenyl}amino)-3-{4-[(5ethyl-2-phenyl-1,3-thiazol-
  4-yl)methoxy]phenyl}propanoic acid
(2S)-3-(4-{2-[5-ethyl-2-(4-fluorophenyl)-1,3-oxazol-4-yl]
  ethoxy}phenyl)-2-({(Z)-1-ethyl-3-oxo-3-[4-
  (trifluoromethyl)phenyl]-1-propenyl}amino)propanoic
  acid
(2S)-3-(4-{2-[5-ethyl-2-(4-fluorophenyl)-1,3-thiazol-4-yl]
  ethoxy}phenyl)-2-({(Z)-1-ethyl-3-oxo-3-[4-
  (trifluoromethyl)phenyl]-1-propenyl}amino)propanoic
  acid
(2S)-2-({(Z)-1-ethyl-3-oxo-3-[4-(trifluoromethyl)phenyl]-
  1-propenyl}amino)-3-{4-[2-(5-ethyl-2-phenyl-1,3-
  thiazol-4-yl)ethoxy]phenyl}propanoic acid, and pharmaceutically acceptable salts and solvates thereof.

Preferred compounds of the invention include
(2S)-2-{[(Z)-1-methyl-3-oxo-3-phenyl-1-propenyl]amino}-
  3-{4-[2-(5-methyl-2-phenyl-1,3-oxazol-4-yl)ethoxy]
  phenyl}propanoic acid
(2S)-2-{[(Z)-1-ethyl-3-oxo-3-phenyl-1-propenyl]amino}-3-
  [4-(2-{5-methyl-2-[4-(trifluoromethyl)phenyl]-1,3-
  oxazol-4-yl}ethoxy)phenyl]propanoic acid
(2S)-2-{[(Z)-1-methyl-3-oxo-3-(2,3,4-trifluorophenyl)-1-
  propenyl]amino}-3-{4-[2-(5-methyl-2-phenyl-1,3-
  oxazol-4-yl)ethoxy]phenyl}propanoic acid
(2S)-2-{[(Z)-1-methyl-3-(4-nitrophenyl)-3-oxo-1-propenyl]
  amino}-3-{4-[2-(5-methyl-2-phenyl-1,3-oxazol-4-yl)
  ethoxy]phenyl}propanoic acid
(2S)-2-({(Z)-1-methyl-3-oxo-3-[4-(trifluoromethyl)
  phenyl]-1-propenyl}amino)-3-{4-[2-(5-methyl-2-phenyl-
  1,3-oxazol-4-yl)ethoxy]phenyl}propanoic acid
(2S)-2-{[(Z)-1-methyl-3-oxo-3-(2,4,5-trifluorophenyl)-1-
  propenyl]amino}-3-4-[2-(5-methyl-2-phenyl-1,3-oxazol-
  4-yl)ethoxy]phenyl}propanoic acid
(2S)-2-{[(Z)-1-ethyl-3-oxo-3-phenyl-1-propenyl]amino}-3-
  {4-[2-(5-methyl-2-phenyl-1,3-oxazol-4-yl)ethoxy]
  phenyl}propanoic acid
(2S)-3-(4-{2-[2-(4-fluorophenyl)-5-methyl-1,3-thiazol-4-
  yl]ethoxy}phenyl)-2-{[(Z)-3-oxo-3-phenyl-1-
  (trifluoromethyl)-1-propenyl]amino}propanoic acid
(2S)-2-({(Z)-1-ethyl-3-oxo-3-[4-(trifluoromethyl)phenyl]-
  1-propenyl}amino)-3-(4-{2-[2-(4-fluorophenyl)-5-
  methyl-1,3-thiazol-4-yl]ethoxy}phenyl)propanoic acid
(2S)-2-{[(Z)-1-butyl-3-oxo-3-phenyl-1-propenyl]amino}-3-
  {4-[2-(5-methyl-2-phenyl-1,3-oxazol-4-yl)ethoxy]
  phenyl}propanoic acid
(2S)-2-{[(Z)-3-(4-chlorophenyl)-1-methyl-3-oxo-1-
  propenyl]amino}-3-{4-[2-(5-methyl-2-phenyl-1,3-
  oxazol-4-yl)ethoxy]phenyl}propanoic acid
(2S)-3-{4-[2-(5-methyl-2-phenyl-1,3-oxazol-4-yl)ethoxy]
  phenyl}-2-{[(Z)-3-oxo-3-phenyl-1-propyl-1-propenyl]
  amino}propanoic acid
(2S)-3-{4-[2-(5methyl-2-phenyl-1,3-oxazol-4-yl)ethoxy]
  phenyl}-2-{[(Z)-3-oxo-3-phenyl-1-(trifluoromethyl)-1-
  propenyl]amino}propanoic acid
(2S)-2-({(Z)-1-ethyl-3-oxo-3-[4-(trifluoromethyl)phenyl]-
  1-propenyl}amino)-3-(4-{2-[2-(4-fluorophenyl)-5-
  methyl-1,3-oxazol-4-yl]ethoxy}phenyl)propanoic acid
(2S)-2-({(Z)-1-ethyl-3-oxo-3-[4-(trifluoromethyl)phenyl]-
  1-propenyl}amino)-3-(4-{2-[2-(4-methoxyphenyl)-5-
  methyl-1,3-oxazol-4-yl]ethoxy}phenyl)propanoic acid
(2S)-3-(4-{2-[2-(4-fluorophenyl)-5-methyl-1,3-oxazol-4-yl]
  ethoxy}phenyl)-2-{[(Z3-oxo-3-phenyl-1-
  (trifluoromethyl)-1-propenyl]amino}propanoic acid
(2S)-2-{[(Z)-1-methyl-3-oxo-3-phenyl-1-propenyl]amino}-
  3-{4-[(5-methyl-2-phenyl-1,3-oxazol-4-yl)methoxy]
  phenyl}propanoic acid
(2S)-3-{4-[2-(5-ethyl-2-phenyl-1,3-oxazol-4-yl)ethoxy]
  phenyl}-2-{[(Z)-3-oxo-3-phenyl-1-propenyl]
  amino}propanoic acid
(2S)-2-{[(Z)-1-methyl-3-oxo-3-phenyl-1-propenyl]amino{-
  3-4-[3-(5-methyl-2-phenyl-1,3-oxazol-4-yl)propoxy]
  phenyl}propanoic acid
(2S)-3-{4-[2-(5-ethyl-2-phenyl-1,3-oxazol-4-yl)ethoxy]
  phenyl)-2-{[(Z)-3-phenyl-1-(trifluoromethyl)-1-
  propenyl]amino}propanoic acid
(2S)-3-{4-[2-(5ethyl-2-phenyl-1,3-thiazol-4-yl)ethoxy]
  phenyl}-2[(Z)-3-oxo-phenyl-1-(trifluoromethyl)-1-
  propenyl]amino}propanoic acid
(2S)-3-(4-{2-[5-ethyl-2-(4-fluorophenyl )-1,3-oxazol-4-yl]
  ethoxy}phenyl)-2-{[(Z)-3-oxo-3-phenyl-1-
  (trifluoromethyl)-1-propenyl]amino}propanoic acid
(2S)-3-(4-{3-[5-ethyl-2-(4-fluorophenyl)-1,3-oxazol-4-yl]
  propoxy)}phenyl)-2-{[(Z)-3-oxo-3-phenyl-1-
  (trifluoromethyl)-1-propenyl]amino}propanoic acid
(2S)-3-(4-{2-[5-ethyl-2-(4-fluorophenyl)-1,3-thiazol-4-yl]
  ethoxy}phenyl)-2-{[(Z)-3-oxo-3-phenyl-1-
  (trifluoromethyl)1-propenyl]amino}propanoic acid
(2S)-3-(4-{[5-ethyl-2-(4-fluorophenyl)-1,3-oxazol-4-yl]
  propoxy}phenyl)-2-({(Z)-1-ethyl-3-oxo-3-[4-
  (trifluoromethyl)phenyl]-1-propenyl}amino)propanoic
  acid
(2S)-2-({(Z)-1-ethyl-3-oxo-3-[4-(trifluoromethyl)phenyl]-
  1-propenyl}amino)-3-{4-[3-(5-ethyl-2-phenyl-1,3-
  oxazol-4-yl)propoxy]phenyl}propanoic acid
(2S)-3-(4-{3-[5-ethyl-2-4-fluorophenyl)-1,3-oxazol-4-yl]
  propoxy}phenyl)-2-({(Z)-1-methyl-3-oxo-3-[4-
  (trifluoromethyl)phenyl]-1-propenyl}amino)propanoic
  acid
(2S)-3-{4-[3-(5-ethyl-2-phenyl-1,3-oxazol-4-y)propoxy]
  pheny}-l2-({(Z)-1-methyl-3-oxo-3-[4-(trifluoromethyl)
  phenyl]-1-propenyl}amino)propanoic acid
(2S)-3-(4-{[5ethyl-2-(4-fluorophenyl)-1,3-oxazol-4-yl]
  methoxy}phenyl)-2-{[(Z)-3-oxo-3-phenyl-1-
  (trifluoromethyl)-1-propenyl]amino}propanoic acid
(2S)-3-{4-[(5-ethyl-2-phenyl-1,3-oxazol-4-yL)methoxy]
  phenyl}-2-({(Z)-1-methyl-3-oxo-3-[4-(trifluoromethyl)
  phenyl]-1-propenyl}amino)propanoic acid
(2S)-3-(4-{[5-ethyl-2-(4-fluorophenyl)-1,3-oxazol-4-yl]
  methoxy}phenyl)-2-({(Z)-1-methyl-3-oxo-3-[4-
  (trifluoromethyl)phenyl]-1-propenyl}amino)propanoic
  acid
(2S)-3-(4-{2-[5-ethyl-2-(4-fluorophenyl)-1,3-thiazol-4-yl]
  ethoxy}phenyl)-2-({(Z)-1-ethyl-3-oxo-3-[4-

(trifluoromethyl)phenyl]-1-propenyl}amino)propanoic acid and pharmaceutically acceptable salts and solvates thereof.

Many of the compounds of formula (I) are dual activators of hPPARγ and hPPARα As used herein, by "activating compound", or "activator", or the like, is meant those compounds which achieve at least 50% activation of human PPARγ ("hPPARγ") or hPPARα (relative to the appropriate indicated positive control) in the transfection assay described below at concentrations of $10^{-7}$ M or less. As used herein, a "dual activator" is a compound that is an activator of both PPARγ and PPARα.

$$\text{The ratio } \frac{EC_{50}\ hPPAR\alpha}{EC_{50}\ hPPAR\gamma}$$

defines the relative activity of hPPARα to hPPARγ. Preferably, the dual activators of this invention have a relative hPPARα to hPPARγ activity of from 0.02 to 50.

Those skilled in the art will recognize that stereocenters exist in compounds of formula (I). Accordingly, the present invention includes all possible stereoisomers and geometric isomers of formula (I) and includes not only racemic compounds but also the optically active isomers as well. When a compound of formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of formula (I) are possible, the present invention is intended to include all tautomeric forms of the compounds.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable s acid salts include hydrochloric, hydrobromic, sulfuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts and solvates.

The terms $C_{1-3}$alkyl, $C_{4-6}$cycloalkyl, $C_1$alkylene, $C_{2-6}$alkenyl and the like, as used herein, indicate groups that may contain the indicated range of carbon atoms, for example 1 to 3 carbon atoms. Unless otherwise indicated, such groups can be straight chained or branched.

The term 5- or 6-membered heterocyclic group as used herein includes 5- or 6-membered substituted or unsubstituted heterocycloalkyl and heteroaryl groups, e.g. substituted or unsubstituted imidazolidinyl, piperidyl, piperazinyl pyrrolidinyl, morpholinyl, pyridyl, pyridazinyl, pyrimidinyl, pyrazinyl, pyrrolyl, pyrazolyl, imidazolyl, pyranyl, furyl, thienyl, oxazolyl, isoxazolyl, oxadiazolyl, thiazolyl, thiadiazolyl, triazolyl or tetrazolyl. Particularly preferred heterocycles are pyridine, pyrazine, thiophene, furan, and thiazole.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day.

While it is possible that compounds of the present invention may be therapeutically administered as the raw chemical, it is preferable to present the active ingredient as a pharmaceutical formulation. Accordingly, the present invention further provides for a pharmaceutical formulation comprising a compound of formula (I) or a pharmaceutically acceptable salt or solvate thereof together with one or more pharmaceutically acceptable carriers therefor and, optionally, other therapeutic and/or prophylactic ingredients.

Formulations of the present invention include those especially formulated for oral, buccal, parenteral, transdermal, inhalation, intranasal, transmucosal, implant, or rectal administration, however, oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The formulations according to the invention may contain between 0.1–99% of the active ingredient, conveniently from 30–95% for tablets and capsules and 3–50% for liquid preparations.

There is further provided by the present invention processes for the preparation of compounds of the invention Unless otherwise indicated, R', $R^1$, $R^2$, $R^3$, $R^4$, $R^5$, $R^6$, n, and X are as defined above.

A compound of structural formula (I) may be prepared from the condensation of a compound of formula (II):

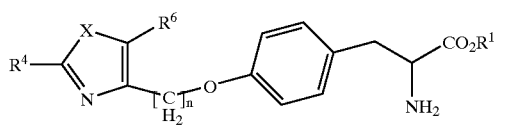

(II)

with a compound of formula (III), for example, in a polar organic solvent, such,

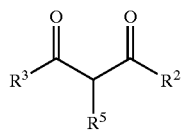

(III)

as methanol, at temperatures from −20° C. to 150° C., such as 65° C., in the presence of a dehydrating agent such as trimethylorthoformate and/or molecular sieves.

Alternatively, a compound of formula (I) where $R^5$ is hydrogen may be prepared by reaction of a compound of formula (II) with a compound of:

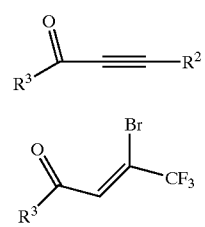

(IVa)

(IVb)

formula (IVa) in an organic solvent such as methanol at temperatures from −20° C. to 150° C., such as 65° C., in the presence of a base, such as diisopropylethylamine.

Compounds of Formula (I) where $R^2$ is $CF_3$ may be prepared from the reaction of compounds of formula (II) with compounds of formula (IVb) in an organic solvent such as methanol at temperatures from −20° C. to 150° C., such as 23° C., in the presence of a base such as diisopropylamine.

Compounds of formula (II) may be prepared via alkylation of compounds of formula (V), preferably where $R^1$ is hydrogen, with compounds of formula (VI), where R" is an activating group such as mesylate followed by:

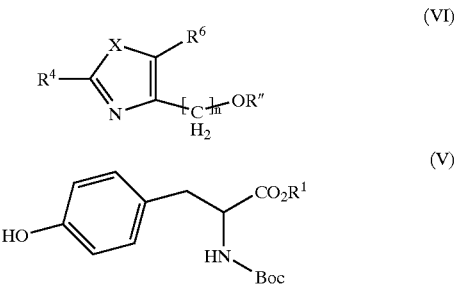

(VI)

(V)

deprotection of the amine under acidic conditions such as 4.0 N HCl in dioxane solution at 20° C., or trifluoroacetic acid in dichloromethane at 20° C.

Alternatively, compounds of formula (II) may be prepared from reaction of compounds of formula (V), preferably where $R^1$ is methyl, with compounds of formula (VI), preferably where R" is hydrogen, in an organic solvent such as toluene at temperatures from −20° C. to 150° C. such as 20° C. in the presence of triphenylphosphine and diethylazodicarboxylate in a Mitsunobu type procedure. Standard methyl ester hydrolysis conditions such as lithium hydroxide in tetrahydrofuran and water at 20° C. followed by amine deprotection as hereinbefore described (see also Greene, T. W. and Wutz, P. G. M. "Protective Groups in Organic Synthesis" $2^{nd}$ edition, 1991, John Wiley and Sons for a general discussion on protective group installation/removal) provides compounds of structural formula (II).

Compounds of formula (V) are commercially available and may also be prepared by someone skilled in the art from commercially available compounds.

Compounds of formula (VI), for example where R" is mesylate, may be prepared by reaction of an alcohol of formula (VI) where R" is hydrogen, with methanesulfonyl chloride in an organic solvent such as tetrahydrofuran at temperatures from −20° C. to 150° C. such as 0° C. in the presence of an amine base such as triethylamine.

Alcohols of formula (VI) where R" is hydrogen, may be prepared via reduction of the corresponding carboxylic acid or ester of formula (IX) in an organic solvent such as diethyl ether at temperatures of from −20° C. to 100° C., such as 0° C., in the presence of a metal hydride reagent such as lithium aluminum hydride. These acids or esters of formula (IX) may be prepared by a two stage alkylation/cyclization process between an amide or thioamide compound of formula (VII), and a bromoketoester compound of formula (VII), where R'" is alkyl. The alkylation/cyclization reaction may be performed in an organic solvent such as toluene or ethanol at temperatures of from −20° C. to 200° C., such as 110° C., in the presence of a base such as triethylamine. For the preparation of (VIII), see: Chem. Pharm. Bull. (1986), 34(7), 2840–51, J. Med. Chem. (1992), 35(14), 2617–26, patent WO 9731907.

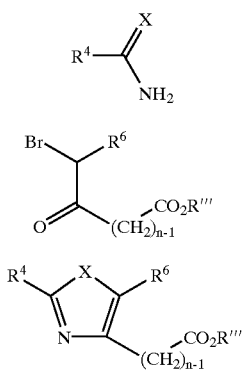

Amides or thioamides of formula (VII) are commercially available or may be prepared from readily available compounds by one skilled in the art.

Compounds of formula (III) are commercially available or may be readily prepared by one skilled in the art, for example, by reacting a ketone of formula (X) with an ester of formula (XII), or by reacting a ketone of formula (XIII) with an ester of formula (XI), by reaction in an organic solvent, such as tetrahydrofuran, at temperatures from −20° C. to 150° C., such as 20° C., in the presence of a base, such as sodium hydride, a metal cation scavenger, such as dibenzo-18-crown-6, and catalytic quantities of an alcohol, such as ethanol (See: Popic, V. V. et al. *Synthesis* 1991, 195–197).

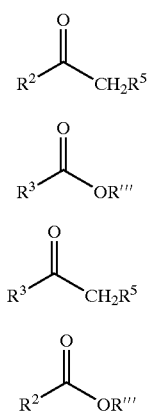

Compounds of formula (IVa) may be prepared from the addition of compounds of formula (XV) to compounds of formula (XIV) in an organic solvent such as tetrahydofuran at temperatures of from −100° C. to 100 ° C. such as −78 ° C. followed by oxidation of the intermediate propargyllic alcohol with an oxidant, such as manganese dioxide, in an organic solvent, such as dichloromethane, at temperatures from −20° C. to 100° C., such as 20° C.

Alternatively, certain yne-one compounds of formula (IVa) may be prepared by dehydration of a compound of formula (III) where $R^5$ is hydrogen in an organic solvent, such as dichloromethane, at temperatures from −20° C. to 100° C., such as 20° C., in the presence of triphenylphosphine, bromine, and a base, such as triethylamine. When $R^2$ is $CF_3$, $R^5$ is hydrogen, and $R^3$ is phenyl, a compound of formula (III) in an organic solvent, such as dichloromethane, at temperatures from −20° C. to 100° C., such as 20° C., in is the presence of triphenylphosphine, bromine, and a base, such as triethylamine yields a compound of formula (IVb). Compounds of formula (X), (XI), (XII), (XIII), (XIV), and (XV) are commercially available or may be prepared from readily available materials from one skilled in the art.

Suitable reaction conditions are described below and in the accompanying Examples. See also, for example, Chung et al., Selective Functionalization of (S)Tyrosine, Tetrahedron, 49(26), pp. 5767–5776, (1993), Solar et al., Selective O-Alkylation of Tyrosine, Journal of Organic Chemistry, 31, pp 1996–1997 (1966), O. Mitsunobu, Synthesis, p 1 (1981), and D. L. Hughes, Org. React. Vol. 42, p 335 (1992).

A compound of formula (I) can be converted to another compound of formula (I). A particular interconversion reaction involves conversion of a compound of formula (I) wherein R' represents $C_{1-3}$alkyl, to a compound of formula (I) wherein R' represents hydrogen, suitably employing hydrolytic techniques e.g. an alkali metal hydroxide, in the presence of an ether solvent e.g. tetrahydrofuran and an alcoholic solvent e.g. methanol or the like. It will therefore be appreciated by persons skilled in the art that compounds which fall within general formula (I), may in some instances, be hereinafter described in the intermediate section, as they are useful for the preparation of other compounds of formula (I).

For any of the general processes and schemes described above, it may be necessary and/or desirable to protect sensitive or reactive groups. Protecting groups are employed according to standard methods of organic synthesis (T. W. Green and P. G. M. Wuts (1991) *Protecting Groups in Organic Synthesis*, John Wiley & Sons). These groups are removed at a convenient stage of synthesis using methods known from the art. Thus, for example, amino groups may be protected by a group selected from aralkyl (e.g. benzyl), acyl, or sulfonyl, e.g. allylsulfonyl, tert-butoxycarbonyl, phthalimide, or tosyl; subsequent removal of the protecting group being effected when desired by hydrolysis or hydrogenolysis as appropriate using standard conditions. Thus, for example, tert-butoxycarbonyl groups may be removed by hydrolysis under acidic conditions. Hydroxyl and carboxyl groups may be protected using any conventional hydroxyl or carboxyl protecting group. Examples of suitable hydroxyl and carboxyl protecting groups include groups selected from alkyl, e.g. methyl, tert-butyl, or methoxymethyl, aralkyl, e.g. benzyl, diphenylmethyl, or triphenylmethyl, heterocyclic groups such as tetrahydropyranyl, acyl. e.g. acetyl or benzoyl, and silyl groups such as trialkylsilyl, e.g. tert-butyldimethylsilyl. The hydroxyl protecting groups may be removed by conventional techniques. Thus, for example, alkyl, silyl, acyl, and heterocyclic groups may be removed by hydrolysis under acidic or basic conditions. Aralkyl groups such as triphenylmethyl may similarly be removed by hydrolysis under acidic conditions. Aralkyl groups such as benzyl may be cleaved by hydrogenolysis in the presence of a Noble metal catalyst such as palladium-on-charcoal. Silyl groups may also conveniently be removed using a source of fluoride ions such as tetra-n-butylammonium fluoride.

15

The following examples are set forth to illustrate the synthesis of some particular compounds of the present invention and to further exemplify particular applications of general processes described above. Accordingly, the following Example section is in no way intended to limit the scope of the invention contemplated herein.

EXAMPLES

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); µL (microliters); N (normal); mM (millimolar); mmol (millimoles); i. v. (intravenous); Hz (Hertz); MHz (megahertz); mol (moles); RT or rt (room temperature); min (minutes); h (hours); mp. (melting point); TLC (thin layer chromatography); HPLC (high pressure liquid chromatography); ms (mass spectrum); ES+(electrospray); $R_f$ (retention fraction); ($t_r$ (retention time); RP (reverse phase); MeOH (methanol); TFA (trifluoroacetic acid); HCl (hydrochloric acid); $HCO_2H$ (formic acid); THF (tetrahydrofuran); $CH_3CN$ (acetonitrile); EtOH (ethanol); $CDCl_3$ (deuterated chloroform); DMSO (dimethylsulfoxide); DMSO-$d_6$ (dimethylsulfoxide-deuterated); EtOAc (ethyl acetate); DCM or $CH_2Cl_2$ (dichloromethane); DMF (dimethylformamide); Et3N (triethylamine); $MgSO_4$ (magnesium sulfate); $H_2O$ (water); LAH (lithium aluminum hydride; NaH (sodium hydride); $Na_2CO_3$ (sodium carbonate); $Na_2SO_4$ (sodium sulfate); $MnO_2$ (manganese dioxide); KCN (potassium cyanide); $BH_3$.THF (borane.tetrahydofuran complex); NaOMe (sodium methoxide); IPA (isoprropanol); Pd/C (palladium on carbon);NaOH (sodium hydroxide; LiOH (lithium hydroxide); DIEA (diisopropylethylamine); $Et_2O$ (diethyl ether; diethyl azodicaboxylate (DEAD); Diisopropyl azodicarboxylate (DIAD); tert-butyloxycarbonyl (BOC); $NaHCO_3$ (saturated aqueous sodium bicarbonate). Brine refers to a saturated aqueous solution of NaCl. Unless otherwise indicated, all temperatures are expressed in ° C. (degrees Centigrade). All reactions conducted at room temperature unless otherwise noted.

The $^1$H NMR spectra were recorded on a Varian VXR-300, a Varian Unity-300, or a Varian Unity400 instrument. Chemical shifts are expressed in parts per million (ppm, δ units). Coupling constants are in units of hertz (Hz). Splitting patterns are designated as s, singlet; d, doublet; t, triplet; q, quartet; m, multiplet; br, broad; hept, heptuplet.

Low-resolution mass spectra (MS) were recorded on a JOEL JMS-AX505HA, JOEL SX-102, Micromass Platform 2 LC/Ms, or a SCIEX-APIiii spectrometers. All mass spectra were taken under electrospray ionization (ES, either in the positive ion mode or negative ion mode) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, iodine staining, or 7% ethanolic phosphomolybdic acid or p-anisidehyde solutions. Flash column chromatography was performed on silica gel (230–400 mesh, Merck).

Analytical purity was assessed on a Hewlett Packard series 1050 or 1100 system equipped with a diode array spectrometer. The stationary phase was either a Dynamax C8 column (25 cm×4.1 mm), a Dynamax 60A C18 column (25 cm×4.6 mm), a Vydac C18 column (5 m, 4.6 mm×250 mm), a Supelco C18 column (5m, 4.6 mm×150 mm), or a Rainin C18 column (5 m, 4.6 mm×250 mm). The flow rate was 1.0 to 1.5 ml/min. (t0=2.8 or 3.0 min.) and the solvent systems were as described below. Enantiomeric purity was assessed using either a Chiralpak AD column (25 cm×4.6 mm) or a Chiralpak OD column (25 cm×4.6 mm) on either a Hewlet Packard series 1050 HPLC system equipped with a diode array spectrometer or on a Supercritical Fluid (SFC) system using $CO_2$/methanol as the mobile phase.

Intermediate 1: 2-[5-methyl-2-phenyl-1,3-oxazol-4-yl]acetic acid methyl ester

To a solution of 140 g (0.67 mol) of methyl 4-bromo-3-oxo-pentanoate in 300 mL of anhydrous toluene was added 210 g (1.73 mol) of benzamide, 132 g (0.93 mol) of sodium hydrogen phosphate, and ~20 mL of EtOH. The suspension was stirred with heating to 95° C. for 24 h, then cooled to 0° C., filtered, and the solids washed with cyclohexane (2×100 mL) followed by 20% EtOAc in hexanes (200 mL). The combined filtrates were washed with 2×100 mL 10% KOH solution and brine (100 mL). The organics were dried ($MgSO_4$), concentrated to a thin oil, and purified by chromatography on 1 kg of silica gel (230–400 mesh). Gradient elution of the column with 10% to 50% EtOAc in Hexanes gave 54 grams (35% yield) of the title compound as a pale yellow oil; $^1$H NMR ($CDCl_3$, 400 MHz) δ8.0–7.98 (m, 2H), 7.43–7.40 (m, 3H), 3.73 (s, 3H), 3.59 (s, 2H), 2.37 (s, 3H); low resolution MS (ES+)m/e 232.4 (MH$^+$); TLC $R_f$=0.64 (4/1 hexanes/EtOAc).

Intermediate 1B: 2-[5-ethyl-2-phenyl-1,3oxazol-4-yl]acetic acid ethyl ester

The title compound was prepared (as described above for the preparation of example 1) from ethyl 4-bromo-3-oxo-hexanoate (3.32 g, 14 mmol) and 6.79 g (56 mmol) of benzamide to give 710 mg of Intermediate 1B: TLC $R_f$=0.69 (2/1 hexanes/EtOAc); $^1$H NMR ($CDCl_3$, 300 MHz) δ7.98 (m, 2H), 7.41 (m, 3H), 4.18 (q, 2H, J=6.9), 3.57 (s, 2H), 2.72 (q, 2H, J=7.5), 1.29–1.24 low resolution MS (ES$^+$)m/e 260.1 (MH$^+$).

Intermediate 1C: 2-[2-phenyl-5-propyl-1,3-oxazol-4-yl]acetic acid ethyl ester

The title compound was prepared (as described above for the preparation of example 1) from ethyl 4-bromo-3-oxo-heptanoate (2.83 g, 11.4 mmol) and 5.51 g (45 mmol) of benzamide to give 820 mg of Intermediate IC: TLC $R_f$=0.70 (2/1 hexanes/EtOAc); $^1$H NMR ($CDCl_3$, 300 MHz) δ7.98 (m, 2H), 7.43–7.4 (m, 3H), 4.18 (q, 2H, J=7.2), 3.56 (s, 2H), 2.66 (t, 2H, J=7.5), 1.76–1.68 (m, 2H), 1.27 (t, 3H, J=7.2), 0.99 (t, 3H, J=7.2); low resolution MS (ES$^+$)m/e 274.1 (MH$^+$).

Intermediate 1D: 5-methyl-2-phenyl-1, 3oxazole4carboxylic acid

Commercial sources.

Intermediate 1E: 5ethyl-2-phenyl-1,3-oxazole4-carboxylic acid

Intermediate 1E was prepared (as described below for the preparation of intermediate 2B) from 4.08 g of benzamide, 5.0 g of ethyl 3-bromo-2-oxo-pentanoate, and 10 mL of toluene. Solids were collected and washed with cold water after cooling of the NaOH solution. Heating these solids with citric acid as described followed by cooling and isolation of the resulting solids gave 410 mg (9% yield) of the title compound; $^1$H NMR (CDCl$_3$, 300 MHz) δ8.06–8.03 (m, 2H), 7.49–7.43 (m, 3H), 3.14 (q, 2H, J=8.0), 1.34 (t, 3H, J=8.0); low resolution MS (ES$^+$)m/e 217.8 (MH$^+$).

Intermediate 2: 2-[5-methyl-2-phenyl-1,3-thiazol-4-yl]acetic acid methyl ester

A solution of 13.13 g (95.7 mmol) of thiobenzamide and 5.0 g (23.9 mmol) of methyl 4-bromo-3-oxo-pentanoate in 25 mL of dry toluene was heated at 90° C. for 5 h. The solution was poured into EtOAc/water and the aqueous phase extracted with EtOAc. The organics were washed with brine, dried (MgSO$_4$), filtered, and concentrated. The crude oil was purified by silica gel chromatography eluting with hexanes/EtOAc (3/1 to 2/1) to afford 4.14 g (70%) yield) of the title compound as a pale orange-colored oil: $^1$H NMR (CDCl$_3$, 400 MHz) δ7.97 (m, 2H), 7.11 (m, 2H), 3.73 (s, 3H), 3.56 (s, 2H), 2.36 (s, 3H).

Intermediate 2B: 2-[5-ethyl-2-phenyl-1,3-thiazol-4-yl]acetic acid

A suspension of 8.7 g (63.3 mmol) of thiobenzamide and 10 g (42.2 mmol) of ethyl 4-bromo-3-oxo-hexanoate in 45 mL of toluene was refluxed for 6 hrs with Dean-Stark trap removal of water. Cooled, added methanol, and continued reflux for 1 h. Cooled, partially concentrated (~½ volume), then 30 mL of 2.0 M NaOH solution was added. Stirred the mixture at 80° C. for 2 hrs before cooling and extraction of the aqueous with EtOAc. The aqueous phase was treated with 70 mL of 1.0 M citric acid with heating (70° C.) for 45 min. The mixture was extracted with EtOAc, and the extracts were dried. over MgSO$_4$, filtered and concentrated to yield a yellow colored solid upon standing at ambient temperature (8.4 g, ~80% yield); $^1$H NMR (CDCl$_3$, 300 MHz) δ7.95–7.87 (m, 2H), 7.48–7.45 (m, 3H), 3.86 (s, 2H), 2.85 (q, 2H, J=7.5), 1.36 (t, 3H, J=7.5).

Intermediate 2C: 5-ethyl-2-phenyl-1,3-thiazole4carboxylic acid

Intermediate 2C was prepared as described above for the preparation of intermediate 2B from 4.61 g of thiobenzamide, 5.0 g of ethyl 3-bromo-2-oxo-pentanoate, and 14 mL of toluene. Solids were collected and washed with cold water after cooling of the NaOH solution. Heating these solids with citric acid as described followed by cooling and isolation of the resulting solids gave 3.74 g (72% yield) of intermediate 2C; $^1$H NMR (CDCl$_3$, 300 MHz) δ7913–7.91 (m, 2H), 7.51–7.50 (m, 3H), 3.39 (q, 2H, J=7.8), 1.42 (t, 3H, J=7.8); low resolution MS (ES$^+$)m/e 233.81 (MH$^+$).

Intermediate 3: 2-[2-(4-fluorophenyl)-5-methyl-1,3-oxazol-4-yl]acetic acid methyl ester A solution of 667 mg (4.80 mmol) of 4-fluorobenzamide and 1.0 g (4.80 mmol) of methyl 4-bromo-3-oxo-pentanoate in 6 mL of dry toluene was heated at 120° C. for 16 h. The resulting dark slurry was cooled to rt, diluted with 10 mL of EtOAc, and washed with NaHCO$_3$ (1×10 mL). The organic layer was separated, dried (MgSO$_4$), and the solvents removed under reduced pressure. Purification of the material by silica gel flash column chromatography using hexane/EtOAc 4/1 as eluent to afford 308 mg of the title compound as a clear oil: $^1$H NMR (CDCl$_3$, 400 MHz) δ7.97 (m, 2H), 7.11 (m, 2H), 3.73 (s, 3H), 3.56 (s, 2H), 2.36(s, 3H).

Intermediate 3B: 2-[5-ethyl-2-(4-fluorophenyl)-1,3-oxazol-4-yl]acetic acid

The title compound was prepared from 5 g of 4-fluorobenzamide and 5.67 g of ethyl 4-bromo-3-oxo-hexanoate as described in example 2B to give 1.8 grams of intermediate 3B as a solid: $^1$H NMR (CDCl$_3$, 300 MHz) δ7.96 (dd, 2H, J=8.8, 5.3), 7.11 (t, 2H, J=8.6), 3.61 (s, 2H), 2.69 (q, 2H, J=7.5), 1.27 (t, 3H, J=7.5).

Intermediate 3C: 5-ethyl-2-(4-fluorophenyl)-1,3-oxazole-4-carboxylic acid

The title compound was prepared from 6.5 9 of 4-fluorobenzamide and 6.08 g of ethyl 3-bromo-2-oxo-pentanoate (as described in example 2B) to give 1.55 g (22%) of intermediate 3C as a solid: $^1$H NMR (CDCl$_3$, 300 MHz) δ8.12–8.08 (m, 2H), 7.23–7.17 (m, 2H), 3.19 (q, 2H, J=7.5), 1.40 (t, 3H, J=7.5).

Intermediate 4: 2-[2-(4-fluorophenyl)-5-methyl-1,3-thiazol-4-yl]acetic acid ethyl ester A mixture of 8.75 g (56.4 mmol) of 4-fluorobenzamide and 11.79 g (56.4 mmol) of methyl 4-bromo-3-oxo-pentanoate in 45 mL of EtOH was refluxed for 14 h. The solids formed upon cooling were removed via filtration and the solvent removed under reduced pressure. The residue was taken into EtOAc and washed with water, brine, and dried over MgSO$_4$. $^1$H NMR of the crude Intermediate 4 indicated purity sufficient to proceed into the next stage of synthesis. $^1$H NMR (CDCl$_3$, 400 MHz) δ7.97 (m, 2H) 7.11 (m, 2H), 3.73 (s, 3H), 3.56 (s, 2H), 2.36 (s, 3H).

Intermediate 4B: 2-[5-ethyl-2-(4-fluorophenyl)-1,3-thiazol-4-yl]acetic acid

The title compound was prepared from 6.8 g of 4-fluorothiobenzamide and 7.42 g of ethyl 4-bromo-3-oxo-hexanoate as described in example 2B to give 2.9 grams of intermediate 4B as a solid: $^1$H NMR (CDCl$_3$, 300 MHz) δ7.96 (dd, 2H, J=8.8, 5.3), 7.11 (t, 2H, J=8.6), 3.61 (s, 2H), 2.69 (q, 2H, J=7.5), 1.27 (t, 3H, J=7.5).

Intermediate 5: 2-[2-(4-methoxyphenyl)-5-methyl-1,3-oxazol-4-yl]acetic acid methyl ester A mixture of 725 mg (4.80 mmol) of 4-methoxybenzamide and 1.0 g (4.80 mmol) of methyl 4-bromo-3-oxo-pentanoate was heated neat at 120° C. for 2 h. The resulting dark slurry was cooled to RT, diluted with 2 mL of DCM and purified by silica gel flash column chromatography using hexane/EtOAc (3/1) as eluent to afford 189 mg of the title compound as a yellow solid: $^1$H NMR (CDCl$_3$, 400 MHz) δ7.92 (d, 2H, J=8.9), 6.93 (d, 2H, J=8.9), 3.85 (s, 3H), 3.73 (s, 3H), 3.56 (s, 2H), 2.34 (s, 3H); low resolution MS (FAB)m/e 285 (MH$^+$), 284 (M$^+$).

Intermediate 6: 2-[2-[4-trifluoromethylphenyl)-5-methyl-1,3-oxazol-4-yl]acetic acid methyl ester A mixture of 3.62 g (19.1 mmol) of 4-trifluoromethylbenzamide and 4.0 g (19 mmol) of methyl 4-bromo-3-oxo-pentanoate in 15 mL of toluene and 10 mL of dioxane (with 2 mL of EtOH) was refluxed for 22 h. The solution was concentrated under reduced pressure. The residue was taken into EtOAc and washed with water, brine, and dried over MgSO$_4$. The crude material was purified by silica gel chromatography (10%–40% EtOAc in hexanes) to yield 130 mg of a yellow solid: $^1$H NMR (CDCl$_3$, 400 MHz) δ8.1 (d, 2H, J=8.3), 7.65 (d, 2H, J=8.4), 3.75 (s, 3H), 3.58 (s, 2H), 2.39 (s, 3H); low resolution MS (ES$^+$) m/e 300.0 (MH$^+$).

Intermediate 7: 2-[2-(4-isopropoxyphenyl)-5-methyl-1,3-oxazol-4-yl]acetic acid ethyl ester A mixture of 2.8 g (15.6 mmol) of 4-isopropoxybenzamide and 3.26 g (15.6 mmol) of methyl 4-bromo-3-oxo-pentanoate in 10 mL of toluene and 1 mL of EtOH was refluxed for 24 h. The solvents were removed and the crude residue purified directly via silica gel chromatography (4/1 hexanes/EtOAc) to yield 1.31 g (28%) of Intermediate 6: $^1$H NMR (CDCl$_3$, 400 MHz) δ7.92 (d, 2H, J=8.9), 6.93 (d, 2H, J=8.9), 3.85 (s, 3H), 3.73 (s, 3H), 3.56 (s, 2H), 2.34(s, 3H); low resolution MS (FAB)m/e 285 (MH$^+$).

Intermediate 8: 2-[5-methyl-phenyl-1,3-oxazol-4-yl]ethanol

To a solution of 330 mg (1.43 mmol) of intermediate 1 in 5 mL of THF at 0° C. was added dropwise 1.43 mL (1.43 mmol) of 1.0 M LAH in Et$_2$O solution. The solution as stirred at 0° C. for 1 hr, quenched by the addition of 0.054 mL H$_2$O, 0.054 mL of 1.0 N NaOH solution, and 0.162 mL of H$_2$O, and MgSO$_4$ was added. The mixture was filtered, the filtrate was concentrated, and the crude oil dried under vacuum for several hours to give 280 mg of Intermediate 8 as a pale yellow-colored solid: $^1$H NMR (CDCl$_3$, 400 MHz) d 7.97 (m, 2H), 7.42 (m, 3H), 3.92 (t, 2H, J=5.6), 2.72 (t, 2H, J=5.6), 2.33 (s, 3H); low resolution MS (ES+)m/e 204 (MH$^+$); TLC R$_f$=0.21 (1/1 hexanes/EtOAc)

Intermediate 8B: 2-[5-ethyl-2-phenyl-1,3-oxazol-4-yl]ethanol

The title compound was prepared (as described above for the preparation of
Intermediate 8 from intermediate 1B (710 mg, 2.74 mmol) and 125 mg LAH to give 480 mg (81% yield) of intermediate 8B: TLC R$_f$=0.21 (2/1 hexanes/EtOAc); $^1$H NMR (CDCl$_3$, 400 MHz) δ8.0–7.97 (m, 2H), 7.46–7.41 (m, 3H), 3.92 (t, 2H, J=5.6), 3.33 (broad s, 1H), 2.75–2.66 (m, 4H), 1.27 (t, 3H), J=7.6); low resolution MS (ES$^+$)m/e 218.15 (MH$^+$).

Intermediate 8C: 2-[2-phenyl-5-propyl-1,3-oxazol-4-yl]ethanol

The title compound was prepared (as described above for the preparation of Intermediate 8) from intermediate 1C (820 mg, 3.0 mmol) and 137 mg LAH to give 360 mg (52% yield) of intermediate 8C: TLC R$_f$=0.29 (2/1 hexanes/EtOAc); $^1$H NMR (CDCl$_3$, 400 MHz) δ7.91 (m, 2H), 7.39–7.32 (m, 3H), 3.86 (t, 2H, J=5.6), 2.68–2.55 (m, 2H), 4.48–2.41 (m, 2H), 1.68–1.53 (m, 2H), 0.91 (t, 3H, J=7.6); low resolution MS (ES$^+$)m/e 232.14 (MH$^+$).

Intermediate 8D: [5-methyl-2-phenyl-1,3-oxazol-4-yl]methanol

The title compound was prepared via LAH reduction of intermediate 1D. Thus, 670 mg of Intermediate 1D (3.30 mmol) was stirred with 165 mg of LAH at 23° C. for two hours. Silica gel chromatography gave 120 mg (19% yield) of Intermediate 8D: TLC R$_f$=0.28 (2/1 hexanes/EtOAc); $^1$H NMR (CDCl$_3$, 300 MHz) δ8.0–7.97 (m, 2H), 7.49–7.41 (m, 3H), 4.59 (s, 2H), 4.18–4.05 (broad s, 1H), 2.38 (s, 3H); low resolution MS (ES$^+$)m/e 190.1 (MH$^+$).

Intermediate 8E: 3-[5methyl-2-phenyl-1,3-oxazol-4-yl]propanol

The title compound was prepared from intermediate 8 via a 1-carbon homologation sequence as follows: The mesylate (3.88 g, 1.38 mmol) of alcohol Intermediate 8 (from Et$_3$N, methanesulfonyl chloride, THF, 0° C.) was heated to 120° C. with 1.08 g (16.6 mmol) of KCN for 14 hr. Aqueous work-up and silica gel chromatography (EtOAc/hexanes) gave 860 mg (30%) of cyanide intermediate. Hydrolysis to the acid intermediate was accomplished in refluxing EtOH/water for 2.5 hrs with NaOH (650 mg). Acidification of the aqueous phase gave 580 mg (62% yield) of the acid. Reduction with LAH (95 mg, 3.0 mmol) in Et$_2$O for 3 hrs followed by silica gel chromatography provided 370 mg (68% yield) of Intermediate 8E: TLC R$_f$=0.14 (2/1 hexanes/EtOAc);$^1$H NMR (CDCl$_3$, 400 MHz) δ7.98–7.93 (m, 2H), 7.45–7.37 (m, 3H), 3.75 (t, 2H, J=8.7), 3.36 (br s, 1H), 2.64 (t, 2H, J=6.9), 2.33 (s, 3H), 1.94–1.85 (m, 2H); low resolution MS (ES$^+$)m/e 218.17 (MH$^+$).

Intermediate 8F: 3-[5-ethyl-2-phenyl-1,3-oxazol-4-yl]propanol

Intermediate 8F was prepared from intermediate 8B via a one carbon homologation procedure as described for the preparation of intermediate 8E. Thus, 495 mg of alcohol intermediate 8B was converted to intermediate 8F via mesylate (380 mg), cyanide (355 mg), and acid (280 mg) intermediates. Borane reduction (THF, 0° C., 6.5 mL of 1.0 M BH$_3$/THF complex) on 273 mg of acid intermediate gave 215 mg of alcohol intermediate 8F; $^1$H NMR (CDCl$_3$, 300 MHz) δ8.05–8.01 (m, 2H), 7.48–7.44 (m, 3H), 3.79 (t, 2H, J=5.8 ), 2.78–2.67 (m, 4H), 1.97–1.91 (m, 2H), 1.31 (t, 3H, J=7.5); low resolution MS (ES$^+$)m/e 231.91 (M$^+$); TLC R$_f$=0.49 (1/2 hexanes/EtOAc).

Intermediate 8G: [5-ethyl-2-phenyl-1,3oxazol-4-yl]methanol

Intermediate 8G was prepared (as described below for intermediate 9B) from 410 mg of intermediate 1E to give 335 mg (87%) of the title compound; $^1$H NMR (CDCl$_3$, 300 MHz) δ7.96–7.940 (m, 2H), 7.39–7.37 (m, 3H), 4.54 (s, 2H), 2.71 (q, 2H, J=7.5), 2.38 (br s, 1H), 1.25 (t, 3H, J=7.5); low resolution MS (ES$^+$)m/e 203.94 (MH$^+$).

Intermediate 9: 2-[5-methyl-2-phenyl-1,3-thiazol-4-yl]ethanol

To a 0° C. stirred solution of 6.11 g (24.7 mmol) of ester Intermediate 2 in 100 mL of THF was added 935 mg (25 mmol) of LAH. The reaction was stirred for 20 minutes at 20° C., cooled to 0° C., and quenched with water. The solids were filtered, washed with Et$_2$O, and the filtrate was dried (MgSO$_4$). Silica gel chromatography with EtOAc in hexanes (40% to 50%) gave 2.33 g (38% yield) of Intermediate 9: $^1$H NMR (CDCl$_3$, 400 MHz) δ7.85 (m, 2H), 7.42 (m, 3H), 3.99 (m, 3), 2.90 (m, 2H), 2.41 (s, 3H); low resolution MS (ES+)m/e 220.1 (MH$^+$); TLC R$_f$=0.43 (1/1 hexanes/EtOAc).

Intermediate 9B: 2-[5-ethyl-2-phenyl-1,3-thiazol-4-yl]ethanol

To a THF (15 mL) solution of 4.0 g (16.2 mmol) of intermediate 2B at 0° C. was added dropwise over 10 minutes 57 mL of 1.0 M BH$_3$-THF complex in THF. Stirred at 35–40° C. for 3 h before cooling to 0° C. and quenching with 70 mL of MeOH. Concentrated, taken into 50 mL of n-butanol and refluxed for 45 min. The solution was concentrated and the residue collected was purified by silica gel chromatography. Elution with 20–50% EtOAc in hexanes gave 2.4 g (64% yield) of a yellow viscous oil after concentration of the pooled product fractions and drying under vacuum: $^1$H NMR (CDCl$_3$, 300 MHz) δ7.86–7.83 (m, 2H), 7.41–7.34 (m, 3H), 3.96 (t, 2H, J=5.5), 2.89 (t, 2H, J=5.5), 2.77 (q, 2H, J=7.5), 1.27 (t, 3H, J=7.5).

Intermediate 9C: [5-ethyl-2-phenyl-1,3-thiazol-4-yl]methanol

Intermediate 9C was prepared (as described above for intermediate 9B) from 3.74 g of intermediate 2C to give 2.45 g (70%) of the title compound; $^1$H NMR (CDCl$_3$, 300 MHz) δ793–7.90 (m, 2H), 7.47–7.43 (m, 3H), 4.75 (s, 2H), 3.02 (br s, 1H), 2.89 (q, 2H, J=7.2), 1.35 (t, 3H, J=7.2); low resolution MS (ES$^+$)m/e 219.88 (MH$^+$).

Intermediate 10: 2-[2-(4-fluorophenyl)-5-methyl-1,3-oxazol-4-yl]ethanol

To a 0° C. stirred solution of 380 mg (1.44 mmol) of ester Intermediate 3 in 10 mL of THF was added 55 mg (1.44 mmol) of LAH. The reaction was stirred for 20 minutes at 20° C., cooled to 0° C., and quenched with saturated aqueous NH$_4$Cl solution. The solids were filtered, washed with Et$_2$O, and the filtrate was dried (MgSO$_4$). Silica gel chromatography with EtOAc/hexanes (1/2 to 2/1) as eluent gave 175 mg (55% yield) of intermediate 10: $^1$H NMR (CDCl$_3$, 400 MHz) δ7.96 (m, 2H), 7.12 (m, 2H), 3.92 (d, 2H, J=5.0), 3.21 (s, 1H), 2.71 (t, 2H, J=5.6), 2.32 (s, 3H); low resolution MS (FAB)m/e 221 (M$^+$); TLC R$_f$=0.20 (1/1 hexanes/EtOAc).

Intermediate 10B: 2-[5-ethyl-2-(4-fluorophenyl)-1,3-oxazol-4-yl]ethanol

The title compound was prepared as described above for example 9B. From 1.3 g of intermediate 3B was prepared 1.14 g (94%) of intermediate 10B as a yellow-colored, viscous oil; $^1$H NMR (CDCl$_3$, 400 MHz) δ7.98–7.94 (m, 2H), 7.10 (t, 2H, J=8.7), 3.89 (t, 2H, J=5.6), 2.71 (t, 2H, J=5.7), 2.66 (t, 2H, J=7.5), 1.25 (t, 3H, J=7.5); low resolution MS (ES+)m e 236.17 (MH$^+$); TLC R$_f$=0.37 (1/1 hexanes/EtOAc)

Intermediate 10C: 3-[5-ethyl-2-fluorophenyl)-1,3-oxazol-4-yl]propanol

Intermediate 10C was prepared from intermediate 10B via a one carbon homologation procedure as described for the preparation of intermediate 8E. Thus, 720 mg of alcohol intermediate 10B was converted to intermediate 10C via mesylate (828 mg), cyanide (495 mg), and acid (440 mg) intermediates. Borane reduction (THF, 0° C. 6.5 mL of 1.0 M BH$_3$/THF complex) instead of LAH reduction on 430 mg of acid intermediate gave 320 mg of alcohol intermediate 10C; $^1$H NMR (CDCl$_3$, 400 MHz) δ7.98–7.93 (m, 2H), 7.09 (t, 2H, J=8.6), 3.72 (t, 2H, J=5.8), 2.70–2.56 (m, 4H), 1.91–2H), 1.24 (t, 3H, J=7.5); low resolution MS (ES+)m/e 250.15 (MH$^+$); TLC R$_f$0.55 (1/2 hexanes/EtOAc).

Intermediate 10D: [5-ethyl-2-(4-fluorophenyl)-1,3-oxazol-4-yl]methanol

The title compound was prepared as described above for example 9B. From 1.52 g of intermediate 3C was prepared 735 mg (51%) of intermediate 10D; $^1$H NMR (CDCl$_3$, 300 MHz) δ8.05–8.04 (m, 2H), 7.18–7.16 (m, 2H), 4.64 (s, 2H), 2.82–2.78 (m, 2H), 2.30 (br s, 1H), 1.35–1.31 (m, 3H); low resolution MS (ES+)m/e 221.94 (MH$^+$); TLC R$_f$=0.60 (1/2 hexanes/EtOAc).

Intermediate 11: 2-[2-(4-fluorophenyl)-5-methyl-1,3-thiazol-4-yl]ethanol

The title compound was prepared from crude ester Intermediate 4 and 1.07 g of LAH as described above for the preparation of Intermediate 10 to yield 2.8 g of Intermediate 11 (21% yield over two steps, preparation of Intermediates 4 plus 11): $^1$H NMR (CDCl$_3$, 400 MHz) δ7.96 (m, 2H), 7.12 (m, 2H), 3.92 (d, 2H, J=5.0), 3.21 (s, 1 H), 2.71 (t, 2H, J=5.6), 2.32 (s, 3H); resolution MS (FAB)m/e 221 (M$^+$).

Intermediate 11B: 2-[5-ethyl-2-(4-fluorophenyl)-1,3-thiazol-4-yl]ethanol

The title compound was prepared as described above for example 9B. From 2.7 g of intermediate 4B was prepared 1.75 g (68%) of intermediate 11B as a colorless, viscous oil; $^1$H NMR (CDCl$_3$, 400 MHz) δ7.85–7.80 (m, 2H), 7.07 (t, 2H, J=8.7), 3.95 (t, 2H, J=5.6), 2.88 (t, 2H, J=5.5), 2.77 (q, 2H, J=7.5), 1.27 (t, 3H, J=7.5); low resolution MS (ES+)m/e 252.17 (MH$^+$); TLC R$_f$=0.47 (1/1 hexanes/EtOAc)

Intermediate 12: 2-[24(4-methoxyphenyl)-5-methyl-1,3-oxazol-4-yl]ethanol

To a stirring solution of 185 mg (0.71 mmol) of Intermediate 42 in 5 mL of THF at 0° C. was added 0.71 mL (0.71 mmol, 1.0 equiv) of a 1.0 M solution of LiAlH$_4$ in THF. The resulting solution was stirred at RT for 45 min then cooled to 0° C. and quenched by careful addition of 0.027 mL of H$_2$O, followed by addition of 0.027 mL of 15% NaOH and 0.080 mL of H$_2$0. The resulting slurry was filtered to remove the solids and the filtrate was concentrated under reduced pressure to afford 164 mg of the title compound as a light yellow oil: $^1$H NMR (CDCl$_3$, 400 MHz) δ7.92 (d, 2H, J=8.8), 6.94 (d, 2H, J=8.8), 3.92 (dt, 2H, J=5.7, 11.5), 3.86 (s, 3H), 3.35 (t, 1H, J=6.2), 2.71 (t, 2H, J=5.7) 2.32 (s, 3H).

Intermediate 13: 2-[2-(4-trifluoromethylphenyl)-5-methyl-1,3-oxazol-4-yl]ethanol The title compound was prepared from 390 mg of ester Intermediate 6 (as described above for the preparation of Intermediate 10) to yield 170 mg of Intermediate 13: TLC R$_f$=0.24 (1/1 hexanes/EtOAc), $^1$H NMR (400 MHz, CDCl$_3$) δ8.08 (d, 2H, J=8.2), 7.68 (d, 2H, J=8.4), 3.93 (q, 2H, J=11.4, 5.8), 2.99 (t, 1H, J=6.0), 2.74 (t, 2H, J=5.8), 1.56 (s, 3H).

Intermediate 14: 2-[2-(4-isopropoxyphenyl)-5-methyl-1,3-oxazol-4-yl]ethanol

The title compound was prepared from 1.3 g of ester Intermediate 7 (as described above for the preparation of Intermediate 10) to yield 540 mg of Intermediate 14: TLC R$_f$=0.21 (1/1 hexanes/EtOAc), $^1$H NMR (400 MHz, CDCl$_3$) δ7.87 (d, 2H, J=8.8), 6.9 (d, 2H, J=9.0), 4.6 (hept, 1H, J=6.0), 3.9 (q, 2H, J=11.4, 5.7), 3.35 (t, 1H, J=6.0), 2.69 (t, 2H, J=5.6), 2.3 (s, 3H), 1.35 (d, 6H, J=6.0).

Intermediate 15: 5-[24(methanesulfonyloxy)ethyl]-4-methyl-2-phenyl-1,3-oxazole

To a solution of 9.41 g (46.3 mmol) of alcohol Intermediate 8 in CH$_2$Cl$_2$ (300 mL) at 0° C. was added 3.94 mL (50.9 mmol) of methanesulfonyl chloride followed by 7.75 mL (55.6 mmol) of triethylamine. After 1 hr with gradual warming to 20° C., the solution was washed with water (3×), brine (1×), and dried over MgSO$_4$. Concentration gave 12.92 g (99%) of Intermediate 15 homogeneous by TLC analysis: (R$_f$=0.24, 1/1 hexanes/EtOAc); $^1$H NMR (CDCl$_3$, 400 MHz) d 7.97 (m, 2H), 7.43 (m, 3H), 4.53 (t, 2H, J=6.5), 2.95 (s, 3H), 2.95 (t, 2H, J=6.5), 2.36(s, 3H); low resolution MS (ES+)m/e 281.9 (MH$^+$); TLC R$_f$=0.35 (1/1 hexanes/EtOAc)

Intermediate 16: 1 (phenyl)-1,3-pentanedione

The title compound was prepared according to Popio, V. V. et al. *Synthesis* (March 1991), pp 195–197. To a stirred suspension of NaH (1.2 g, 50 mmol) and ethyl propionate (5.73 mL. 50 mmol) in 20 mL THF at 20° C. was added EtOH (2 drops), acetophenone (3.0 g, 25 mmol) in 20 mL of THF, and dibenzo-18-crown-6 (150 mg, 0.4 mmol) in 20 mL of THF. Stirred for 30 min, then at reflux for 1 hr. Cooled (0° C.), then added 25 mL of 10% H$_2$SO$_4$ solution and the aqueous was extracted with Et$_2$O. The organics were washed with H$_2$O, aqueous Na$_2$CO$_3$, and brine. The solution was dried over Na$_2$SO$_4$ and concentrated. Purification by silica gel chromatography (1% to 10% EtOAc in hexanes) gave 4.0 g of Intermediate 16 as a thin oil. $^1$H NMR indicated an ~10:1 mixture of tautomers favoring the enol form: $^1$H NMR (400 MHz, CDCl$_3$, enol form) δ7.87 (m, 2H), 7.52–7.4 (m, 3H), 6.17 (s, 1H), 2.47 (q, 2H, J=7.5), 1.21 (t, 3H, J=7.5)

Intermediates 17,18, and 20–33 were prepared analogous to the method described above for the preparation of Intermediate 16.

Intermediate 17: 1-phenyl-1,3-hexanedione

The title compound was prepared (as described above for Intermediate 16) from 3.0 g of acetophenone and 5.8 g of ethyl butyrate to yield 4.0 grams of Intermediate 17 as an oil: TLC R$_f$=0.51 (1/9 EtOAc/Hexanes); $^1$H NMR (400 MHz, CDCl$_3$) δ7.88 (m, 2H), 7.48 (m, 3H), 6.17 (s, 1H), 2.4 (t, 2H, J=7.6), 1.72 (q, 2H, J=7.6), 1.0 (t, 3H, J=7.2); low resolution MS (ES+)m/e 213.0 (M+Na$^+$).

Intermediate 18: 1-(phenyl)-1,3-heptanedione

The title compound was prepared (as described above for Intermediate 16) from 2.2 g (18.3 mmol) of acetophenone and 4.51 g (35 mmol) of ethyl valerate to yield 2.6 grams of Intermediate 18:: TLC R$_f$=0.52 (1/9 EtOAc/Hexanes); $^1$H NMR (400 MHz, CDCl$_3$) δ7.87 (m, 2H), 7.48 (m, 3H), 6.17 (s,1H), 2.42 (t, 2H, J=7.6), 1.67 (m, 2H), 1.4 (m, 2H), 0.95 (t, 3H, J=7.2); low resolution MS (ES+)m/e 205.1 (MH+), 227.1 (M+Na$^+$).

Intermediate 19: 1(phenyl)-1,3decanedione

To a solution of 1 g (6.1 mmol) of benzoylacetone in 6 mL of THF at −78° C. was added 8.2 mL (12.3 mmol) of a 1.5 M LDA solution in THF. Warmed to 0° C. over 2 h, then 2.6 mL (12.3 mmol) of 1-iodohexane was added. The mixture was stirred at rt for 3 h before quenching with saturated aqueous NH$_4$Cl solution and dilution with Et$_2$O. The organics were dried (Na$_2$SO$_4$), filtered, concentrated, and purified by silica gel chromatography (15/1 hexanes/Et$_2$O) to yield Intermediate 19: TLC R$_f$=0.52 (1/10 Et$_2$O/Hexanes); $^1$H NMR (400 MHz, CDCl$_3$, enol form) δ7.88 (m, 2H), 7.54–7.43 (m, 3H), 6.17 (s, 1H), 2.42 (t, 2H, J=7.6), 1.66 (m, 2H), 1.4–1.25 (m, 8H), 0.85 (m, 3H); low resolution MS(ES+) m/e 269.0 (M+Na$^+$).

Intermediate 20: 1 (2-Fluorophenyl)-1,3-butanedione

The title compound was prepared (as described above for Intermediate 16) from 2.0 g of 2'-fluoroacetophenone and 2.86 mL of EtOAc to yield Intermediate 20: $^1$H NMR (400 MHz, CDCl$_3$, enol form) δ7.70 (dt, 1H. J=1.79, 7.69), 7.45 (m, 1H), 7.24 (m, 1H), 7.10 (m, 1H), 6.28 (s, 1H), 2.20 (s, 3H).

Intermediate 21: 1(3methylphenyl)-1,3-butanedione

The title compound was prepared (as described above for Intermediate 16) from 2.72 mL of 3'-methylacetophenone and 3.95 mL of EtOAc to yield 2.94 grams of Intermediate 21 as an oil: $^1$H NMR (400 MHz, CDCl$_3$ enol form) δ7.70 (m, 2H), 7.34 (m, 2H), 6.17 (s, 1H), 2.41 (s, 3H), 2.20 (s, 3H); low resolution MS (ES)m/e 177.1 (MH$^+$).

Intermediate 22:1-(4-methoxyphenyl)-1,3-butanedione

The title compound was prepared (as described above for Intermediate 16) from 3.0 g of 4'-methoxyacetophenone and 3.95 mL of EtOAc. Purification by recrystallization from toluene/hexane afforded the title compound: $^1$H NMR (400 MHz, CDCl$_3$, enol form) δ7.70 (d, 2H, J=8.20), 7.34 (d, 2H, J=8.20), 6.17 (s, 1H), 3.87 (s, 3H), 2.17 (s, 3H); low resolution MS (ES)m/e 193.1 (MH$^+$)

Intermediate 23: 142-hydroxyphenyl)-1,3-butanedione

The title compound was purchased from Aldrich Chemical Co.

Intermediate 24: 1-(4-trifluoromethylphenyl)-1,3-butanedione

The title compound was prepared (as described above for Intermediate 16) from 51.43 g of 4'-trifluoroacetophenone and 53.4 mL of EtOAc to yield 35.78 g of Intermediate 24: TLC analysis: R$_f$=0.70 (2/1, hexanes/EtOAc), $^1$H NMR (400 MHz, CDCl$_3$, enol form) δ7.96 (d, 2H, J=7.0), 7.7 (d, 2H, J=7.0), 6.2 (s, 1H), 2.23 (s, 3H).

Intermediate 25: 144-trifluoromethylphenyl)-1,3-pentanedione

The title compound was prepared (as described above for Intermediate 16) from 1.5 g of 4'-trifluoromethylacetophenone and 1.54 mL of methyl propionate to yield 0.69 g of intermediate 25: TLC analysis: R$_f$=0.75 (2/1, hexanes/EtOAc), $^1$H NMR (400 MHz, CDCl$_3$, enol form) δ7.92–7.86 (m, 2H), 7.12 (t, 2H, J=8.6), 6.1 (s, 1H), 2.45 (q, 2H, J=7.5), 1.21 (t, 3H, J=7.5).

Intermediate 26: 1-4(4-Fluorophenyl)-1,3-butanedione

The title compound was prepared (as described above for Intermediate 16) from 2.42 mL of 4'-fluoroacetophenone and 3.95 mL of EtOAc to yield Intermediate 26 as an oil: $^1$H NMR (400 MHz, CDCl$_3$, enol form) δ7.89 (dd, 2H, J=8.90, 5.40), 7.13 (dd, 2H, J=17.2, 8.60), 6.13 (s, 1H), 2.19 (s, 3H).

Intermediate 27: 1-(4-methylphenyl)-1,3-butanedione

The title compound was prepared (as described above for Intermediate 16) from 2.0 g of 4'-methylacetophenone and 2.9 mL of EtOAc to yield 1.68 grams of Intermediate 27: TLC analysis: R$_f$=0.61 (5/1, hexanes/EtOAc), $^1$H NMR (400 MHz, CDCl$_3$, enol form) δ7.72 (d, 2H, J=8.2), 7.24 (d, 2H, J=7.4), 6.15 (s, 1H), 2.4 (s, 3H), 2.2 (s, 3H).

Intermediate 28: 1-(4-chlorophenyl)-1,3-butanedione

The title compound was prepared (as described above for Intermediate 16) from 2.0 g of 4'-chlorophenone and 2.53 mL of EtOAc to yield 1.7 grams of Intermediate 28: TLC analysis: $R_f$=0.73 (2/1, hexanes/EtOAc); $^1$H NMR (400 MHz, CDCl$_3$, enol form) δ7.82 (d, 2H, J=8.0), 7.42 (d, 2H, J=8.0), 6.13 (s, 1H), 2.2 (s, 3H).

Intermediate 29: 1(4-isopropoxyphenyl)-1,3-butanedione

The title compound was prepared (as described above for Intermediate 16) from 2.42 g of 4'-isopropoxyacetophenone and 2.65 mL of EtOAc to yield 2.25 grams of Intermediate 29: TLC analysis: $R_f$=0.73 (2/1, hexanes/EtOAc); $^1$H NMR (400 MHz, CDCl$_3$, enol form) δ7.84 (d, 2H, J=8.9), 6.9 (d, 2H, J=9.0), 6.1 (s, 1H), 4.62 (hept, 1H, J=6.0), 2.16 (s, 3H), 1.36 (d, 6H, J=6.0).

Intermediate 30:1-(2-chlorophenyl)-1,3-butanedione

The title compound was prepared (as described above for Intermediate 16) from 2.0 g of 2'-chloroacetophenone and 2.53 mL of EtOAc to yield 0.5 g of Intermediate 30: TLC analysis: $R_f$=0.76 (2/1, hexanes/EtOAc); $^1$H NMR (400 MHz, CDCl$_3$, enol form) δ7.6–7.55 (m, 1H), 7.45–7.43 (m, 1H), 7.4–7.32 (m, 1H), 6.05 (s, 1H), 2.18 (s, 3H).

Intermediate 31: -(1,3-thienyl)-1,3-butanedione

The title compound was prepared (as described above for Intermediate 16) from 1.5 g of 3-acetylthiophene and 2.32 mL of EtOAc to yield 1.28 grams of Intermediate 31 as a yellow oil: TLC $R_f$=0.65 (2/1, hexanes/EtOAc); $^1$H NMR (400 MHz, CDCl$_3$, enol form major, ~85:15) δ8.0 (m, 1H), 7.45 (m, 1H), 7.35 (m, 1H), 6.0 (s, 1H), 2.18 (s, 3H).

Intermediate 32: -(4-Fluorophenyl)-1,3-pentanedione

The title compound was prepared (as described above for Intermediate 16) from 0.525 g of 4'-fluoroacetophenone and 0.73 mL of methyl propionate to yield 120 mg of Intermediate 32: TLC analysis: $R_f$=0.77 (2/1, hexanes/EtOAc); $^1$H NMR (400 MHz, CDCl$_3$, enol form) δ7.98 (d, 2H, J=8.3), 7.7 (d, 2H, J=8.3), 6.12 (s, 1H), 1.55 (s, 3H); low resolution mass spectrum (ES+) 195 (MH+)

Intermediate 33: -(4cyclohexyl)-1,3-butanedione

The title compound was prepared as described above from 1.5 g of cyclohexyl methyl ketone and 2.32 mL of EtOAc to yield 1.06 grams of Intermediate 33 as a yellow oil: TLC $R_f$=0.65 (3/1, hexanes/EtOAc); $^1$H NMR (400 MHz, CDCl$_3$, enol form) δ5.5 (s, 1H), 2.19–2.12 (m, 1H), 2.08 (s, 3H), 1.85–1.55 (m, 5H), 1.41–1.15 (m, 5H).

Intermediate 34: 1-(2-pyrazinyl)-1,3-butanedione

To a solution of methyl 2-pyridazinecarboxylate (1.5 g, 10.86 mmol) in 3 mL of acetone and 10 mL of THF was slowly added 590 mg (10.86 mmol) of NaOMe and the resulting mixture was refluxed for 4 hr. The mixture was filtered, the filtrate was acidified and extracted with CH$_2$Cl$_2$, and the organics 10 were dried over MgSO$_4$ to yield 940 mg (53%) homogeneous by TLC: $R_f$=0.5 (2/1, EtOAc/hexanes); $^1$H NMR (400 MHz, CDCl$_3$, enol form) δ9.27 (d, 1H, J=1.4), 8.7 (d, 1H, J=2.4), 8.6 (t, 1H, J=1.8), 2.26 (s, 3H).

Intermediate 35: 1-(2-pyridinyl)-1,3-butanedione

Intermediate 36 was prepared as described above for Intermediate 35 from 2.0 g of methyl 2-pyridylcarboxylate and 4.0 mL of acetone to yield 1.08 g of the title compound (45% yield) as a light brown oil: TLC analysis: $R_f$=0.73 (2/1, hexanes/EtOAc); $^1$H NMR (400 MHz, CDCl$_3$, mixture of enol/non-enol forms ~80/20) δ8.66 (m, 1H), 8.05 (m, 1H), 7.85 (m, 1H), 7.46 (m, 1H), 6.8 (s, 1H), 2.24 (s, 3H), (non-enol form singlets observed at 4.28 and 2.35).; low resolution mass spectrum (ES+) 164.1 (MH+).

Intermediate 36: 1-(2,3,4-trifluorophenyl)-2-butyn-1-one

Propynyllithium (720 mg, 14.05 mmol) was added to a 0° C. stirred solution of 1.5 g (9.37 mmol) of 2,3,4-trifluorobenzaldehyde and the solution was allowed to stir for 1 h with warming to ambient temperature. The solution was diluted with EtOAc and washed with H$_2$O and brine. The organics were dried over MgSO$_4$ and concentrated (yield of intermediate alcohol, 1.88 g). The crude product was stirred in 30 mL of CH$_2$Cl$_2$ with 4 g of activated MnO$_2$ at 20° C. for 2.5 h. The mixture was filtered through a pad of celite/silica gel and concentrated to yield 1.31 g (47% overall yield) of crude product homogeneous by TLC analysis: $R_f$=0.6 (2/1, hexanes/EtOAc); $^1$H NMR (300 MHz, CDCl$_3$) δ7.9–7.8 (m, 1H), 7.1–6.95 (m, 1H), 2.13 (s, 3H).

Intermediates 37–43 were prepared analogous to the method described above for the preparation of Intermediate 36.

Intermediate 37:1-(2-fluoro-3-trifluoromethylphenyl)-1,3-pentanedione

The title compound was prepared (as described above for intermediate 36) from 0.5 g of 2'-fluoro-3'-trifluoromethylbenzaldehyde and 1.03 g of MnO$_2$ to yield 0.46 g (75% overall yield) of Intermediate 37: $^1$H NMR (400 MHz, CDCl$_3$) δ8.19 (m, 1H), 7.84 (m, 1H), 7.32 (m,$_1$H), 2.1 (s, 3H).

Intermediate 38: 1-(2,4,5-trifluorophenyl)-2-butyn-1-one

Intermediate 38 was prepared (as described above for intermediate 36) from 1-propynyllithium, 0.5 g of 2',4',5'-trifluorobenzaldehyde, and 0.87 g of MnO$_2$ to yield 0.39 g (63% overall yield) of the title compound: $^1$H NMR (400 MHz, CDCl$_3$) δ7.91–7.82 (m, 1H), 7.05–6.96 (m, 1H), 2.14 (s, 3H). For the alcohol intermediate; $^1$H NMR (400 MHz, CDCl$_3$) δ7.54–7.48 (m, 1H), 6.97–6.88 (m, 1H), 5.64 (s, 1H), 1.91 (s, 3H).

Intermediate 39: 1-(2,4-difluorophenyl)-2-butyn-1-one

Intermediate 39 was prepared as described above for intermediate 36) from 1-propynyllithium, 500 mg of 2',4'-difluorobenzaldehyde, and 1.5 g of MnO$_2$ to yield 400 mg of the title compound homogeneous by TLC ($R_f$=0.63, 2/1 hexanes/EtOAc); $^1$H NMR (400 MHz, CDCl$_3$) δ8.13–8.06 (m, 1H), 6.99–6.94 (m, 1H), 6.91.6.85 (m, 1H), 2.14 (s, 3H).

Intermediate 40: 1-(2,3-difluorophenyl)-2-butyn-1-one

Intermediate 40 was prepared as described above for intermediate 36) from 1-propynyllithium, 500 mg of 2,3-difluorobenzaldehyde, and 1.5 g of MnO$_2$ to yield 440 mg of the title compound homogeneous by TLC ($R_f$=0.5, 2/1 hexanes/EtOAc); $^1$H NMR (400 MHz, CDCl$_3$) δ7.82–7.86 (m, 1H), 7.43–7.35 (m 1H), 7.22–7.15 (m, 1H), 2.15 (s, 3H).

Intermediate 41: 1-(4-nitrophenyl)-2-butyn-1-one

Intermediate 41 was prepared (as described above for intermediate 36) from 1-propynyllithium, 1.0 gram of 4'-nitrobenzaldehyde, and 1.0 g of $MnO_2$ to yield 430 mg of the title compound homogeneous by TLC analysis: $R_f$=0.55 (2/1, hexanes/EtOAc), $^1$H NMR (400 MHz, $CDCl_3$) δ8.32–8.28 (m, 4H), 2.12 (s, 3H).

Intermediate 42: 1-(3-nitrophenyl)-2-butyn-1-one

Intermediate 42 was prepared (as described above for Intermediate 36) from 1-propynyllithium and 0.5 g of 3'-nitrobenzaldehyde and 1.5 g $MnO_2$ to yield 280 mg of the title compound: TLC analysis: $R_f$=0.50 (2/1, hexanes/EtOAc), $^1$H NMR (400 MHz, $CDCl_3$) δ8.95 (t, 1H, J=1.8), 8.47 (t, 1H, J=1.7), 8.44 (t, 1H, J=1.7), 7.7 (t, 1H, J=8.0), 2.23 (s, 3H).

Intermediate 43: 1-(2-thiazolyl)-2-butyn-1-one

Intermediate 43 was prepared (as described above for Intermediate 36) from 1-propynyllithium, 2-thiophene carboxaldehyde (108 mg) and 300 mg of $MnO_2$ to yield 65 mg of the title compound : TLC analysis: $R_f$=0.50 (1/1, hexanes/EtOAc); $^1$H NMR (400 MHz, $CDCl_3$) δ8.1 (d, 1H, J=2.8), 7.71 (d, 1H, J=2.9), 2.21 (s, 3H); low resolution mass spectrum (ES+) 152.1 (MH+).

Intermediate 44: 3-Bromo-4,4,4-trifluoro-1-phenylbut-2-en-1-one (mixture of E- and Z-isomers, ~85:15)

To a solution of 7.58 g (28.9 mmol) of triphenylphosphine in 60 mL of $CH_2Cl_2$ at 0° C. was added 1.49 mL (28.9 mmol) of bromine dropwise. The solution was warmed to ambient temperature and 5.0 g (23.1 mmol) of trifluoroacetyl-acetophenone in 25 mL $CH_2Cl_2$ and 6.45 mL (46.3 mmol) of triethylamine were added. The mixture was stirred for two hours until no further change was observed by TLC analysis (3/1 hexanes/EtOAc). The mixture was washed with 1.0 N HCl, $H_2O$, and brine. The organics were dried over $MgSO_4$, concentrated, and the residue purified by silica gel chromatography (20/1 hexanes/EtOAc) to give 1.6 g of impure material and 1.15 g (25% yield) of Intermediate 44 as an oil: TLC $R_f$=0.74 (3/1, hexanes/EtOAc); $^1$H NMR (400 MHz, $CDCl_3$) δ7.95–7.5 (series of multiplets, 5H); $^{19}$F NMR (282 MHz, $CDCl_3$) singlet, δ–100.5 ppm)

Intermediate 45: (2S)-2-amino-3-{4-[2-(5-methyl-2-phenyl-1,3-oxazol-4-yl)ethoxy]phenyl}propanoic acid Dianion coupling method: To a solution of 5.4 g (19.3 mmol) of N-(Boc)-L-Tyrosine in 5 mL of DMSO and 10 mL of $H_2O$ was added 1.7 g (42.5 mmol) of freshly ground NaOH pellets. The mixture was heated to 55–60° C. and a solution of 6.5 g (23.1 mmol) of mesylate intermediate 15 in 10 mL of DMSO was added dropwise over ~5 min. The resulting mixture was stirred vigorously for 8 hr at 55–60° C., cooled to 20° C., and poured into 100 mL of $H_2O$ and extracted with $Et_2O$ (2×50 mL). The aqueous phase was separated and acidified to pH~2–3 with glacial acetic acid/HCl. The resulting slurry was extracted with EtOAc several times, dried ($MgSO_4$), and the organics were concentrated to a tan oil. The oil was triturated with hexanes/EtOAc (3/1) to give a cream-colored solid. This solid was recrystallized from hot $MeOH/H_2O$ (2.5/1) to yield 5.5 g (61% yield) of Boc-protected intermediate as a white solid after drying in a vacuum oven at 60° C. for ~14 hr. To a solution of 43.54 g (93.3 mmol) of the above Boc-protected intermediate in 150 mL of dioxane was added 200 mL of 4.0 N HCl in dioxane solution and the mixture was stirred over 7 hr with the gradual formation of a white solid. The solids were filtered (rinsing with $Et_2O$), suspended into 1 L of $H_2O$, and the pH was adjusted to pH~5 with 15% NaOH. The resulting white solids were collected via filtration, washed with $H_2O$ and $CH_3CN$, and dried overnight at 70° C. in a vacuum oven to give 32.9 g (96%) of intermediate 45 as a white solid: $^1$H NMR (DMSO-$d_6$, 300 MHz) δ7.95 (m, 2H), 7.55 (m, 3H), 7.22 (d, 2H, J=8.5), 6.9 (d, 2H, J=8.5), 4.21 (t, 2H, J=6.4), 3.1 (dd, 1H, J=14.3, 4.1), 4.17 (m, 1H), 2.96 (t, 2H, J=6.6), 2.83 (dd, 1H, J=14.3, 8.4), 2.53 (s, 3H), α-methine proton assumed under $H_2O$ peak:; low resolution MS (ES+)m/e 367.4 (MH+);

Alternative Mitsunobu Coupling Method

To a solution of 4.46 g (21.9 mmol) of alcohol Intermediate 8, 5.88 g (19.9 mmol) of N-Boc-L-tyrosine methyl ester, and 6.26 g (23.9 mmol) of triphenylphosphine in 150 mL of toluene at 45° C. was added dropwise a solution of 3.81 g (21.9 mmol) of DEAD in 50 mL of toluene. The resulting clear solution was stirred at 20° C. for 8 hr, concentrated, and the residue re-dissolved into $Et_2O$ (200 mL). To this was added 75 mL of 1 N NaOH solution. The mixture was rapidly stirred for 30 min until phenol no longer present by TLC. The aqueous phase was extracted with EtOAc and the combined organics were dried ($MgSO_4$) and concentrated. The crude tan-colored solid lo was purified by silica gel chromatography ($CH_2Cl_2/Et_2O$, 12/1 to 8/1) to give an impure product. A second column eluting with $CH_2Cl_2$/hexane (4/1), $CH_2Cl_2$, and $CH_2Cl_2/Et_2O$ (10/1) gave 5.5 g (57% yield) of a clear yellow oil. To this oil in 150 mL of THF was added dropwise 13.7 mL of 1.0 M LiOH in $H_2O$ solution. To this was added an additional 75 mL of THF and 5 mL of MeOH to give a clear solution. The solution was stirred at 20° C. and the progress of the reaction was monitored by TLC ($CHCl_3$/MeOH, 9/1). The THF was removed at reduced pressure and the aqueous phase extracted with EtOAc/1.0 N HCl. The organics were washed with $H_2O$, dried over $MgSO_4$, concentrated, and the resulting crude oil was purified by silica gel chromatography (EtOAc/hexanes, 1/1 to 8/1 gradient) to give 3.22 g (61%) of a foam. To this foam in 15 mL of dioxane was added dropwise 15 mL of 4.0 N HCl in dioxane solution at 20° C. Stirred the mixture for 4 hr producing a white solid precipitate. The solids were filtered washing with $Et_2O$, then dissolved into $H_2O$ and the pH adjusted down to ~pH 5 with the dropwise addition of 1.0 N NaOH solution. The resulting white precipitate was collected by filtration and dried in a vacuum oven at 60° C. overnight to yield 1.72 g of Intermediate 45 as a white solid.

Intermediate 46: (2S)-2-amino-3-(4-{2-[2-(4-fluorophenyl)-5-methyl-1,3-oxazol-4-yl]ethoxy}phenyl)propanoic acid DEAD (1.26 mL, 8.16 mmol) was added dropwise to a solution of 2.14 g (8.16 mmol) of triphenylphosphine in 16 mL of THF at 0° C. This solution was then added to a mixture of 2.41 g (8.16 mmol) of N-(Boc)-L-Tyrosine methyl ester (see, e.g., A. Kolodziejczyl, et al., J. Org. Chem., 46(9), pp 1944–1946 (1981)) and Intermediate 9 in 16 mL of THF at 0° C. The solution was stirred at 20° C. for 20 h and concentrated to an oil. The crude material was purified by silica gel chromatography (4:1 hexanes:EtOAc) to yield 2.78 grams (69% yield) of the protected amino acid Intermediate. Deprotection was achieved as follows: Ester hydrolysis—To a solution of 2.77 g (5.58 mmol) of the above ester in 45 mL of THF and 15 mL of $H_2O$ at 0° C. was added 8.5 mL (8.5 mmol) of 1.0 M aqueous LiOH solution. After 2 h at 20° C., EtOAc was added and the mixture was acidified with 0.1 N HCl. The aqueous was extracted with EtOAc and the organics were dried (MgSO$_4$) and concentrated to give a white glass-like solid (2.67 g). Boc Deprotection—The solid from the ester hydrolysis above (2.64 g, 5.47 mmol) was taken into 60 mL CH$_2$Cl$_2$ and treated with 30 mL of TFA with stirring for 1 h. The solution was concentrated, the residue was dissolved into ~400 mL of H$_2$O, and the pH was adjusted to is ~pH 7 with aqueous 1.0 N NaOH solution. The suspension was filtered and the collected solids were dried for 48 h at 70° C. under vacuum to yield 1.61 g (77% yield for deprotection, 53% overall yield) of Intermediate 46 as a fluffy beige-colored solid: $^1$H NMR (DMSO-d$_6$, 300 MHz) δ7.93 (dd, 2H, J=8.7, 5.4), 7.3 (t, 2H, J=8.7), 7.12 (d, 2H, J=8.0), 6.83 (d, 2H, J=8.2), 4.15 (t, 2H, J=6.5), 3.02 (dd, 1H, J=14.2, 4.3), 2.89 (t, 2H, J=6.5), 2.76 (dd, 1H, J=8.2), 2.34 (s, 3H); low resolution MS (ES+)m/e 384.9 (MH$^+$).

Intermediates 47–51 were prepared analogous to the method described above for the preparation of Intermediate 46

Intermediate 47: (2S)-2-amino-3{4-[2(5-methyl-2-phenyl-1,3-thiazol-4-yl)ethoxy]phenyl}propanoic acid Intermediate 47 was prepared from 2.41 g of N-(Boc)-L-Tyrosine methyl ester and 1.79 g of Intermediate 10 to yield 1.61 g (51% overall yield) of the title compound as a solid: $^1$H NMR (DMSO-d$_6$, 400 MHz) δ7.82 (d, 2H, J=7.5), 7.42 (m, 3H), 7.12 (d, 2H, J=8.2), 6.82 (d, 2H, J=8.4), 4.23 (t, 2H, J=6.6), 3.1 (t, 2H, J=6.6), 2.83 (dd, 1H, J=14.1, 3.7), 2.53 (s, 3H), second proton of methylene assumed under H$_2$O peak; low resolution MS (ES+)m/e 383.1 (MH$^+$);

Intermediate 48: (2S)-2-amino-3-(4-{2-[2-(4-fluorophenyl)-5-methyl-1,3-thiazol-4-yl]ethoxy}phenyl)propanoic acid Intermediate 48 was prepared from 224 mg of N-(Boc)-L-Tyrosine methyl ester and 180 mg of Intermediate 11 to yield 149 mg (51% overall yield) of the title compound as a solid: $^1$H NMR (DMSO-d$_6$, 400 MHz) δ7.82 (dd, 2H, J=8.6, 5.5), 7.23 (t, 2H, J=8.7), 7.08 (d, 2H, J=8.4), 6.8 (d, 2H, J=8.5), 4.56 (br s, 1H), 4.19 (t, 2H, J=6.5), 3.56 (m, 1H), 3.03 (t, 2H, J=6.6), 2.95 (m, 1H), 2.79 (dd, 1H, J=14.5, 7.5), 2.37 (s, 3H); low resolution MS (ES+)m/e 400.9 (MH$^+$).

Intermediate 49: (2S)-2-amino-3-(4-{2-[2-methoxyphenyl)-5-methyl-1,3-oxazol-4-yl]ethoxy}phenyl)propanoic acid Intermediate 49 was prepared from 735 mg of N-(Boc)-L-Tyrosine methyl ester and 580 mg of Intermediate 12 to yield 220 mg (22% overall yield) of the title compound as a solid. $^1$H NMR (DMSO-d$_6$, 400 MHz) δ8.16 (d, 2H, J=8.2), 7.92 (d, 2H, J=8.4), 7.21 (d, 2H, J=8.5), 6.93 (d, 2H, J=8.5), 4.25 (t, 2H, J=6.5), 3.1 (dd, 1H, J=14.4, 4.8), 3.0 (t, 2H, J=6.5) 2.76 (dd, 1H, J=14.4, 7.9), 2.46 (s, 3H); low resolution MS (ES+)m/e 434.9 (MH$^+$).

Intermediate 50: (2S)-2-amino-3-[4-(2-{5-methyl-2-[4-(trifluoromethyl)phenyl]-1,3oxazol-4-yl}ethoxy)phenyl]propanoic acid Intermediate 50 was prepared from 185 mg of N-(Boc)-L-Tyrosine methyl ester and 170 mg of Intermediate 13 to yield 130 mg (48% overall yield) of the title compound as a solid: $^1$H NMR (DMSO-d$_6$, 400 MHz) δ8.16 (d, 2H, J=8.2), 7.92 (d, 2H, J=8.4), 7.21 (d, 2H, J=8.5), 6.93 (d, 2H, J=8.5), 4.25 (t, 2H, J=6.5), 3.1 (dd, 1H, J=14.4, 4.8), 3.0 (t, 2H, J=6.5), 2.76 (dd, 1H, J=14.4, 7.9), 2.46 (s, 3H); low resolution MS (ES+)m/e 434.9 (MH$^+$).

Intermediate 51: (2S)-2-amino-3-(4-{2-[2-(4-isopropoxyphenyl)-5-methyl-1,3-oxazol-4-yl]ethoxy}phenyl)propanoic acid Intermediate 51 was prepared from 598 mg of N-(Boc)-L-Tyrosine methyl ester and 530 mg of Intermediate 14 to yield 540 mg (63% overall yield) of the title compound as a solid. $^1$H NMR (DMSO-d$_6$, 400 MHz) δ7.77 (d, 2H, J=8.7), 7.12 (d, 2H, J=8.6), 6.9 (d, 2H, J=8.9), 6.82 (d, 2H, J=8.5), 4.65 (hept, 1H, J=6.0), 4.13 (t, 2H, J=6.6), 3.0 (dd, 1H, J=14.4, 4.5), 2.85 (t, 2H, J=6.4), 2.76 (dd, 1H, J=14.4, 8.0), 2.31 (s, 3H), 1.25 (d, 6H, J=6.0); low resolution MS (ES+)m/e 425.2 (MH$^+$).

Intermediate 52: (2S)-2-amino-3-{4-[2(5-ethyl-2-phenyl-1,3-oxazol-4-yl)ethoxy]phenyl}propanoic acid To a mixture of 640 mg (2.95 mmol, 1.1 eq.) of alcohol intermediate 8B, 790 mg (2.67 mmol, 1.0 eq.) of N-(Boc)-L-Tyrosine methyl ester, and 773 mg (2.95 mmol, 1.1 eq.) of triphenylphosphine in 15 mL of anhydrous toluene at 50° C. was added 702 mg (3.47 mmol, 1.3 eq) of DIAD as a solution in 10 mL of toluene. Stirred 2.5 hr at 50° C. Cooled, concentrated, purified by loading directly onto a silica gel column. Elution with EtOAc/Hexanes (1/20 to 1/1) gave 1.15 grams (87% yield) of BOC-protected intermediate methyl ester of sufficient purity to carry forward into the following deprotection reactions [$^1$H NMR (DMSO-d$_6$, 300 MHz) δ8.07–8.03 (m, 2H), 7.47 (m, 3H), 7.03 (d, 2H, J=8.5), 6.85 (d, 2H, J=8.5), 4.58–4.51 (m, 1H), 4.26 (t, 2H, J=6.5), 3.72 (s, 3H), 3.06–3.0 (m, 4H), 2.78 (q, 2H, J=7.5),, 1.43 (s, 9H), 1.34 (t, 3H, J=7.6)]; Deprotections: To a THF/H$_2$O (15 mL/5 mL) solution of 900 mg of the above protected amino acid at 0° C. was added 2.64 mL of a 1.0 M LiOH in water solution. Stirred 2.5 hrs. Diluted the mixture with 30 mL of EtOAc and the pH was adjusted downward to ~6 by the addition of 0.1 M HCl solution. The aqueous was extracted with EtOAc. The organics were dried (MgSO$_4$) and concentrated, then taken into DCM (15 mL) at 0° C. and treated with 7.5 mL of TFA. The solution was concentrated after 1 hr, then concentrated several times from DCM to yield 1.4 g of crude intermediate 52 (TFA salt). This solid was stirred with 50 mL of Et$_2$O for 30 min. The solids were collected via filtration and dried under vacuum for 12 h to yield 740 mg (67%) of the title compound as an off white solid: $^1$H NMR (DMSO-d$_6$, 300 MHz) δ8.18 (br s, 2H), 7.93–7.90 (m, 2H), 7.51–7.48 (m, 3H), 7.15 (d, 2H, J=8.5), 6.89 (d, 2H, J=8.4), 4.18 (t, 2H, J=7.5), 4.11 (m, 1H), 3.01–2.99 (m, 2H), 2.95–2.95 (m, 2H), 2.75 (q, 2H, J=7.5), 1.23 (t, 3H, J=7.5); low resolution MS (ES$^+$)m/e 381.07 (MH$^+$).

Intermediate 53: (2S)-2-amino-3-{(4-[2-2-phenyl-5-propyl-1,3-oxazol-4-yl)ethoxy]phenyl}propanoic acid Amino acid Intermediate 53 was prepared as described for the preparation of Intermediate 46. From 460 mg of N-(Boc)-L-Tyrosine methyl ester and 360 mg of Intermediate 8C was prepared 410 mg (67% overall yield) of the title compound as a solid: $^1$H NMR (DMSO-d$_6$, 300 MHz) δ7.90–7.87 (m, 2H), 7.48–7.46 (m, 3H), 7.13 (d, 2H, J=8.4), 6.85 (d, 2H, J=8.4), 4.17 (t, 2H, J=6.3), 4.0 (t, 1H, J=6.3), 2.99 (t, 1H, J=6.3), 2.92 (t, 1H, J=6.3), 2.69 (t, 2H, J=7.2), 1.66 (q, 2H, J=7.5), 0.93 (t, 3H, J=7.2); low resolution MS (ES+)m/e 395.09 (MH+); TLC $R_f$=0.24 (10/1,DCM/MeOH).

Intermediate 54: (2S)-2-amino-3-{4-[(5-methyl-2-phenyl-1,3-oxazol-4-yl)methoxy]phenyl}propanoic acid Amino acid Intermediate 54 was prepared as described for the preparation of Intermediate 46. From 187 mg of N-(Boc)-L-Tyrosine methyl ester and 120 mg of Intermediate 8D (with DIAD replacing DEAD) was prepared 116 mg (53% overall yield) of the title compound as a solid. $^1$H NMR (DMSO-d$_6$, 300 MHz) δ7.89–7.85 (m, 2H), 7.43–7.36 (m, 3H), 7.12 (d, 2H, J=8.5), 6.9 (d, 2H, J=8.5), 4.9 (s, 2H), 3.63 (m, 1H), 3.0 (dd, 1H, J=14.4, 4.5), 2.85 (dd, 1H, J=14.4, 8.1), 2.37 (s, 3H); low resolution MS (ES+)m/e 353.07 (MH+).

Intermediate 55: (2S)-2-amino-3-{4-[3-(5-methyl-2-phenyl-1,3-oxazol-4-yl)propoxy]phenyl}propanoic acid Amino acid Intermediate 55 was prepared as described for the preparation of Intermediate 46. From 503 mg of N-(Boc)-L-Tyrosine methyl ester and 370 mg of Intermediate 8E to yield 443 mg (68% overall yield) of the title compound as a solid. $^1$H NMR (DMSO-d$_6$, 300 MHz) δ7.90–7.86 (m, 2H), 7.52–7.44 (m, 3H), 7.14 (d, 2H, J=8.5), 6.86 (d, 2H, J=8.4), 3.94 (t, 2H, J=6.2), 3.75 (m, 1H), 3.03 (dd, 1H, J=14.3, 5.1), 2.90 (dd, 1H, J=14.3, 7.2), 2.59 (t, 2H, J=7.3), 2.27 (s, 3H), 2.0 (m, 2H); TLC $R_f$=0.22 (10/1, DCM/MeOH); low resolution MS (ES+)m/e 381.12 (MH+).

Intermediate 56: (2S)-2-amino-3-(4-{2-[5ethyl-2-(4-fluorophenyl)-1,3-thiazol-4-yl]ethoxy}phenyl) propanoic acid Intermediate 56 was prepared as described above for the preparation of intermediate 52. From 534 mg of N-(Boc)-L-Tyrosine methyl ester and 500 mg of Intermediate 11B was prepared 900 mg of BOC-protected intermediate methyl ester (94% yield; $^1$H NMR (CDCl$_3$, 300 MHz) δ7.9 (dd, 2H, 8.7, 5.2), 7.13 (t, 2H, J=8.6), 7.04 (d, 2H, J=8.5), 6.85 (d, 2H, J=8.6), 4.97 (d, 1H, J=7.9), 4.55 (m, 1H), 4.32 (t, 2H, J=6.8), 3.73 (s, 3H), 3.21 (t, 2H, J=6.7), 3.10–3.02 (m, 2H), 2.89 (q, 2H, J=7.5), 1.44 (s, 9H), 1.36 (t, 3H, J=7.5); From 850 mg of protected intermediate was prepared 900 mg of intermediate 56 as a solid. $^1$H NMR (DMSO-d$_6$, 300 MHz) δ8.0 (br s, 2H), 7.91–7.87 (m, 2H), 7.30 (dt, 2H, J=8.8, 2.1), 7.14 (d, 2H, J=8.6), 6.90 (d, 2H, J=8.6), 4.27 (t, 2H, J=6.5), 4.12 (m, 1H), 3.11 (t, 2H, J=6.5), 3.0 (m, 2H), 2.86 (q, 2H, J=7.5), 1.26 (t, 3H, J=7.5); low resolution MS (ES+)m/e 414.85 (MH+).

Intermediate 57: (2S)-2-amino-3-{4-[2-(5-ethyl-2-phenyl-1,3-thiazol-4-yl)ethoxy]phenyl}propanoic acid Intermediate 57 was prepared as described above for the preparation of intermediate 52. From 575 mg of N-(Boc)-L-Tyrosine methyl ester and 500 mg of Intermediate 9B was prepared 940 mg of BOC-protected intermediate methyl ester (94% yield; $^1$H NMR (DMSO-d$_6$, 300 MHz) δ7.93 (m, 2H), 7.47–7.41 (m, 3H), 7.04 (d, 2H, J=8.4), 6.86 (d, 2H, J=8.6), 4.96 (d, 1H, J=4.56 (m, 1H), 4.34 (t, 2H, J=6.8), 3.73 (s, 3H), 3.23 (t, 2H, J=6.9), 3.04 (m, 2H), 2.90 (q, 2H, J=7.5), 1.44 (s, 9H), 1.37 (t, 3H, J=7.5)); From 900 mg of protected intermediate was prepared 900 mg of intermediate 57 as a solid. $^1$H NMR (DMSO-d$_6$, 300 MHz) δ8.16 (br s, 2H), 7.85 (m, 2H), 7.5–7.43 (m, 3H), 7.14 (d, 2H, J=8.6), 6.90 (d, 2H, J=8.6), 4.27 (t, 2H, J=6.5), 4.12 (m, 1H), 3.12 (t, 2H, J=6.5), 3.0 (m, 2H), 2.86 (q, 2H, J=7.5), 1.26 (t, 3H, J=7.5).

Intermediate 58: (2S)-2-amino-3-(4-{2-[5-ethyl-2-(4-fluorophenyl)-1,3-oxazol-4-yl]ethoxy}phenyl) propanoic acid Intermediate 58 was prepared as described above for the preparation of intermediate 52. From 230 mg of N-(Boc)-L-Tyrosine methyl ester and 200 mg of Intermediate 10B was prepared 350 mg of BOC-protected intermediate methyl ester (88% yield; $^1$H NMR (DMSO-d$_6$, 300 MHz) δ8.07–8.01 (m, 2H), 7.15 (t, 2H, J=8.7), 7.04 (d, 2H, J=8.5), 6.84 (d, 2H, J=8.5), 4.50 (m, 1H), 4.24 (t, 2H, J=6.5), 3.72 (s, 3H), 3.04–2.99 (m, 2H), 2.77 (q, 2H, J=7.5), 1.44 (s, 9H), 1.33 (t, 3H, J=7.5); From 340 mg of BOC-protected ester intermediate was prepared 350 mg of intermediate 58 as a crude off-white colored solid. $^1$H NMR (DMSO-d$_6$, 400 MHz) δ8.13 (br s, 2H), 7.91 (dd, 2H, J=8.8, 5.3), 7.3 (t, 2H, J=8.9), 7.10 (d, 2H, J=8.6), 6.85 (d, 2H, J=8.4), 4.13 (t, 2H, J=6.4), 4.08 (m, 1H), 2.98–2.95 (m, 2H), 2.88 (t, 2H, J=6.5), 2.70 (q, 2H, J=7.4), 1.19 (t, 3H, J=7.5); low resolution MS (ES+)m/e 399.13 (MH+).

Intermediate 59: (2S)-2-amino-3(4-{3-[5-ethyl-244-fluorophenyl)-1,3-oxazol-4-yl]propoxy}phenyl) propanoic acid Intermediate 59 was prepared as described above for the preparation of intermediate 52. From 370 mg of N-(Boc)-L-Tyrosine methyl ester and 310 mg of Intermediate 10C was prepared 575 mg of BOC-protected intermediate methyl ester (87% yield; $^1$H NMR (CDCl$_3$, 400 MHz) δ7.95 (dd, 2H, J=8.6, 5.4), 7.09 (t, 2H, J=8.7), 6.99 (d, 2H, J=8.4), 6.79 (d, 2H, J=8.5), 4.50 (m, 1H), 3.92 (t, 2H, J=7.1), 3.68 (s, 3H), 3.05–2.93 (m, 2H), 2.69–2.59 (m, 2H), 2.16–2.08 (m, 2H), 1.39 (s, 9H), 1.17 (t, 3H, J=7.6); From 562 mg of BOC-protected ester intermediate was prepared the crude TFA salt of intermediate 59 as a solid (87%); $^1$H NMR (DMSO-d$_6$, 400.MHz) δ7.97–7.9 (m, 2H), 7.33 (t, 2H, J=8.8), 7.14 (d, 2H, J=8.3), 6.88 (d, 2H, J=8.1), 3.97 (m, 3H), 3.25–3.01 (m, 2H), 2.68–2.60 (m, 4H), 2.04–1.99 (m, 2H), 1.16 (t, 3H, J=7.4); low resolution MS (ES+)m/e 413.18 (MH+).

Intermediate 60: (2S)-2-amino-3-{4-[3-(5-ethyl-2-phenyl-1,3-oxazol-4-yl)propoxy]phenyl}propanoic acid Intermediate 60 was prepared as described above for the preparation of intermediate 52. From 266 mg of N-(Boc)-L-Tyrosine methyl ester and 208 mg of Intermediate 8F was prepared 360 mg of BOC-protected intermediate methyl ester (79% yield; $^1$H NMR (CDCl$_3$, 300 MHz) δ8.06–8.03 (m, 2H), 7.46–7.44 (m, 3H), 7.04 (d, 2H, J=8.4), 6.85 (d, 2H, J=8.4), 4.97 (d, 1H, J=7.6), 4.57 (m, 1H), 3.99 (t, 2H, J=6.0), 3.74 (s, 3H), 3.05 (m, 2H), 2.77–2.65 (m, 4H), 2.19 (t, 2H, J=6.6), 1.45 (s, 9H), 1.24 (t, 3H, J=7.5); From 352 mg of BOC-protected ester intermediate was prepared the crude TFA salt of intermediate 60. The TFA salt was suspended into water and the pH adjusted to ~7.0 with 10% NaOH. The resulting solids were filtered and dried to yield intermediate 60; $^1$H NMR (DMSO-d$_6$, 400 MHz) δ7.88–7.85 (m, 2H), 7.48–7.43 (m, 3H), 7.11 (d, 2H, J=8.5), 6.82 (d, 2H, J=8.5), 3.92 (t, 2H, J=6.2), 3.55 (m, 1H), 3.0 (dd, 1H, J=14.3, 4.8), 2.8 (dd, 1H, J=14.3, 7.7), 2.67–2.56 (m, 4H), 2.02–1.96 (m, 2H), 1.13 (t, 3H, J=7.4); low resolution MS (ES+)m/e 392.9 (MH+); TLC $R_f$=0.44 (4/1, DCM/MeOH).

Intermediate 61: (2S)-2-amino-3-{4-[(5-ethyl-2-phenyl-1,3-oxazol-4-yl)methoxy]phenyl}propanoic acid Intermediate 61 was prepared as described above for the preparation of intermediate 52. From 465 mg of N-(Boc)-L-Tyrosine methyl ester and 320 mg of Intermediate 8G was prepared 520 mg of BOC-protected intermediate methyl ester (69% yield); $^1$H NMR (CDCl$_3$, 300 MHz) δ8.09–8.06 (m, 2H), 7.47–7.46 (m, 3H), 7.08 (d, 2H, J=8.7), 6.97 (d, 2H, J=8.7), 5.02 (s, 2H), 5.01 (s, 1H), 4.59–4.55 (m, 1H), 3.74 (s, 3H), 3.08–3.02 (m, 2H), 2.83 (q, 2H, J=7.5), 1.45 (s, 9H), 1.32 (t, 3H, J=7.5); From 510 mg of BOC-protected ester intermediate was prepared the crude TFA salt of intermediate 61. The TFA salt was suspended into water and the pH adjusted to ~7.0 with 10% NaOH. The resulting solids were filtered and dried to yield 315 mg of intermediate 61; $^1$H NMR (DMSO-d$_6$, 300 MHz) δ7.96–7.94 (m, 2H), 7.52–7.51 (m, 3H), 7.18 (d, 2H, J=8.4), 6.95 (d, 2H, J=8.4), 4.97 (s, 3H), 3.10–3.05 (m, 1H), 2.86–2.79 (m, 4H), 1.22 (t, 3H, J=7.5); low resolution MS (ES+)m/e 366.86 (MH$^+$); TLC R$_f$=0.52 (4/1, DCM/MeOH).

Intermediate 62: (2S)-2-amino-3-{4-[(5-ethyl-2-phenyl-1,3-thiazol-4-yl)methoxy]phenyl}propanoic acid Intermediate 62 was prepared as described above for the preparation of intermediate 52. From 3.27 g of N-(Boc)-L-Tyrosine methyl ester and 2.43 g of Intermediate 9C was prepared 5.07 g of BOC-protected intermediate methyl ester (92% yield); $^1$H NMR (CDCl$_3$, 300 MHz) δ7.89–7.86 (m, 2H), 7.42–7.38 (m, 3H), 7.01 (d, 2H, J=6.3), 6.94 (d, 2H, J=6.3), 5.11 (s, 2H), 4.94 (d, 1H, J=6.0), 4.53–4.50 (m, 1H), 3.68 (s, 3H), 3.02–2.98 (m, 2H), 2.90 (q, 2H, J=5.7), 1.39 (s, 9H), 1.30 (t, 3H, J=5.7); From 5.05 g of BOC-protected ester intermediate was prepared the crude TFA salt of intermediate 62 as in example 52. The TFA salt was suspended into water and the pH adjusted to ~7.0 with 10% NaOH. The resulting solids were filtered and dried to yield 4.28 g of intermediate 62; $^1$H NMR (DMSO-d$_6$, 400 MHz) δ7.85–7.83 (m, 2H), 7.45–7.43 (m, 3H), 7.16–7.14 (m, 2H), 6.96–6.94 (m, 2H), 5.07 (s, 2H), 3.53 (s, 2H), 3.05–3.02 (m, 1H), 2.91–2.81(m, 4H), 1.21 (t, 3H, J=7.4); low resolution MS (ES+)m/e 382.94 (MH$^+$); TLC R$_f$=0.33 (4/1, DCM/MeOH).

Intermediate 63: (2S)-2-amino-3-(4-{[5-ethyl-2-(4-fluorophenyl)-1,3-oxazol4-yl]methoxy}phenyl)propanoic acid Intermediate 63 was prepared as described above for the preparation of intermediate 52. From 962 mg of N-(Boc)-L-Tyrosine methyl ester and 720 mg of Intermediate 10D was prepared 1.32 g of BOC-protected intermediate methyl ester (81% yield); $^1$H NMR (CDCl$_3$, 300 MHz) δ8.07–8.03 (m, 2H), 7.19–7.13 (m, 2H), 7.08 (d, 2H, J=8.4), 6.97 (d, 2H, J=8.4), 4.99–4.97 (m, 3H), 4.58–4.57 (m, 1H), 3.74 (s, 3H), 3.09–3.03 (m, 2H), 2.82 (q, 2H. J=7.5), 1.59 (s, 9H), 1.30 (t, 3H, J=7.5); From 1.31 g of BOC-protected ester intermediate was prepared the crude TFA salt of intermediate 63. The TFA salt was suspended into water and the pH adjusted to ~7.0 with 10% NaOH. The resulting solids were filtered and dried to yield 1.01 g of the title compound; $^1$H NMR (DMSO-d$_6$, 300 MHz) δ8.01–7.97 (m, 2H), 7.36 (t, 2H, J=9.0), 7.18 (d, 2H, J=8.4), 6.96 (d, 2H, J=8.4), 4.97 (s, 2H), 3.53–3.51 (m, 2H), 3.09–3.04 (m, 2H), 2.84 (q, 2H, J=7.5), 1.22 (t, 3H, J=7.5); low resolution MS (ES+)m/e 384.87 (MH$^+$); TLC R$_f$=0.44 (4/1, DCM/MeOH).

Example 1

(2S)-2{[(Z)-1-methyl-3-oxo-3-phenyl-1-propenyl]amino}-3-{4-[2-(5-methyl-2-phenyl-1,3-oxazol-4-yl)ethoxy]phenyl}propanoic acid A suspension of 3.0 g (8.2 mmol) of Intermediate 45 and 1.86 g (11.5 mmol) of benzoylacetone in 26 mL of MeOH and 6 mL of trimethylorthoformate was refluxed for 16 h with dissolution occurring sometime after 4 hrs. The solution was cooled, concentrated, and the resulting crude products were purified by silica gel chromatography eluting with 1% to 100% MeOH in CH$_2$Cl$_2$. Column fractions homogeneous by TLC were combined and concentrated to give 1.8 g (43% yield) of Example 1 as a tan-colored solid: TLC (EtOAc/MeOH (7:3): R$_f$=0.19; $^1$H NMR (DMSO-d$_6$, 400 MHz) δ11.40 (d, 1H, J=8.89), 7.88 (d, 2H, J=7.86), 7.77 (d, 2H, J=7.35), 7.46 (m, 3H), 7.39 (m, 3H), 7.10 (d, 2H, J=8.55), 6.80 (d, 2H, J=8.20), 5.78 (s, 1H), 4.14 (m, 3H), 3.10 (m, 1H), 2.87 (m, 2H), 2.77 (m, 1H), 2.34 (s, 3H), 1.71 (s, 3H); low resolution MS (ES+) m/e 511.1 (MH$^+$): RP-HPLC (Vydac C-18, 25 cm×4.6 mm; 30–100% CH$_3$CN in H$_2$O) with 0.1% HCO$_2$H buffer: 30 minutes; 1 mL/min: t$_r$=18.14 min (t$_o$=1.43); Daicel AD(2) (25 cm×4.6 mm; 20% IPA in Hexane) with 0.1% TFA buffer: 15 minutes; 0.8 mL/min: t$_r$=6.87 min (t$_o$=1.43), 99.9%ee.

Example 2

(2S)-3-(4-{2-[2-(4-fluorophenyl)-5-methyl-1,3-oxazol-4-yl]ethoxy}phenyl)-2-({(Z)-1-methyl-3-oxo-3-[4-(trifluoromethyl)phenyl]-1-propenyl}amino)propanoic acid A mixture of 75 mg (0.2 mmol) of Intermediate 46, 45 mg (0.2 mmol) of Intermediate 24, and 57 μL (0.41 mmol) of triethylamine in 0.5 mL of trimethylorthoformate and 2.5 mL of MeOH was refluxed for 10 hrs. The solvents were evaporated under reduced pressure and the residue purified directly by silica gel chromatography. Elution with 5%–20% MeOH in CH$_2$Cl$_2$ gave 30 mg (26% yield) of Example 2 as a solid (foam); TLC (DCM/MeOH, 4/1): R$_f$=0.58; $^1$H NMR (DMSO-d$_6$, 300 MHz) δ11.59 (d, 1H, J=9.8), 8.03 (m, 4H), 7.81 (d, 2H, J=8.8), 7.38 (t, 2H, J=9.2), 7.19 (d, 2H, J=8.8), 6.88 (d, 2H, J=8.8), 5.76 (s, 1H), 4.21 (t, 2H, J=6.6), 4.17 (m, 1H), 3.20 (m, 1H), 2.96 (t, 2H, J=6.6), 2.82 (m, 1H), 2.39 (s, 3H), 1.76 (s, 3H); low resolution MS (ES+)m/e 597.0 (MH$^+$).

Example 3

(2S)-3-(4-{2-[2-(4-isopropoxyphenyl)-5-methyl-1,3-oxazol4-yl]ethoxy}phenyl)-2-({(Z)-1-methyl-3-oxo-3-[4-(trifluoromethyl)phenyl]-1-propenyl}amino)propanoic acid The title compound was prepared (as described above for the preparation of Example 2) from 75 mg (0.18 mmol) of Intermediate 51 and 41 mg (0.18 mmol) of Intermediate 24 to yield 48 mg (43% yield) of Example 3: TLC (DCM/MeOH, 4/1): R$_f$=0.42; $^1$H NMR (DMSO-d$_6$, 400 MHz) δ11.5 (d, 1H, J=8.9), 7.95 (d, 2H, J=7.2), 7.77 (d, 2H, J=8.7), 7.72 (d, 2H, J=8.2), 7.1 (d, 2H, J=8.4), 6.97 (d, 2H, J=8.9), 6.79 (d, 2H, J=8.5), 5.58 (s, 1H), 4.65 (m, 1H), 4.11 (t, 2H, J=6.5), 4.1 (m, 1H), 3.16 (dd, 1H, J=13.7, 3.6), 2.84 (t, 2H, J=6.5), 2.74 (dd, 1H, 13.7, 9.0), 2.28 (s, 3H), 1.67 (s, 3H), 1.25 (d, 6H, J=6.0); low resolution MS (ES+)m/e 637.1 (MH$^+$);

Example 4

(2S)-3-(4-{2-[2-4-methoxyphenyl)-5-methyl-1,3oxazol-4-yl]ethoxy}phenyl)-2-({(Z)-1-methyl-3-oxo-3-[4(trifluoromethyl)phenyl]-1-propenyl}amino)propanoic acid The title compound was prepared (as described above for the preparation of Example 2) from 100 mg (0.25 mmol) of Intermediate 49 and 58 mg (0.25 mmol) of Intermediate 24 to yield 66 mg (43% yield) of Example 4: TLC (DCM/MeOH, 4/1): $R_f$=0.48; $^1$H NMR (DMSO-$d_6$, 400 MHz) δ11.5 (d, 1H, J=8.9), 7.95 (d, 2H, J=8.2), 7.80 (d, 2H, J=8.7), 7.72 (d, 2H, J=8.4), 7.1 (d, 2H, J=8.4), 7.0 (d, 2H, J=8.9), 6.79 (d, 2H, J=8.5), 5.58 (s, 1H), 4.11 (t, 2H, J=6.5), 4.1 (m, 1H), 3.78 (s, 3H), 3.15 (dd, 1H, J=13.6, 3.6), 2.84 (t, 2H, J=66), 2.75 (dd, 1H, 13.7, 9.0), 2.28 (s, 3H), 1.67 (s, 3H); low resolution MS (ES+)m/e 609.0 (MH$^+$);

Example 5

(2S)-2-{[(Z)-1-ethyl-3-oxo-3-phenyl-1-propenyl]amino}-3-[4-(2-{5-methyl-2-[4-(trifluoromethyl)phenyl]-1,3-oxazol-4-yl}ethoxy)phenyl]propanoic acid The title compound was prepared (as described above for the preparation of Example 2) from 40 mg (0.092 mmol) of Intermediate 50 and 17 mg (0.092 mmol) of Intermediate 16 to yield 21 mg of Example 5: TLC (DCM/MeOH, 4/1): $R_f$=0.50; $^1$H NMR (DMSO-$d_6$, 400 MHz) δ11.59 (d, 1H, J=9.8), 8.09 (d, 2H, J=9.0), 7.85 (d, 2H, J=8.8), 7.78 (m, 2H), 7.39 (m, 3H), 7.12 (d, 2H, J=8.0), 6.80 (d, 2H, J=8.0), 5.54 (s, 1H), 4.15 (t, 2H, J=6.6), 4.17 (m, 1H), 3.11 (m, 1H), 2.90 (t, 2H, J=6.6), 2.72 (m, 1H), 2.33 (s, 3H), 1.98 (m, 2H), 0.9 (t, 3H, J=7.5); low resolution MS (ES+)m/e 593.1 (MH$^+$).

Example 6

(2S)-2-([(Z)-1-ethyl-3-(4-fluorophenyl)-3-oxo-1-propenyl]amino}-3-(4-{2-[2-(4-methoxyphenyl)-5-methyl-1,3-oxazol-4-yl]ethoxy}phenyl)propanoic acid The title compound was prepared (as described above for the preparation of Example 2) from 100 mg (0.25 mmol) of Intermediate 49 and 62 mg (0.32 mmol) of Intermediate 32 to yield 90 mg of Example 6: TLC (DCM/MeOH, 4/1): $R_f$=0.46; $^1$H NMR (DMSO-$d_6$, 400 MHz) δ11.45 (d, 1H, J=9.6), 7.84 (m, 4H), 7.19 (t, 2H, J=8.8), 7.10 (d, 2H, J=8.4), 7.01 (d, 2H, J=8.8), 6.78 (d, 2H, J=8.4), 5.51 (s, 1H), 4.11 (t, 2H, J=6.8), 4.03 (m, 1H), 3.11 (m, 1H), 2.84 (t, 2H, J=6.8), 2.71 (dd, 1H, J=14.0, 9.2), 2.31 (s, 3H), 1.98 (m, 2H), 0.90 (t, 3H, J=7.2); low resolution MS (ES−)m/e 571.2 (M-H).

Example 7

(2S)-2-{[(Z)-1-methyl-3-oxo-3-phenyl-1-propenyl]amino}-3-[4-(2-{5-methyl-2-[4-(trifluoromethyl)phenyl]-1,3-oxazol-4-yl}ethoxy)phenyl]propanoic acid The title compound was prepared (as described above for the preparation of Example 2) from 40 mg (0.092 mmol) of Intermediate 50 and 15 mg (0.092 mmol) of benzoylacetone to yield 32 mg of Example 7: TLC (DCM/MeOH, 4/1): $R_f$=0.48; $^1$H NMR (DMSO-$d_6$, 300 MHz) δ11.49 (d, 1H, J=9.8), 8.17 (d, 2h, J=8.9), 7.9 (d, 2H, J=8.9), 7.85 (m, 2H), 7.44 (m, 3H), 7.19 (d, 2H, J=8.8), 6.89 (d, 2H, J=8.8), 5.60 (s, 1H), 4.23 (t, 2H, J=6.0), 4.16 (m, 1H), 3.21 (m, 2H), 2.99 (t, 2H, J=6.0), 2.82 (dd, 1H, J=14.2, 9.8), 2.42 (s, 3H), 1.78 (s, 3H); low resolution MS (ES+)m/e 579.0 (MH$^+$).

Example 8

(2S)-2-{[(Z)-1-ethyl-3-oxo-3-phenyl-1-propenyl]amino}-3-(4-{2-[2-(4-fluorophenyl)-5-methyl-1,3-oxazol-4-yl]ethoxy}phenyl)propanoic acid The title compound was prepared (as described above for the preparation of Example 2) from 75 mg (0.195 mmol) of Intermediate 46 and 34 mg (0.2 mmol) of Intermediate 16 to yield 32 mg of Example 8: TLC (DCM/MeOH, 4/1): $R_f$=0.63; $^1$H NMR (DMSO-$d_6$, 300 MHz) δ11.57 (d, 1H, J=9.6), 7.97 (m, 2H), 7.86 (d, 1H, J=7.2), 7.42 (m, 5H), 7.18 (d, 2H, 8.4), 6.87 (d, 2H, J=8.4), 5.61 (s, 1H), 4.20 (t, 2H, J=6.6), 4.14 (m, 1H), 3.22 (m, 2H), 2.94 (t, 2H, J=6.6), 2.83 (dd, 1H, J=13.8, 9.3); low resolution MS (ES+)m/e 543 (MH$^+$).

Example 9

(2S)-2-{[(Z)-1-ethyl-3-(4-fluorophenyl)-3-oxo-1-propenyl]amino}-3-(4-{2-[2(4-fluorophenyl)-5-methyl-1,3-oxazol-4-yl]ethoxy}phenyl)propanoic acid The title compound was prepared (as described above for the preparation of Example 2) from 500 mg (1.56 mmol) of Intermediate 46 and 315 mg (1.56 mmol) of Intermediate 32 to yield 412 mg of Example 9: TLC (DCM/MeOH, 4/1): $R_f$=0.53; $^1$H NMR (DMSO-$d_6$, 300 MHz) δ11.53 (d, 1H, J=9.3), 7.99 (m, 2H), 7.95 (m, 2H), 7.39 (t, 2H, J=8.7), 7.26 (t, 2H, J=8.7), 7.17 (d, 2H, J=8.1), 6.86 (d, 2H, J=8.1), 5.60 (s, 1H), 4.20 (t, 2H, J=6.6), 4.12 (m, 1H), 3.21 (m, 2H), 2.94 (t, 2H, J=6.6), 2.78 (dd, 1H, J=13.8, 8.4), 2.38 (s, 3H), 2.05 (m, 2H), 0.96 (t, 3H, J=7.5); low resolution MS (ES+)m/e 561.4 (MH$^+$).

Example 10

(2S)-2-({(Z)-1-methyl-3-oxo-3-[4-(trifluoromethyl)phenyl]-1-propenyl}amino)-3-{4-[2-(5-methyl-2-phenyl-1,3-thiazol-4-yl)ethoxy]phenyl}propanoic acid The title compound was prepared (as described above for the preparation of Example 2) from 290 mg (0.76 mmol) of Intermediate 47 and 150 mg (0.76 mmol) of Intermediate 24 to yield 140 mg (31% yield) of Example 10: TLC (DCM/MeOH, 4/1): $R_f$=0.47; $^1$H NMR (DMSO-$d_6$, 300 MHz) δ11.52 (d, 1H, J=8.9), 7.96 (d, 2H, J=8.1), 7.80 (m, 2H), 7.72 (d, 2H, J=8.4 ), 7.42 (m, 3H), 7.10 (d, 2H, J=8.4), 6.80 (d, 2H, J=8.4), 5.61 (s, 1H), 4.20 (t, 2H, J=6.6), 4.15 (m, 1H), 3.17 (m, 1H), 3.05 (t, 2H, J=6.5), 2.77 (dd, 1H, J=13.6, 8.6), 2.41 (s, 3H), 1.69 (s, 3H); low resolution MS (ES+)m/e 595.0 (MH$^+$).

Example 11

(2S)-2-{[(Z)-3-(4-fluorophenyl)-1-methyl-3-oxo-1-propenyl]amino}-3-{4-[2-(5-methyl-2-phenyl-1,3-oxazol-4-yl)ethoxy]phenyl}propanoic acid A solution of 100 mg (0.27 mmol) of Intermediate 45 and 49 mg (0.27 mmol) of Intermediate 26 in 2.5 mL MeOH and 0.5 mL trimethyl orthoformate was refluxed at 80° C. for 16 h. The reaction solution was concentrated and purified by flash silica gel chromatography using EtOAc/MeOH 7/3 as eluent to afford 83 mg of Example 11: TLC (EtOAc/MeOH, 7/3): $R_f$=0.28; $^1$H NMR (DMSO-$d_6$) δ11.38 (d, 1H, J=7.00), 7.84 (m, 4H), 7.45 (m, 3H), 7.16 (t, 2H, J=8.72), 7.09 (d, 2H, J=7.69), 6.77 (d, 2H, J=7.69), 5.49 (s, 1H), 4.11 (m, 2H), 4.01(m, br, 1H), 3.13 (m, 1H), 2.86 (m, 2H), 2.72 (s, br, 1H), 2.30 (s, 3H), 1.62 (s, 3H); low resolution MS (ES) m/e 529 (MH$^+$); RP-HPLC (Vydac C-18, 25 cm×4.6 mm; 30–100% CH$_3$CN in H$_2$O) with 0.1% HCO$_2$H buffer: 30 minutes; 1 mL/min: $t_r$=20.10 min ($t_o$=1.53).

Example 12

(2S)-2-{[(Z)-1-methyl-3-oxo-3-(2,3,4-trifluorophenyl)-1-propenyl]amino}-3-{4-[2-(5-methyl-2-phenyl-1,3-oxazol-4-yl)ethoxy]phenyl}propanoic acid A mixture of 680 mg (1.85 mmol) of Intermediate 45, 367 mg (1.85 mmol) of Intermediate 36, and 0.67 mL (3.7 mmol)

of DIEA in 15 mL of MeOH was refluxed overnight (14 h). The solvent was evaporated under reduced pressure and the residue purified directly by silica gel chromatography. Elution with 5%–20% MeOH in $CH_2Cl_2$ gave 612 mg (58% yield) of the title compound as a solid: TLC (DCM/MeOH, 4/1): $R_f$=0.50; $^1$H NMR (DMSO-$d_6$, 300 MHz) δ11.35 (d, 1H, J=9.0), 7.87 (m, 2H), 7.48 (m, 4H), 7.3 (q, 1H, J=5.4), 7.10 (d, 2H, J=8.7), 6.78 (d, 2H, J=8.7), 5.25 (s, 1H), 4.18 (m, 3H), 3.19 (m, 2H), 2.86 (t, 2H, J=6.3), 2.74 (dd, 1H, J=13.8, 9.0), 2.32 (s, 3H), 1.64 (s, 3H); low resolution MS (ES+)m/e 564.9 (MH$^+$);

Example 13

(2S)-2-{[(Z)-1-methyl-3-(4-nitrophenyl)-3-oxo-1-propenyl]amino}-3-{4-[2-(5ethyl-2-phenyl-1,3oxazol-4-yl)ethoxy]phenyl}propanoic acid The title compound was prepared (as described above for the preparation of Example 12) from 120 mg (0.33 mmol) of Intermediate 45 and 62 mg (0.33 mmol) of Intermediate 41 to yield 105 mg (58% yield) of Example 13: TLC (DCM/MeOH, 4:1): $R_f$=0.60; $^1$H NMR (DMSO-$d_6$, 300 MHz) δ11.66 (d, 1H, J=9.0), 8.29 (d, 2H, J=8.4), 8.08 (d, 2H, J=8.4), 7.97 (m, 2H) 7.56 (m, 3H), 7.19 (d, 2H, J=8.0), 6.88 (d, 2H, J=8.0), 5.72 (s, 1H), 4.18 (m, 3H), 3.23 (m, 1H), 2.96 (t, 2H, J=6.2), 2.85 (dd, 1H, J=13.4, 9.6), 2.39 (s, 3H), 1.79 (s, 3H); low resolution MS (ES+)m/e 556.4 (MH$^+$).

Example 14

(2S)-2-({(Z)-1-methyl-3-oxo-3-[4-(trifluoromethyl)phenyl]-1-propenyl}amino)-3-{4-[2-(5-methyl-2-phenyl-1,3oxazol-4-yl)ethoxy]phenyl}propanoic acid A solution of 676 mg (1.85 mmol) of Intermediate 45 and 510 mg (2.22 mmol) of Intermediate 24 in 30 mL MeOH and 6 mL trimethyl orthoformate with 4 A sieves (300 mg) was refluxed at 80° C. for 16 h. The reaction solution was concentrated and purified by flash silica gel column chromatography using DCM/MeOH 15/1 followed by DCM/MeOH 10/1 as eluent to afford 329 mg of Example 14: TLC (DCM/MeOH (9:1): $R_f$=0.26; $^1$H NMR (DMSO-$d_6$, 300 MHz) δ11.59 (d, 1H, J=9.0), 8.03 (d, 2H, J=8.1), 7.95 (m, 2H), 7.80 (d, 2H, J=8.1), 7.56 (m, 3H), 7.19 (d, 2H, J=8.4), 6.87 (d, 2H, J=8.4), 5.66 (s, 1H), 4.18 (m, 3H), 3.23 (m, 2H), 2.95 (t, 2H, J=6.6), 2.82 (dd, 1H, J=13.8, 9.0), 2.39 (s, 3H), 1.75 (s, 3H); low resolution MS (ES+)m/e 579 (MH$^+$); RP-HPLC (Vydac C-18, 25 cm×4.6 mm; 30–100% $CH_3CN$ in $H_2O$) with 0.1% $HCO_2H$ buffer: 30 minutes; 1 mL/min: $t_r$=21.47 min ($t_o$=1.53).

Example 15

(2S)-2-{[(Z)-1-ethyl-3-(4-fluorophenyl)-3-oxo-1-propenyl]amino}-3-(4-{2-[2-(4-isopropoxyphenyl)-5-methyl-1,3-oxazol-4-yl]ethoxy}phenyl)propanoic acid The title compound was prepared (as described above for the preparation of Example 2) from 75 mg (0.177 mmol) of Intermediate 51 and 39 mg (0.194 mmol) of Intermediate 32 to yield 70 mg of Example 15: TLC (DCM/MeOH (4:1): $R_f$=0.55; $^1$H NMR (DMSO-$d_6$, 300 MHz) δ11.53 (d, 1H, J=9.6), 7.89 (dd, 2H, J=8.8, 5.7), 7.85 (d, 2H, J=8.8), 7.26 (t, 2H, J=8.8), 7.18 (d, 2H, J=8.5), 7.05 (d, 2H, J=8.8), 6.86 (d, 2H, J=8.5), 5.60 (s, 1H), 4.73 (hept, 1H, J=6.0), 4.19 (t, 2H, J=6.7), 4.13 (br s, 1H), 3.19 (m, 1H), 2.92 (t, 2H, J=6.6), 2.80 (dd, 1H, J=14.0, 9.2), 2.36 (s, 3H), 2.07 (m, 2H), 1.34 (d, 6H, J=6.0), 0.99 (t, 3H, J=7.5); low resolution MS (ES+)m/e 601.1 (MH$^+$).

Example 16

(2S)-2-{[(Z)-1-methyl-3-oxo-3-(2,4,5-trifluorophenyl)-1-propenyl]amino}-3-{4-[2-(5-methyl-2-phenyl-1,3-oxazol-4-yl)ethoxy]phenyl}propanoic acid The title compound was prepared (as described above for the preparation of Example 12) from 677 mg (1.85 mmol) of Intermediate 45 and 366 mg (1.85 mmol) of Intermediate 38 to yield 482 mg (46% yield) of Example 16. TLC (DCM/MeOH (4:1): $R_f$=0.55; $^1$H NMR (DMSO-$d_6$, 300 MHz) δ11.39 (d, 1H, J=8.9), 7.86 (m, 2H), 7.69–7.59 (m, 1H), 7.54–7.40 (m, 4H), 7.10 (d, 2H, J=8.5), 6.79 (d, 2H, J=8.5), 5.3 (s, 1H), 4.12 (t, 2H, J=6.5), 4.1 (m, 1H), 3.16 (m, 1H), 2.86 (t, 2H, J=6.5), 2.76 (dd, 1H, J=13.7, 8.9), 2.3 (s, 3H), 1.64 (s, 3H): low resolution MS (ES+)m/e 565.1 (MH$^+$).

Example 17

(2S)-2-{[(Z)-1-ethyl-3-oxo-3-phenyl-1-propenyl]amino}-3-(4-{2-[2-(4-isopropoxyphenyl)-5-methyl-1,3oxazol-4-yl]ethoxy}phenyl)propanoic acid The title compound was prepared (as described above for the preparation of Example 2) from 75 mg (0.177 mmol) of Intermediate 51 and 34 mg (0.194 mmol) of Intermediate 16 to yield 30 mg of Example 17: TLC (DCM/MeOH (4:1): $R_f$=0.63; $^1$H NMR (DMSO-$d_6$, 400 MHz) δ11.49 (d, 1H, J=9.6), 7.77 (m, 4H), 7.37 (m, 3H), 7.10 (d, 2H, J=8.8), 6.97 (d, 2H, J=9.2), 6.79 (d, 2H, J=9.2), 5.54 (s, 1H), 4.66 (septuplet, 1H, J=6.0), 4.12 (t, 2H, J=6.8), 4.04 (m, 1H), 3.35 (m, 1H), 3.11 (m, 1H), 2.84 (t, 2H, J=6.8), 2.72 (dd, 1H, J=13.9, 9.2), 2.28 (s, 3H), 1.99 (m, 2H), 1.26 (d, 6H, J=6.0), 0.91 (m 3H, J=7.6); low resolution MS (ES+)m/e 583.1 (MH$^+$).

Example 18

(2S)-2-({(Z)-1-ethyl-3-oxo-3-[4-(trifluoromethyl)phenyl]-1-propenyl}amino)-3-{4-[2-(5-methyl-2-phenyl-1,3-oxazol-4-yl)ethoxy]phenyl}propanoic acid The title compound was prepared (as described above for the preparation of Example 2) from 197 mg (0.41 mmol) of Intermediate 45 (as the TFA salt) and 100 mg (0.41 mmol) of Intermediate 25 to yield 110 mg (45% yield) of Example 18: TLC (DCM/MeOH (4:1): $R_f$=0.60; $^1$H NMR (DMSO-$d_6$, 400 MHz) δ11.45 (d, 1H, J=9.2), 7.85 (m, 4H), 7.47 (m, 3H), 7.17 (t, 2H, J=8.8), 7.09 (d, 2H, J=8.4), 6.78 (d, 2H, J=8.4), 5.51 (s, 1H), 4.12 (t, 2H, J=6.4), 4.02 (m, 1H), 3.10 (m, 2H), 2.86 (t, 2H, J=6.4), 2.71 (dd, 1H, J=13.9, 9.2), 2.31 (s, 3H), 1.98 (s, 3H), 0.90 (t, 3H, J=7.6); low resolution MS (ES+) m/e 593 (MH$^+$).

Example 19

(2S)-2-{[(Z)-1-methyl-3-(4-methylphenyl)-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 790 mg (1.64 mmol) of Intermediate 45 (as the TFA salt) and 0.29 g (1.64 mmol) of Intermediate 27 (with 660 μL of DCA replacing $Et_3N$) to yield crude product contaminated with DCA). A second silica gel chromatography column eluting with 8:1 DCM:MeOH gave 70 mg of Example 19 as a beige-colored solid: TLC (DCM/MeOH (4:1): $R_f$=0.58; $^1$H NMR (DMSO-$d_6$, 400 MHz) δ11.43 (d, 1H, J=9.0), 7.96 (m, 2H), 7.74 (d, 2H, J=8.1), 7.54 (m, 3H), 7.24 (d, 2H, J=8.1), 7.18 (d, 2H, J=8.4), 6.87 (d, 2H, J=8.4), 5.57 (s, 1H), 4.21 (t, 2H, J=6.6), 4.08 (m, 1H), 3.23 (m, 2H), 2.95 (t, 2H, J=6.6), 2.80(dd, 1H, J=13.8, 9.0), 2.39 (s, 3H), 2.37 (s, 3H), 1.71 (s, 3H); low resolution MS (ES+)m/e 525.2 (MH$^+$).

Example 20

(2S)-2-{[(Z)-1-ethyl-3-oxo-3-phenyl-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 1.03 g (2.1 mmol) of Intermediate 45 (as the TFA salt) and 740 mg (4.2 mmol) of Intermediate 16 to yield 500 mg of Example 20 as a white solid: TLC (EtOAc/MeOH, 7/3): $R_f$=0.35; $^1$H NMR (DMSO-$d_6$, 400 MHz) δ11.55 (d, 1H, J=9.6), 7.93 (d, 2H, J=7.8), 7.84 (d, 2H, J=7.8), 7.57 (m, 3H), 7.52 (m, 3H), 7.18 (d, 2H, J=8.4), 6.87 (d, 2H, J=8.4), 5.58 (s, 1H), 4.21 (t, 2H, J=6.6), 4.16 (m, 1H), 3.21 (m, 1H), 2.95 (t, 2H, J=6.6), 2.80 (dd, 1H, J=13.5, 9.0), 2.42 (s, 3H), 2.08 (m, 2H), 1.04 (t, 3H, J=7.8); low resolution MS (ES+)m/e 525 (MH$^+$).

Example 21

(2S)-3-(4-{2-[2-(4-fluorophenyl)-5-methyl-1,3-thiazol-4-yl]ethoxy}phenyl)-2-{[(Z)-3-oxo-3-phenyl-1-(trifluoromethyl)-1-propenyl]amino}propanoic acid A solution of 120 mg (0.31 mmol) of Intermediate 48, 62 mg (0.31 mmol) of Intermediate 44, and 110 μL (2 equivalents) of DIEA in MeOH (3.5 mL) was refluxed for 10 hrs. The solvents were removed under reduced pressure and the crude products were purified by silica gel chromatography (gradient, 15/1 to 10/1 CH$_2$Cl$_2$/MeOH) to give 78 mg (46% yield) of Example 21 as a solid: TLC (DCM/MeOH (4:1): $R_f$=0.62; $^1$H NMR (DMSO-$d_6$, 400 MHz) δ10.9 (br s, 1H), 7.9–7.83 (m, 4H), 7.6–7.43 (m, 3H), 7.27 (t, 2H, J=8.8), 7.05 (d, 2H, J=8.4), 6.78 (d, 2H, J=8.4), 6.13 (s, 1H), 4.2 (t, 2H, J=6.6), 4.08 (br s, 1H), 3.1 (m, 1H), 3.08 (t, 2H, J=6.7), 2.86 (dd, 1H, J=13.6, 7.7), 2.37 (s, 3H); low resolution MS (ES+)m/e 599.0 (MH$^+$).

Example 22

(2S)-2-({(Z)-1-ethyl-3-oxo-3-[4-(trifluoromethyl)phenyl]-1propenyl}amino)-3-(4-{2-[2-(4-fluorophenyl)-5-methyl-1,3-thiazol-4-yl]ethoxy}phenyl)propanoic acid The title compound was prepared (as described above for the preparation of Example 2) from 75 mg (0.19 mmol) of Intermediate 48 and 46 mg (0.19 mmol) of Intermediate 25 to yield 26 mg of Example 22: TLC (DCM/MeOH (4:1): $R_f$=0.58; $^1$H NMR (DMSO-$d_6$, 400 MHz) δ11.59 (d, 1H, J=9.3), 7.97 (d, 2H, J=8.1), 7.85 (m, 2H), 7.72 (d, 2H, J=8.4), 7.29 (m, 2H), 7.10 (t, 2H, J=8.4), 6.79 (d, 2H, J=8.4), 5.60 (s, 1H), 4.20 (t, 2H, J=6.6), 4.12 (m, 1H), 3.16 (m, 1H), 3.06 (t, 2H, J=6.6), 2.75 (dd, 1H, J=13.8, 9.0), 2.38 (s, 3H), 2.02 (m, 2H), 0.92 (t, 3H, J=7.5); low resolution MS (ES+)m/e 627.0 (MH$^+$).

Example 23

(2S)-2-{[(Z)-1-butyl-3-oxo-3-phenyl-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 1.0 g (2.05 mmol) of Intermediate 45 (as the TFA salt) and 0.86 g (4.2 mmol) of Intermediate 18 to yield 290 mg (25% yield) of Example 23 as a solid: TLC (EtOAc/MeOH , 7/3): $R_f$=0.55; $^1$H NMR (DMSO-$d_6$, 400 MHz) δ11.59 (d, 1H, J=9.7), 7.86 (m, 2H), 7.76 (m, 2H), 7.48–7.34 (m, 6H), 7.10 (d, 2H, J=8.5), 7.10 (t, 2H, J=8.4), 6.8 (d, 2H, J=8.6), 5.52 (s, 1H), 4.12 (t, 2H, J=6.5), 4.02 (m, 1H), 3.16 (m, 1H), 2.86 (t, 2H, J=6.5), 2.75 (dd, $_1$H, J=13.5, 9.5), 2.31 (s, 3H), 1.9 (m, 2H), 1.3–1.1 (m, 4H), 0.73 (t, 3H, J=6.9); low resolution MS (ES+)m/e 553.2 (MH$^+$).

Example 24

(2S)-2-{[(Z)-3-(4-chlorophenyl)-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 100 mg (0.27 mmol) of Intermediate 45 and 54 mg (0.27 mmol) of Intermediate 28 to yield 76 mg of Example 24: TLC (DCM/MeOH (4:1): $R_f$=0.52; $^1$H NMR (DMSO-$d_6$, 300 MHz) δ11.52 (d, 1H, J=9.6), 7.97 (m, 2H), 7.87 (d, 2H, J=8.6), 7.55 (m, 5H), 7.18 (d, 2H, J=8.5), 6.86 (d, 2H, J=8.5), 5.59 (s, 1H), 4.21 (t, 2H, J=6.1), 4.09 (m, 1H), 3.22 (m, 1H), 2.96 (t, 2H, J=6.1), 2.78 (dd, $_1$H, J=13.9, 9.4), 2.39 (s, 3H), 1.73 (s, 3H).

Example 25

(2S)-2-{[(Z)-1-methyl-3-(3-nitrophenyl)-3-oxo-1-propenyl]amino}-3-{4-[2-(5-methyl-2-phenyl-1,3oxazol-4-yl)ethoxy]phenyl}propanoic acid The title compound was prepared (as described above for the preparation of Example 12) from 120 mg (0.25 mmol) of Intermediate 45 and 48 mg (0.25 mmol) of Intermediate 42 to yield 67 mg of Example 25: TLC (DCM/MeOH (4:1): $R_f$=0.52; $^1$H NMR (DMSO-$d_6$, 400 MHz) δ11.52 (d, 1H, J=9.1), 8.52 (s, 1H), 8.24 (d, 1H, J=8.2), 8.21 (d, 2H, J=7.7), 7.87 (d, 2H, J=7.7), 7.66 (t, 1H, J=7.9), 7.45 (m, 3H), 7.10 (d, 2H, J=8.2), 6.79 (d, 2H, J=8.3), 5.74 (s, 1H), 4.13 (t, 2H, J=6.6), 4.07 (br s, 1H), 3.15 (m, 1H), 2.87 (t, 2H, J=6.4), 2.75 (m, 1H), 2.31 (s, 3H), 1.68 (s, 3H).; low resolution MS (ES+)m/e 556.3 (MH$^+$).

Example 26

(2S)-2-({(Z)-3-[2-fluoro-3-(trifluoromethyl)phenyl]-1-methyl-3-oxo-1-propenyl}amino)-3-{4-[2-(5-methyl-2-phenyl-1,3-oxazol-4-yl)ethoxy]phenyl}propanoic acid The title compound was prepared (as described above for the preparation of Example 12) from 190 mg (0.52 mmol) of Intermediate 45 and 120 mg (0.52 mmol) of Intermediate 37 to yield 102 mg (35% yield) of Example 26: $^1$H NMR (DMSO-$d_6$, 400 MHz) δ11.36 (d, 1H, J=8.9), 7.9 (m, 3H), 7.77 (t, 1H, J=6.9), 7.46 (m, 3H), 7.42 (m, 1H), 7.11 (d, 2H, J=8.5), 6.81 (d, 2H, J=8.5), 5.22 (s, 1H), 4.14 (t, 2H, J=6.6), 4.1 (m, $_1$H), 3.13 (m, 1H), 2.87 (t, 2H, J=6.6), 2.78 (dd, 1H, J=13.7, 8.5), 2.31 (s, 3H), 1.68 (s, 3H); low resolution MS (ES+)m e 597.4(MH$^+$).

Example 27

(2S)-2-{[(Z)-3-(4-isopropoxyphenyl)-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 435 mg (0.91 mmol) of Intermediate 45 (as the TFA salt) and 200 mg (0.91 mmol) of Intermediate 29 to yield 125 mg of Example 27 as a beige glassy solid: TLC (DCM/MeOH (4:1): $R_f$=0.50; $^1$H NMR (DMSO-$d_6$, 400 MHz) δ11.29 (d, 1H, J=8.8), 7.88 (m, 2H), 7.70 (d, 2H, 8.8), 7.48 (m, 3H), 7.09 (d, 2H, J=8.0), 6.85 (d, 2H, J=8.8), 6.78 (d, 2H, J=8.0), 5.46 (s, 1H), 4.62 (septuplet, 1H, J=6.4), 4.12 (t, 2H, J=6.4), 4.0 (m, 1H), 3.14 (m, 2H), 2.87 (t, 2H; J=6.4), 2.70 (dd, 1H, J=13.2, 9.6), 2.31 (s, 3H), 1.61 (s, 3H), 1.21 (d, 6H, J=6.4); low resolution MS (ES+) m/e 569 (MH$^+$).

Example 28

(2S)-2-{[(Z)-3-(2-chlorophenyl)-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 100 mg (0.27 mmol) of Intermediate 45 and 54 mg (0.27 mmol) of Intermediate 29 to yield 44 mg of Example 27: TLC (DCM/MeOH (4:1): $R_f$=0.47; $^1$H NMR (DMSO-$d_6$, 400 MHz) δ11.12 (d, 1H, J=9.0), 7.91 (m, 2H), 7.44 (m, 3H), 7.39 (m, 1H), 7.33 (m, 3H), 7.17 (d, 2H, J=7.2), 6.80 (d, 2H, J=7.2), 4.97 (s, 1H), 4.14 (m, 3H), 3.16 (m, 1H), 2.88 (m, 2H), 2.77 (m, 1H), 2.32 (s, 3H), 1.61 (s, 3H); low resolution MS (ES−)m/e 545.0 (M-H).

Example 29

(2S)-2-{[(Z)-3-(2-furyl)-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 630 mg (1.31 mmol) of Intermediate 45 (as the TFA salt) and 200 mg (1.31 mmol) of 1-(2-furyl)-1,3-butadione (purchased from Acros Organics) to yield 230 mg (35% yield) of Example 29 as a light brown solid: TLC (DCM/MeOH (4:1): $R_f$=0.62; $^1$H NMR (DMSO-$d_6$, 300 MHz) δ11.07 (d, 1H, J=8.7), 7.88 (m, 2H), 7.69 (d, $_1$H, J=1.0), 7.48 (m, 3H), 7.09 (d, 2H, J=8.5), 6.86 (m, 3H), 6.52 (d, 1H, J=1.5), 5.33 (s, 1H), 4.13 (t, 2H, J=6.6), 4.03 (m, 1H), 3.14 (m, 1H), 2.87 (t, 2H, J=6.6), 2.70 (dd, 1H, J=13.6, 9.0), 2.34 (s, 3H), 1.62 (s, 3H); low resolution MS (ES+)m/e 501.2 (MH$^+$).

Example 30

(2S)-2-{[(Z)-1-methyl-3-oxo-3-(2-pyrazinyl)-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 292 mg (0.61 mmol) of Intermediate 45 (as the TFA salt) and 100 mg (0.61 mmol) of Intermediate 35 to yield 135 mg (43%) of Example 30: TLC (DCM/MeOH (4:1): $R_f$=0.22; $^1$H NMR (DMSO-$d_6$, 400 MHz) δ11.58 (d, 2H, J=8.8), 9.08(s, 1H), 8.68 (s, 1H), 8.60 (s, 1H), 7.87 (d, 2H, J=7.6), 7.45 (m, 3H), 7.11 (d, 2H, J=8.0), 6.81 (d, 2H, J=8.0), 6.04 (s, 1H), 4.13 (m, 3H), 3.17 (m, 1H), 2.87 (t, 2H, J=6.4), 2.78 (dd, 1H, J=13.2, 9.2), 2.31 (s, 3H), 1.71 (s, 3H); low resolution MS (ES−)m/e 511.1 (M-H).

Example 31

(2S)-2-{[(Z)-3-(2,4-difluorophenyl)-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 12) from 120 mg (0.33 mmol) of Intermediate 45 and 59 mg (0.33 mmol) of Intermediate 39 to yield 63 mg (35% yield) of Example 31: TLC (DCM/MeOH (4:1): $R_f$=0.72; $^1$H NMR (DMSO-$d_6$, 400 MHz) δ11.37 (d, 1H, J=9.4), 7.87 (m, 2H), 7.72 (q, 1H, J=6.4), 7.43 (m, 3H), 7.14 (m, 4H), 6.79 (d, 2H, J=8.8), 5.25 (s, 1H), 4.13 (m, 3H), 3.18 (m, 1H), 2.85 (t, 2H, J=6.0), 2.77 (dd, 1H, J=14.0, 9.8), 2.29 (s, 3H), 1.62 (s, 3H) ; low resolution MS (ES−)m/e 545.1 (M-H).

Example 32

(2S)-2-{[(Z)-1-methyl-3-oxo-3-(1,3-thiazol-2-yl)-1-propenyl]amino}-3-{[2-(5-methyl-2-phenyl-1,3-oxazol-4-yl)ethoxy]phenyl}propanoic acid The title compound was prepared (as described above for the preparation of Example 12) from 200 mg (0.43 mmol) of Intermediate 45 (as the TFA salt) and 65 mg (0.43 mmol) of Intermediate 43 to yield 202 mg of crude product. This material was re-columned on silica gel eluting with DCM/MeOH (6/1 to 4/1 gradient) to yield 22 mg of Example 32.: TLC (DCM/MeOH, 4/1): $R_f$=0.42; 1H NMR (DMSO-$d_6$, 300 MHz) δ11.25 (d, 1H, J=9.0), 7.94 (m, 4H), 7.54 (m, 3H), 7.17 (d, 2H, J=8.4), 6.88 (d, 2H, J=8.4), 5.84 (s, 1H), 4.22 (t, 2H, J=6.6), 4.18 (m, 1H), 3.1 (dd, 1H, J=14.0, 4.0), 2.96 (t, 2H, J=6.6), 2.83 (dd, 1H, J=13.8, 9.0), 2.43 (s, 3H), 1.76 (s, 3H); low resolution MS (ES+)m/e 518.1 (MH$^+$).

Example 33

(2S)-2-{[(Z)-1-methyl-3-oxo-3-(3-thienyl)-1-propenyl]amino}-3-{4-[2-(5methyl-2-phenyl-1,3-oxazol-4-yl)ethoxy]phenyl}propanoic acid The title compound was prepared (as described above for the preparation of Example 2) from 428 mg (0.89 mmol) of Intermediate 45 (as the TFA salt) and 150 mg (0.89 mmol) of Intermediate 31 to yield 210 mg of Example 33: TLC (DCM/MeOH, 4/1): $R_f$=0.60; $^1$H NMR (DMSO-$d_6$, 400 MHz) δ11.8 (d, $_1$H, J=9.2), 7.88 (m, 3H), 7.42 (m, 5H), 7.08 (d, 2H, J=8.4), 6.78 (d, 2H, J=8.4), 5.39 (s, 1H), 4.12 (t, 2H, J=6.4), 4.01 (m, 1H), 3.23 (m, 1H), 3.09 (m, 1H), 2.86 (t, 2H, J=6.4), 2.69 (dd, 1H, J=13.6, 9.2), 2.31 (s, 3H), 1.60 (s, 3H); low resolution MS (ES+)m/e 517.1 (MH$^+$).

Example 34

(2S)-2-{[(Z)-1-methyl-3-oxo-3-(2-pyridinyl)-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 441 mg (0.92 mmol) of Intermediate 45 (as the TFA salt) and 150 mg (0.92 mmol) of Intermediate 35 to yield 240 mg of Example 34: TLC (DCM/MeOH, 4/1): $R_f$=0.46; $^1$H NMR (DMSO-$d_6$, 400 MHz) δ11.49 (d, 1H, J=9.2), 8.52 (d, 1H, J=4.8), 7.90 (m, 4H), 7.47 (m, 4H), 7.11 (d, 2H, J=8.4), 6.80 (d, 2H, J=8.4), 6.13 (s, 1H), 4.12 (m, 3H), 3.16 (m, 2H), 2.87 (t, 2H, J=6.4), 2.77 (dd, 1H, J=13.6, 9.2), 2.34 (s, 3H), 1.71 (s, 3H); low resolution MS (ES−)m/e 510.1 (M-H).

Example 35

(2S)-2-{[(Z)-1-ethyl-3-(4-fluorophenyl)-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 100 mg (0.27 mmol) of Intermediate 45 and 49 mg (0.27 mmol) of Intermediate 32 to yield 83 mg of Example 35: TLC (EtOAc/MeOH (7:3): $R_f$=0.28; $^1$H NMR (DMSO-$d_6$, 400 MHz) δ11.38 (d, 1H, J=7.00), 7.84 (m. 4H), 7.45 (m, 3H), 7.16 (t, 2H, J=8.72), 7.09 (d, 2H, J=7.69), 6.77 (d, 2H, J=7.69), 5.49 (s, 1H), 4.11 (m, 2H), 4.01(m, br, 1H), 3.13 (m, 1H), 2.86 (m, 2H), 2.72 (s, br, 1H), 2.30 (s, 3H), 1.62 (s, 3H); low resolution MS (ES+) m/e 529 (MH$^+$); RP-HPLC (Vydac C-18, 25 cm×4.6 mm; 30–100% CH$_3$CN in H$_2$O) with 0.1% HCO$_2$H buffer: 30 minutes; 1 mL/min: $t_r$=20.10 min ($t_o$=1.53).

Example 36

(2S)-2-{[(Z)-1-methyl-3-oxo-3-phenyl-1-propenyl]amino}-3-{4-[2-(5-methyl-2-phenyl-1,3-thiazol-4-yl)ethoxy]phenyl}propanoic acid The title compound was prepared (as described above for the preparation of Example 2) from 0.5 g (1.31 mmol) of Intermediate 46 and 215 mg (1.31 mmol) of benzoyl acetone and 260 μL (1.31 mmol) of dicycylohexylamine (replacing TEA) to yield a total of 245 mg of Example 36 as a dull yellow solid. TLC (EtOAc/MeOH (3:1): $R_f$=0.56; $^1$H NMR (DMSO-$d_6$, 400 MHz) δ11.4 (d, 1H, J=9.1), 7.81 (m, 2H), 7.75 (m, 2H), 7.42 (m, 3H), 7.36 (m, 3H), 7.0 (d, 2H, J=8.4), 6.78 (d, 2H, J=8.6), 5.51 (s, 1H), 4.55 (m, 1H), 4.20 (t, 2H, J=6.7), 4.0 (br s, 1H), 3.14–3.04 (m, 3H), 2.7 (m, 1H), 2.38 (s, 3H), 1.68 (s, 3H) ; low resolution MS (ES+)m/e 527.1 (MH$^+$).

Example 37

(2S)-2-{[(Z)-3-(2-fluorophenyl)-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 100 mg (0.27 mmol) of Intermediate 45 and 58 mg (0.32 mmol) of Intermediate 20 to yield 55 mg of Example 37: TLC (EtOAc/MeOH (7:3): $R_f$=0.25; $^1$H NMR (DMSO-$d_6$, 400 MHz) δ11.42 (d, 1H, J=8.93), 7.95 (m. 2H), 7.70 (dd, 1H, J=1.78, 7.69), 7.51 (m, 4H), 7.23 (m, 4H), 6.88 (d, 2H, J=8.50), 5.36 (s, 1H), 4.22 (m, 2H), 4.16 (brs, 1H), 3.18 (m, 1H), 2.94 (m, 2H), 2.84 (m, 1H), 2.40 (s, 3H), 1.70 (s, 3H); low resolution MS (ES−)m/e 545.1 (M-H); RP-HPLC (Vydac C-18, 25 cm×4.6 mm; 30–100% CH$_3$CN in H$_2$O) with 0.1% HCO$_2$H buffer: 30 minutes; 1 mL/min: $t_r$=19.47 min ($t_o$=1.43).

Example 38

(2S)-2-{[(Z)-3-(2,3-difluorophenyl)-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 12) from 120 mg (0.33 mmol) of Intermediate 45 and 59 mg (0.33 mmol) of Intermediate 40 to yield 32 mg (18% yield) of Example 38: TLC (DCM/MeOH (4:1): $R_f$=0.72; $^1$H NMR (DMSO-$d_6$, 300 MHz) δ11.43 (d, 1H, J=9.8), 7.97 (m, 2H), 7.56 (m, 5 h), 7.28 (m, 1H), 7.19 (d, 2H, J=8.0) 6.91 (d, 2H, J=8.0), 5.34 (s, 1H), 4.21 (m, 3H), 3.21 (m, 2H), 2.98 (t, 2H, J=6.6), 2.84 9 m, 1H), 2.40 (s, 3H), 1.78 (s, 3H); low resolution MS (ES+)m/e 547 (MH$^+$).

Example 39

(2S)-2-{[(Z)-3-(2-hydroxyphenyl)-1-methyl-3-oxo-1-propenyl]amino}-3-{4-[2-(5-methyl-2-phenyl-1,3-oxazol-4-yl)ethoxy]phenyl}propanoic acid A solution of 100 mg (0.27 mmol) of Intermediate 45 and 58 mg (0.33 mmol) of 2-(acetoacetyl)phenol (Aldrich Chemical Co.) in 5.0 mL MeOH , 1.0 mL trimethyl orthoformate, and 4A sieves (50 mg) was refluxed at 80° C. for 16 h. The reaction solution was concentrated and purified by silica gel flash column chromatography using DCM/MeOH 20/1 to 10/1 as eluent to afford 135 mg of Example 39: TLC (DCM/MeOH (10:1): $R_f$=0.32; $^1$H NMR (DMSO-$d_6$) δ11.16 (d, 1H, J=8.72), 7.96 (m, 2H), 7.78 (m, 1H), 7.54 (m, 3H), 7.33 (m, 1H), 7.20 (m, 2H), 6.84 (m, 4H), 5.69 (s, 1H), 4.26 (m, 2H), 4.17 (br s, 1H), 3.20 (dd, 1H, J=3.93, 13.67), 2.95 (m, 2H), 2.81 (m, 1H), 2.40 (s, 3H), 1.75 (s, 3H); low resolution MS (ES+) m/e 527.0 (MH$^+$); RP-HPLC (Vydac C-18, 25 cm×4.6 mm; 50–100% CH$_3$CN in H$_2$O) with 0.1% HCO$_2$H buffer: 30 minutes; 1 mL/min: $t_f$=15.97 min ($t_o$=1.43).

Example 40

(2S)-3-{4-[2-(5-methyl-2-phenyl-1,3-oxazol-4-yl)ethoxy]phenyl}-2-{[(Z)-3-oxo-3-phenyl]-1-propyl-1-propenyl]amino}propanoic acid The title compound was prepared as described above for the preparation of Example 2, from 1.0 g (2.05 mmol) of Intermediate 45 (as the TFA salt) and 0.8 g (4.2 mmol) of Intermediate 17 to yield 400 mg of Example 40 as a white solid: $^1$H NMR (DMSO-$d_6$, 400 MHz) δ11.55 (d, 1H, J=9.6), 7.87 (m, 2H), 7.75 (m, 2H), 7.45 (m, 3H), 7.35 (m, 3H), 7.10 (d, 2H, J=8.6), 6.80 (d, 2H, J=8.5), 5.52 (s, 1H), 4.12 (t, 2H, J=6.6), 4.07 (m, 1H), 3.21 (dd, 1H, J=13.7, 3.7), 2.85 (t, 2H, J=6.5), 2.73(dd, 1H, J=13.7, 8.6), 2.3 (s, 3H) 1.90 (m, 2H), 1.4–1.25 (m, 2H), 0.76 (t, 3H, J=7.4); low resolution MS (ES+)m/e 539.2 (MH$^+$).

Example 41

(2S)-2-{[(Z)-3-(4-methoxyphenyl)-1-methyl-3-oxo-1-propenyl]amino}-3-{4-[2-(5-methyl-2-phenyl-1,3-oxazol-4-yl)ethoxy]phenyl}propanoic acid The title compound was prepared as described above for the preparation of Example 2) from 100 mg (0.27 mmol) of Intermediate 45 and 52 mg (0.27 mmol) of Intermediate 22 to yield 126 mg of Example 41. TLC (EtOAc/MeOH (7:3): $R_f$=0.44; $^1$H NMR (DMSO-$d_6$, 400 MHz) δ11.30 (d, 1H, J=7.00), 7.87 (m. 2H), 7.73 (d, 2H, J=8.72), 7.45 (m, 3H), 7.10 (d, 2H, J=8.37), 6.88 (d, 2H, J=8.89), 6.77 (d, 2H, J=8.37), 5.74 (s, 1H), 4.11 (m, 2H), 4.01(m, br, 1H), 3.13 (m, 1H), 2.86 (m, 2H), 2.72 (m, 1H), 2.31 (s, 3H), 1.65 (s, 3H); low resolution MS (ES−) m/e 539 (M-H); RP-HPLC (Vydac C-18, 25 cm×4.6 mm; 10–50% CH$_3$CN in H$_2$O) with 0.1% HCO$_2$H buffer: 30 minutes

Example 42

(2S)-3-(4-{2-[2-(4-methoxyphenyl)-5-methyl-1,3-oxazol-4-yl]ethoxy}phenyl)-2-{[(Z)-1-methyl-3-oxo-3-phenyl-1-propenyl]amino}propanoic acid The title compound was prepared (as described above for the preparation of Example 2) from 75 mg (0.19 mmol) of Intermediate 49 and 31 mg (0.19 mmol) of benzoylacetone to yield 30 mg of Example 42: TLC (DCM/MeOH (4:1): $R_f$=0.45; $^1$H NMR (DMSO-$d_6$, 400 MHz) δ11.5 (d, 1H, J=9.1), 7.89 (d, 2H, J=8.8), 7.84 (m, 2H), 7.45 (m, 3H), 7.18 (d, 2H, J=8.4); 7.09 (d, 2H, J=8.8), 6.88 (d, 2H, J=8.6), 5.63 (s, 1H), 4.2 (t, 2H, J=6.5), 4.1 (m, 1H), 3.86 (s, 3H), 3.2 (m, 1H), 2.93 (t, 2H, J=6.6), 2.83 (dd, 1H, J=13.2, 6.4), 2.37 (s, 3H), 1.76 (s, 3H); low resolution MS (ES−)m/e 539.2 (MH−).

Example 43

(2S)-2-{[(Z)-3-cyclohexyl-1-methyl-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 428 mg (0.89 mmol) of Intermediate 45 (as the TFA salt) and 150 mg (0.89 mmol) of Intermediate 33 to yield 245 mg (53% yield) of Example 43 as a solid beige-colored glass: TLC (DCM/MeOH (4:1): $R_f$=0.69; $^1$H NMR (DMSO-$d_6$, 400 MHz) δ10.79 (d, 1H, J=9.0), 7.89 (m, 2H), 7.50–7.41 (m, 3H), 7.05 (d, 2H, J=8.4), 6.77 (d, 2H, J=8.4), 4.7 (s, 1H), 4.12 (t, 2H, J=6.5), 3.9 (br s, 1H), ), 3.04 (dd, 1H, J=13.6, 4.0), 2.87 (t, 2H, J=6.5), 2.64 (dd, 1H, J=13.6, 8.9), 2.32 (s, 3H), 1.9 (m, 1H), 1.6 (m, 4H), 1.5 (s, 3H), 1.25–1.05 (m, 4H): low resolution MS (ES+)m/e 517.3 (MH$^+$).

Example 44

(2S)-3-(4-{2-[2-(4-isopropoxyphenyl)-5-methyl-1,3-oxazol-4-yl]ethoxy}phenyl)-2-{[(Z)-1-methyl-3-oxo-3-phenyl-1-propenyl]amino}propanoic acid The title compound was prepared (as described above for the preparation of Example 2) from 75 mg (0.18 mmol) of Intermediate 51 and 32 mg (0.194 mmol) of benzoylacetone to yield 55 mg of Example 44: TLC (DCM/MeOH (4:1): $R_f$=0.50; $^1$H NMR (DMSO-$d_6$, 400 MHz) δ11.5 (d, 1H, J=9.0), 7.85 (m, 4H), 7.45 (m, 3H), 7.18 (d, 2H, J=8.4); 7.06 (d, 2H, J=8.8), 6.87 (d, 2H, J=8.5), 5.82 (s, 1H), 4.74 (m, 1H), 4.19 (t, 2H, J=6.6), 4.1 (m, 1H), 3.19 (m, 1H), 2.92 (t, 2H, J=6.6), 2.81 (dd, 1H, J=13.9. 9.1), 2.36 (s, 3H), 1.74 (s, 3H), 1.34 (d, 6H, J=6.0); low resolution MS (ES−)m/e 567.2 (M-)

Example 45

(2S)-2-{[(Z)-1-heptyl-3-oxo-3-phenyl-1-propenyl]amino}-3-{4-[2-(5-methyl-2-phenyl-1,3-oxazol-4-yl)ethoxy]phenyl}propanoic acid The title compound was prepared as described above for the preparation of Example 2, from 102 mg (0.28 mmol) of Intermediate 45 and 69 mg (0.28 mmol) of Intermediate 19 to yield 77 mg of Example 45: TLC (EtOAc/MeOH , 713): $R_f$=0.56; $^1$H NMR (DMSO-$d_6$, 400 MHz) δ11.55 (d, 1H, J=9.6), 7.86 (d, 2H, J=6.8), 7.76 (d, 2H, J=6.4), 7.46. (m, 3H), 7.38 (m, 3H), 7.10 (d, 2H, J=8.4), 6.78 (d, 2H, J=8.4), 5.5 (s, 1H), 4.10 (t, 2H, J=6.6), 4.0 (m, 1H), 3.16 (m, 1H), 2.86 (t, 2H, J=6.5), 2.69 (dd, 1H, J=13.6, 9.6), 2.31 (s, 3H), 1.87 (m, 2H), 1.25–1.1 (m, 10H), 0.78 (t, 3H, J=6.8); low resolution MS (ES+)m/e 595.1 (MH$^+$).

Example 46

(2S)-2-{[(Z)-1-methyl-3-(3-methylphenyl)-3-oxo-1-propenyl]amino}-3-{4-[2-(5-methyl-2-phenyl-1,3-oxazol-4-yl)ethoxy]phenyl}propanoic acid The title compound was prepared (as described above for the preparation of Example 2) from 100 mg (0.27 mmol) of Intermediate 45 and 48 mg (0.27 mmol) of Intermediate 21 to yield 104 mg of Example 46. $^1$H NMR (DMSO-$d_6$, 400 MHz) δ11.47 (d, 1H, J=9.06), 7.95 (m. 2H), 7.65 (m, 2H), 7.54 (m, 3H), 7.31 (m, 2H), 7.19 (d, 2H, J=8.51), 6.88 (d, 2H, J=8.51), 5.64 (s, 1H), 4.23 (m, 1H), 4.23 (m, 3H), 3.21 (m, 1H), 2.96 (m, 2H), 2.86 (m, 1H), 2.60 (s, 3H), 1.80 (s, 3H); low resolution MS (ES) m/e 525.2 (MH$^+$); RP-HPLC (Vydac C-18, 25 cm×4.6 mm; 50–100% CH$_3$CN in H$_2$O) with 0.1% HCO$_2$H buffer 30 minutes; 1 mL/min: $t_f$15.57 min ($t_o$=1.43).

Example 47

(2S)-2-{[(Z)-1-ethyl-3-oxo-3-phenyl-1-propenyl]amino}-3-(4-{2-[2-(4-methoxyphenyl)-5-methyl-1,3-oxazol-4-yl]ethoxy}phenyl)propanoic acid The title compound was prepared (as described above for the preparation of Example 2) from 100 mg (0.25 mmol) of Intermediate 49 and 45 mg (0.25 mmol) of Intermediate 16 to yield 95 mg (68% yield) of Example 47 as a solid: TLC $R_f$=0.2–0.3 (slight streak, 4/1, CH$_2$Cl$_2$/MeOH); $^1$H NMR (DMSO-$d_6$, 400 MHz) δ11.5 (d, 1H, J=9.0), 7.85 (m, 4H), 7.45 (m, 3H), 7.18 (d, 2H, J=8.4); 7.06 (d, 2H, J=8.8), 6.87 (d, 2H, J=8.5), 5.82 (s, 1H), 4.74 (m, 1H), 4.19 (t, 2H, J=6.6), 4.1 (m, 1H), 3.19 (m, 1H), 2.92 (t, 2H, J=6.6), 2.81 (dd, 1H, J=13.9, 9.1), 2.36 (s, 3H), 1.74 (s, 3H), 1; low resolution MS (ES+)m/e 555.1 (MH$^+$);

Example 48

(2S)-3-{4-[2-(5-methyl-2-phenyl-1,3-oxazol-4-yl)ethoxy]phenyl}-2{[(Z)-3-oxo-3-phenyl-1-(trifluoromethyl)-1-propenyl]amino}propanoic acid The title compound was prepared (as described above for the preparation of Example 12) from 1.3 g (3.55 mmol) of Intermediate 45 and 0.7 g (3.55 mmol) of Intermediate 44 to yield 0.84 g (42% yield) of Example 48 as a solid: TLC (DCM/MeOH (4:1): $R_f$=0.55; $^1$H NMR (DMSO-$d_6$, 300 MHz) δ10.99 (s, 1H), 7.94 (m, 4H), 7.68 (m, 6H), 7.14 (d, 2H, J=8.4), 6.84 (d, 2H, J=8.4), 6.21 (s, 1H), 4.19 (m, 3H), 3.17 (m, 1H), 2.92–2.85 (m, 3H), 2.36 (s, 3H); low resolution MS (ES+)m/e 565.0 (MH$^+$).

Example 49

(2S)-3-{4-[2-(5-methyl-2-phenyl-1,3-thiazol-4-yl)ethoxy]phenyl}-2{[(Z)-3-oxo-3-phenyl-1-(trifluoromethyl)-1-propenyl]amino}propanoic acid The title compound was prepared (as described above for the preparation of Example 12) from 120 mg (0.31 mmol) of Intermediate 46 and 62 mg (0.31 mmol) of Intermediate 44 to yield 78 mg of Example 49: TLC (DCM/MeOH (4:1): $R_f$=0.58; $^1$H NMR (DMSO-$d_6$, 300 MHz) δ10.92 (br s, 1H), 7.88 (d, 2H, J=), 7.81 (m, 2H), 7.56–7.37 (m, 6H), 7.01 (d, 2H, J=8.5), 6.78 (d, 2H, J=8.3), 6.13 (s, 1H), 4.19 (t, 2H, J=6.5), 4.10 (br s, 1H), 3.15–3.11 (m, 1H), 3.05 (t, 2H, J=6.6), 2.87 (dd, 1H, J=13.7, 7.7), 2.37 (s, 3H); low resolution MS (ES+)m/e 581.0 (MH$^+$).

Example 50

(2S)-2-({(Z)-1-ethyl-3-oxo-3-[4-(trifluoromethyl)phenyl]-1-propenyl}amino)-3-(4-{2-[2-(4-fluorophenyl)-5-methyl-1,3-oxazol-4-yl]ethoxy}phenyl)propanoic acid The title compound was prepared (as described above for the preparation of Example 2) from 150 mg (0.39 mmol) of Intermediate 46 and 95 mg (0.39 mmol) of Intermediate 25 to yield 79 mg (33% yield) of Example 50: TLC (DCM/MeOH, 4/1): $R_f$=0.62; $^1$H NMR (DMSO-$d_6$, 300 MHz) δ11.59 (d, 1H, J=9.0), 7.97–7.88 (m, 4H), 7.72 (d, 2H, J=8.4), 7.29 (t, 2H, J=9.0), 7.11 (d, 2H, J=8.4), 6.78 (d, 2H, J=8.4), 5.59 (s, 1H), 4.11 (m, 3H), 3.17 (m, 2H), 2.85 (t, 2H, J=6.3), 2.77 (m, 1H), 2.29 (s, 3H), 2.03 (m, 2H), 0.91 (t, 3H, J=7.5); low resolution MS (ES$^+$)m/e 611.2 (MH$^+$).

Example 51

(2S)-2-({(Z)-1-ethyl-3-oxo-3-[4-(trifluoromethyl) phenyl]-1-propenyl}amino)-3-(4-{2-[2(4-isopropoxyphenyl)-5-methyl-1,3-oxazol-4-yl] ethoxy}phenyl)propanoic acid The title compound was prepared (as described above for the preparation of Example 2) from 151 mg (0.39 mmol) of Intermediate 51 and 92 mg (0.39 mmol) of Intermediate 25 to yield 91 mg (36% yield) of Example 51: TLC (DCM/MeOH, 4/1): R$_f$=0.60; $^1$H NMR (DMSO-d$_6$, 300 MHz) δ11.6 (d, 1H, J=9.6), 7.96 (d, 2H, J=8.1), 7.81–7.70 (m, 4H), 7.10 (d, 2H, J=8.4), 6.96 (d, 2H, J=8.7), 6.78 (d, 2H, J=8.4), 5.59 (s, 1H), 4.62 (sept, 1H, J=6.0), 4.13 (m, 3H), 3.16 (m, 1H), 2.84–2.72 (m, 3H), 2.26 (s, 3H), 2.05–1.96 (m, 2H), 1.24 (d, 6H, J=6.0), 0.91 (t, 3H, J=7.5); low resolution MS (ES$^+$)m/e 651.3 (MH$^+$).

Example 52

(2S)-2-({(Z)-1-ethyl-3oxo-3-[4-(trifluoromethyl) phenyl]-1-propenyl}amino)3-(4-{2-[2-(4-methoxyphenyl)-5-methyl-1,3-oxazol-4-yl] ethoxy}phenyl)propanoic acid The title compound was prepared (as described above for the preparation of Example 2) from 150 mg (0.38 mmol) of Intermediate 49 and 93 mg (0.38 mmol) of Intermediate 25 to yield 45 mg (19% yield) of Example 52: TLC (DCM/MeOH, 4/1): R$_f$=0.63; $^1$H NMR (DMSO-d$_6$, 300 MHz) δ11.6 (d, 1H, J=9.6), 7.96 (d, 2H, J=8.1), 7.81–7.70 (m, 4H), 7.11 (d, 2H, J=8.4), 7.0 (d, 2H, J=8.7), 6.78 (d, 2H, J=8.4), 5.6 (s, 1H), 4.18–4.07 (m, 3H), 3.77 (s, 3H), 3.17 (m, 1H), 2.85–2.72 (m, 3H), 2.26 (s, 3H), 2.05–1.96 (m, 2H), 0.91 (t, 3H, J=7.5); low resolution MS (ES$^+$)m/e 623.2 (MH$^+$).

Example 53

(2S)-3-(4-{2-[2-(4-fluorophenyl)-5-methyl-1,3-oxazol-4-yl]ethoxy}phenyl)-2-{[(Z)-3-oxo-3-phenyl-1-(trifluoromethyl)-1-propenyl] amino}propanoic acid The title compound was prepared (as described above for the preparation of Example 12) from 203 mg (0.53 mmol) of Intermediate 46 and 130 mg (0.63 mmol) of Intermediate 44 to yield 154 mg (50% yield) of Example 53: TLC (DCM/MeOH, 4/1): R$_f$=0.65; $^1$H NMR (DMSO-d$_6$, 400 MHz) δ11.5 (d, 1H, J=8.9), 7.95 (d, 2H, J=7.2), 7.77 (d, 2H, J=8.7), 7.72 (d, 2H, J=8.2), 7.1 (d, 2H, J=8.4), 6.97 (d, 2H, J=8.9), 6.79 (d, 2H, J=8.5), 5.58 (s, 1H), 4.65 (m, 1H), 4.11 (t, 2H, J=6.5), 4.1 (m, 1H), 3.16 (dd, 1H, J=13.7, 3.6), 2.84 (t, 2H, J=6.5), 2.74 (dd,1H, 13.7, 9.0), 2.28 (s, 3H), 1.67 (s, 3H), 1.25 (d, 6H, J=6.0); low resolution MS (ES$^+$)m/e 637.1 (MH$^+$)

Example 54

(2S)-2-{[(Z)-1-methyl-3-oxo-3-phenyl-1-propenyl] amino}-3-{4-[(5-methyl-2-phenyl-1,3-oxazol-4-yl) methoxy]phenyl}propanoic acid The title compound was prepared (as described above for the preparation of example 1) from a suspension of 113 mg (0.32 mmol) of Intermediate 54 and 52 mg (0.32 mmol) of benzoylacetone to yield 44 mg (28%) of example 54: TLC (DCM/MeOH, 4/1): R$_f$=0.55; $^1$H NMR (DMSO-d$_6$, 300 MHz) δ11.43 (d, 1H, J=9.0), 7.92–7.88 (m, 2H), 7.8 (m, 2H), 7.48 (m, 3H), 7.38–7.38 (m, 3H), 7.16 (d, 2H, J=8.4), 6.9 (d, 2H, J=8.4), 5.53 (s, 1H), 4.91 (s, 1H), 4.15 (m, 1H), 3.2 (m, 2H), 2.83–2.74 (m, 1H), 2.37 (s, 3H), 1.67 (s, 3H); low resolution MS (ES$^+$)m/e 497.07 (MH$^+$).

Example 55

(2S)-3-{4-[2-(5-ethyl-2-phenyl-1,3-oxazol-4-yl) ethoxy]phenyl}-2-{[(Z)-1-methyl-3-oxo-3-phenyl-1-propenyl]amino}propanoic acid The title compound was prepared (as described above for the preparation of example 1) from a suspension of 205 mg (0.54 mmol) of Intermediate 52 and 87 mg (0.54 mmol) of benzoylacetone to yield 145 mg (51%) of example 55: TLC (DCM/MeOH, 4/1): R$_f$=0.60; $^1$H NMR (DMSO-d$_6$, 300 MHz) δ11.42 (d, 1H, J=9.0), 7.89–7.86 (m, 2H), 7.77–7.74 (m, 2H), 7.48–7.32 (m, 6H), 7.11 (d, 2H, J=8.4), 6.77 (d, 2H, J=8.4), 5.53 (s, 1H), 4.1 (t, 1H, J=6.3), 3.2–3.14 (m, 2H), 2.86 (t, 2H, J=6.3), 2.79–2.74 (m, 1H), 2.67 (q, 2H, J=7.5), 1.65 (s, 3H), 1.17 (t, 3H, J=7.5); low resolution MS (ES$^+$) m/e 525.2 (MH$^+$).

Example 56

(2S)-2-{[(Z)-1-methyl-3-oxo-3-phenyl-1-propenyl] amino}-3-{4-[2-(2-phenyl-5-propyl-1,3-oxazol-4-yl) ethoxy]phenyl}propanoic acid The title compound was prepared (as described above for the preparation of example 1) from a suspension of 204 mg (0.52 mmol) of Intermediate 53 and 84 mg (0.52 mmol) of benzoylacetone to yield 137 mg (49%) of example 56: TLC (DCM/MeOH, 4/1): R$_f$=0.60; $^1$H NMR (DMSO-d$_6$, 300 MHz) δ11.42 (d, 1H, J=9.0), 7.89–7.86 (m, 2H), 7.77–7.74 (m, 2H), 7.49–7.32 (m, 6H), 7.11 (d, 2H, J=8.4), 6.77 (d, 2H, J=8.4), 5.53 (s, 1H), 4.1 (t, 1H, J=6.3), 3.19–3.13 (m, 2H), 2.86 (t, 2H, J=6.3), 2.78–2.71 (m, 1H), 2.64 (t, 1H, J=7.2), 1.65–1.54 (m, 5H), 0.88 (t, 3H, J=7.5); low resolution MS (ES$^+$)m/e 539.19 (MH$^+$).

Example 57

(2S)-2-{[(Z)-1-methyl-3-oxo-3-phenyl-1-propenyl] amino}-3-{4-[3-(5-methyl-2-phenyl-1,3-oxazol-4-yl) propoxy]phenyl}propanoic acid The title compound was prepared (as described above for the preparation of example 1) from a suspension of 205 mg (0.54 mmol) of Intermediate 55 and 88 mg (0.54 mmol) of benzoylacetone to yield 142 mg (50% yield) of example 57: TLC (DCM/MeOH, 4/1): R$_f$=0.66; $^1$H NMR (DMSO-d$_6$, 300 MHz) δ11.44 (d, 1H, J=9.0), 7.88–7.85 (m, 2H), 7.78–7.75 (m, 2H), 7.49–7.43 (m, 3H), 7.37–7.32 (m, 3H), 7.12 (d, 2H, J=8.4), 6.78 (d, 2H, J=8.4), 5.54 (s, 1H), 4.13 (m, 1H), 3.87 (t, 1H, J=6.0), 3.22–3.16 (m, 1H), 2.77 (d, 1H, J=14.4, 9.2), 2.56 (t, 2H, J=7.2), 2.22 (s, 3H), 2.00–1.93 (m, 2H), 1.66 (s, 3H); low resolution MS (ES$^+$)m/e 525.15 (MH$^+$).

Example 58

(2S)-3-{4-[2-(5-ethyl-2-phenyl-1,3-oxazol-4-yl) ethoxy]phenyl}-2-{[(Z)-3-oxo-3-phenyl-1-(trifluoromethyl)-1-propenyl]amino}propanoic acid A mixture of 100 mg (0. 26 mmol, 1.0 equivalent) of Intermediate 52, 110 mg (0.39 mmol, 1.5 equivalents) of Intermediate 44, and 0.14 mL (0.8 mmol, 3.0 equivalents) of DIEA in 2 mL of MeOH was stirred for 2.5 hours at ambient temperature (22° C.). The solvent was evaporated under reduced pressure. The residue was taken into EtOAc (20 mL) and washed with 10 mL 0.1 N HCl solution and 10 mL brine. The organics were dried over $Na_2SO_4$, filtered, concentrated, and the residue purified directly by silica gel chromatography. Elution with 10%–20% MeOH in EtOAc gave 55 mg (36% yield) of the title compound as a solid after drying under vacuum for several hours: TLC (DCM/MeOH, 4/1): $R_f$=0.65; $^1$H NMR (DMSO-$d_6$, 400 MHz) δ10.95 (br s, 1H), 7.88–7.93 (m, 4H), 7.52–7.41 (m, 6H), 7.72 (d, 2H, J=8.2), 7.02 (d, 2H, J=8.4), 6.73 (d, 2H, J=8.5), 6.06 (s, 1H), 4.09 (t, 2H, J=6.5), 3.99 (m, 1H), 3.0 (m, 1H, NH), 2.86–2.79 (m, 4H), 2.66 (q, 2H, 7.5), 1.15 (t, 3H, J=7.5); low resolution MS (ES+)m/e 579.08 (MH$^+$)

Example 59

(2S)-3-{4-[3-(5-methyl-2-phenyl-1,3-oxazol-4-yl) propoxy]phenyl}-{[(Z)-3-oxo-3-phenyl-1-(trifluoromethyl)-1-propenyl]amino}propanoic acid The title compound was prepared (as described above for the preparation of Example 58) from 100 mg (0.26 mmol) of Intermediate 55 and 110 mg (0.39 mmol) of Intermediate 44 to yield 65 mg (42% yield) of Example 59: TLC (DCM/MeOH, 4/1): $R_f$=0.58; $^1$H NMR (DMSO-$d_6$, 400 MHz) δ10.74 (d, 1H, J=9.4), 7.90 (d, 2H, J=7.5), 7.86–7.82 (m, 2H), 7.54 (m, 1H), 7.48–7.40 (m, 5H), 7.09 (d, 2H, J=8.4), 6.81 (d, 2H, J=8.4), 6.25 (s, 1H), 4.3 (br s, 1H), 3.89 (t, 2H, J=6.1), 3.09 (dd, 1H, J=14.0, 4.8), 2.96 (dd, 1H, 14.0, 7.9). 2.2 (s, 3H), 2.0–1.92 (m, 2H); low resolution MS (ES+)m/e 579.08 (MH$^+$)

Example 60

(2S)-3-{4-[2-(5-ethyl-2-phenyl-1,3-thiazol-4-yl) ethoxy]phenyl}-2-{[(Z)-3-oxo-3-phenyl-1-(trifluoromethyl)-1-propenyl]amino}propanoic acid The title compound was prepared (as described above for the preparation of Example 58) from 180 mg (0.35 mmol) of Intermediate 57 (as its TFA salt) and 148 mg (0.53 mmol) of Intermediate 44 to yield 113 mg (54% yield) of Example 60: TLC (DCM/MeOH, 85/15): $R_f$=0.50; $^1$H NMR (DMSO -$d_6$, 300 MHz) δ10.72 (d, 1H, J=10.3), 7.94 (d, 2H, J=7.3), 7.87–7.83 (m, 2H), 7.67–7.39 (m, 5H), 7.13 (d, 2H, J=8.6), 6.86 (d, 2H, J=8.5), 6.32 (s, 1H, 4.26 (t, 2H, J=6.5), 3.17–3.01 (m, 4H), 2.81 (q, 2H, J=7.4), 1.22 (t, 3H, J=7.4); low resolution MS (ES+)m/e 594.9 (MH$^+$)

Example 61

(2S)-3-(4-{2-[5-ethyl-2-(4-fluorophenyl)-1,3-oxazol-4-yl]ethoxy}phenyl)-2-{[(Z)-3-oxo-3-phenyl-1-trifluoromethyl)-1-propenyl]amino}propanoic acid The title compound was prepared (as described above for the preparation of Example 58) from 130 mg (0.26 mmol) of Intermediate 58, 106 mg (0.38 mmol) of Intermediate 44, and 0.14 mL diisopropylethylamine in 5 mL MeOH. The crude product was recrystallized from hot $CH_3CN$ to yield 67 mg (43% yield) of Example 61: TLC (DCM/MeOH, 85/15): $R_f$=0.44; $^1$H NMR (DMSO-$d_6$, 300 MHz) δ10.72 (d, 1H, J=10.3), 7.97–7.92 (m, 4H), 7.62–7.56 (m, 1H), 7.52–7.46 (m, 3H), 7.32 (t, 2H, J=8.7), 7.13 (d, 2H, J=8.6), 6.85 (d, 2H, J=8.6), 6.32 (s, 1H), 4.35 (m, 1H), 4.16 (t, 2H, J=6.5), 3.13 (dd, 1H, J=14.0, 4.8), 3.02 (dd, 1H, J=14.0, 7.7), 2.89 (t, 2H, J=6.5), 2.69 (q, 2H, J=7.4), 1.19 (t, 3H, J=7.5); low resolution MS (ES+)m/e 596.9 (MH$^+$).

Example 62

(2S)-3-(4-{3-[5-ethyl-2-(4-fluorophenyl)-1,3-oxazol-4-yl]propoxy}phenyl)-2{[(Z)-3-oxo-3-phenyl-1-trifluoromethyl)-1-propenyl]amino}propanoic acid The title compound was prepared (as described above for the preparation of Example 58) from 200 mg (0.38 mmol) of Intermediate 59, 127 mg (0.57 mmol) of Intermediate 44, and 0.2 mL diisopropylethylamine in 2.5 mL MeOH. The crude product was recrystallized from hot $CH_3CN$ to yield 106 mg (46% yield) of Example 62: TLC (DCM/MeOH, 4/1): $R_f$=0.61; $^1$H NMR (DMSO-$d_6$, 300 MHz) δ10.72 (d, 1H, J=10.2), 7.95–7.91 (m, 4H), 7.76–7.61 (m, 3H), 7.31 (t, 2H, J=8.7), 7.13 (d, 2H, J=8.1), 6.85 (d, 2H, J=8.4), 6.32 (s, 1H), 4.42–4.37 (m, 1H), 3.92 (t, 1H, J=5.7), 3.15–2.98 (m, 3H), 2.60–2.65 (m 4H), 2.0 (t, 2H, J=6.3), 1.10 (t, 3H, J=7.5); low resolution MS (ES$^+$)m/e 610.96 (MH$^+$).

Example 63

(2S)-3-(4-{2-[ethyl-2-4-fluorophenyl)-1,3-thiazol-4-yl]ethoxy}phenyl)-2{[(E)-3-oxo-3-phenyl-1-(trifluoromethyl)-1-propenyl]amino}propanoic acid The title compound was prepared (as described above for the preparation of Example 58) from 130 mg (0.25 mmol) of Intermediate 56, 103 mg (0.37 mmol) of Intermediate 44, and 0.17 mL diisopropylethylamine in 5 mL MeOH. The crude product was recrystallized from hot $CH_3CN$ to yield 110 mg (72% yield) of Example 63: TLC (DCM/MeOH, 85/15): $R_f$=0.45; $^1$H NMR (DMSO-$d_6$, 300 MHz) δ10.72 (d, 1H, J=10.2), 7.96–7.86 (m, 4H), 7.59 (m, 1H), 7.52–7.46 (m, 3H), 7.28 (t, 2H, J=8.8), 7.13 (d, 2H, J=8.6), 6.85 (d, 2H, J=8.5), 6.32 (s, 1H), 4.38 (m, 1H), 4.25 (t, 2H, J=6.5), 3.31–2.98 (m, 4H), 2.81 (q, 2H, J=7.4), 1.22 (t, 3H, J=7.4); low resolution MS (ES$^+$)m/e 612.9 (MH$^+$)

Example 64

(2S)-3-(4-{3-[5-ethyl-2-(4-fluorophenyl)-1,3-oxazol-4-yl]propoxy}phenyl)-2-({(Z)-1-ethyl 3-oxo-3-[4-(trifluoromethyl)phenyl]-1-propenyl}amino) propanoic acid The title compound was prepared (as described above for the preparation of Example 2) from 95 mg (0.18 mmol) of Intermediate 59 (TFA Salt), 44 mg (0.18 mmol) of Intermediate 25, and 0.055 mL triethylamine in MeOH (1.5 mL) and trimethylorthoformate (0.5 mL) to yield 44 mg (38% yield) of Example 64 after silica gel chromatography (5%–15% MeOH in DCM elution): TLC (DCM/MeOH, 4/1): $R_f$=0.53; $^1$H NMR (DMSO-$d_6$, 300 MHz) δ11.63 (d, 1H, J=9.3), 7.99–7.89 (m, 4H), 7.73 (d, 2H, J=8.1), 7.30 (t, 2H, J=8.7), 7.13 (d, 2H, J=8.1), 6.79 (d, 2H, J=8.1), 5.62 (s, 1H), 4.20 (m, 1H), 3.87 (m, 2H), 3.20 (m, 2H), 2.77 (m, 2H), 2.61–2.54 (m, 4H), 2.05–1.96 (m, 4H), 1.10 (t, 3H, J=7.2), 0.92 (t, 3H, J=7.5); low resolution MS (ES$^+$)m/e 638.93 (MH$^+$).

Example 65

(2S)-2-({(Z)-1-ethyl-3-oxo-3-[4-(trifluoromethyl) phenyl]-1-propenyl}amino)-3-{4-[3-(5-ethyl-2-phenyl-1,3-oxazol-4-yl)propoxy]phenyl}propanoic acid The title compound was prepared (as described above for the preparation of Example 2) from 50 mg (0.13 mmol) of Intermediate 60, 31 mg (0.13 mmol) of Intermediate 25, and 0.044 mL triethylamine in MeOH (1.0 mL) and trimethylorthoformate (0.5 mL) to yield 22 mg (28% yield) of Example 65 after silica gel chromatography (5%–15% MeOH in DCM elution): TLC (DCM/MeOH, 4/1): $R_f$=0.50; $^1$H NMR (DMSO-$d_6$, 300 MHz) δ11.70 (d, 1H, J=9.6), 8.05 (d, 2H, J=7.8), 7.95 (d, 2H, J=7.8), 7.81 (d, 2H, J=8.1), 7.55–7.52 (m, 3H), 7.20 (d, 2H, J=8.4), 6.86 (d, 2H, J=8.4), 5.69 (s, 1H), 4.28–4.2 1H), 3.96 (d, 2H, J=6.0), 3.28–3.20 (m, 2H), 2.89–2.81 (m, 1H), 2.72–2.63 (m, 4H), 2.05–1.96 (m, 4H), 1.18 (t, 3H, J=7.5), 0.99 (t, 3H, J=7.5); low resolution MS (ES$^+$)m/e 620.98 (MH$^+$).

Example 66

(2S)-3-(4-{3-[5-ethyl-2-(4-fluorophenyl)-1,3-oxazol-4-yl]propoxy}phenyl)-2-({(Z)-1-methyl-3-oxo-3-[4-(trifluoromethyl)phenyl]-1-propenyl}amino)propanoic acid The title compound was prepared (as described above for the preparation of Example 2) from 90 mg (0.17 mmol) of Intermediate 59, 40 mg (0.17 mmol) of Intermediate 24, and 0.05 mL triethylamine in MeOH (1.5 mL) and trimethylorthoformate (0.5 mL) to yield 54 mg (51% yield) of Example 66 after silica gel chromatography (5%–15% MeOH in DCM): TLC (DCM/MeOH, 4/1): $R_f$=0.60; $^1$H NMR (DMSO-$d_6$, 300 MHz) δ11.53 (d, 1H, J=9.0), 7.98–7.90 (m, 4H), 7.73 (d, 2H, J=8.4), 7.30 (t, 2H, J=8.7), 7.13 (d, 2H, J=8.4), 6.79 (d, 2H, J=8.4), 5.61 (s, 1H), 4.23–4.19 (m, 1H), 3.89 (t, 2H, J=6.0), 3.22–3.17 (m, 2H), 2.83–2.75 (m, 2H), 2.64–2.55 (m, 4H), 1.97 (t, 2H, J=6.3), 1.71 (s, 3H), 1.10 (t, 3H, J=7.5); low resolution MS (ES$^+$) m/e 625.15 (MH$^+$).

Example 67

(2S)-3-{4-[3-(5-ethyl-2-phenyl-1,3-oxazol-4-yl)propoxy]phenyl}-2-({(Z)-1-methyl-3-oxo-3-[4-(trifluoromethyl)phenyl]-1-propenyl}amino)propanoic acid The title compound was prepared (as described above for the preparation of Example 2) from 57 mg (0.14 mmol) of Intermediate 60, 33 mg (0.14 mmol) of Intermediate 24, and 0.042 mL triethylamine in MeOH (1.5 mL) and trimethylorthoformate (0.5 mL) to yield 24 mg (28% yield) of Example 67 after silica gel chromatography (5%–15% MeOH in DCM): TLC (DCM/MeOH, 4/1): $R_f$=0.62; $^1$H NMR (DMSO-$d_6$, 300 MHz) δ11.53 (d,1H, J=9.0), 7.97 (d, 2H, J=8.4), 7.89 (d, 2H, J=7.8), 7.73 (d, 2H, J=8.4), 7.46 (m, 3H), 7.97 (d, 2H, J=8.1), 6.79 (d, 2H, J=8.4), 5.62 (s, 1H), 4.25–4.19 (m, 1H), 3.90 (t, 2H, J=6.0), 3.21–3.15 (m, 1H), 2.58–2.83 (m, 5H), 1.98 (t, 2H, J=5.7), 1.72 (s, 3H), 1.11 (t, 3H, J=7.5); low resolution MS (ES$^+$)m/e 607.18 (MH$^+$).

Example 68

(2S)-3-{4-[3-(5-ethyl-2-phenyl-1,3-oxazol-4-yl)propoxy]phenyl}-2-{[(Z)-3-oxo-3-phenyl-1-(trifluoromethyl)-1-propenyl]amino}propanoic acid The title compound was prepared (as described above for the preparation of Example 58) from 100 mg (0.25 mmol) of Intermediate 60, 85 mg (0.38 mmol) of Intermediate 44, and 0.14 mL diisopropylethylamine in 2.0 mL MeOH. Attempted recrystallization from hot CH$_3$CN without success. Silica gel chromatography with MeOH/DCM (10%–20%) gave 68 mg (45% yield) of Example 68: TLC (DCM/MeOH, 4/1): $R_f$=0.60; $^1$H NMR (DMSO-$d_6$, 300 MHz) δ10.96 (br s, 1H), 7.90–7.87 (m, 4H), 7.54–7.46 (m, 6H), 7.07 (d, 2H, J=8.4), 6.78 (d, 2H, J=8.1), 6.12 (s, 1H), 4.11–4.03 (m, 1H), 3.89 (t, 2H, J=6.0), 3.12–3.07 (m, 1H), 2.91–2.83 (m, 1H), 2.66–2.57 (m, 4H), 1.98 (t, 2H, J=5.7), 1.11 (t, 3H, J=7.5); low resolution MS (ES$^+$)m/e 593.02 (MH$^+$).

Example 69

(2S)-3-{4-[(5-ethyl-2-phenyl-1,3-thiazol-4-yl)methoxy]phenyl}-2-{[(Z)-3-oxo-3-phenyl-1-trifluoromethyl)-1-propenyl]amino}propanoic acid The title compound was prepared (as described above for the preparation of Example 58) from 1.5 g (3.02 mmol) of Intermediate 62, 1.01 g (4.53 mmol) of Intermediate 44, and 1.6 mL diisopropylethylamine in 20 mL MeOH. Attempted recrystallization from hot CH$_3$CN without success. Silica gel chromatography with MeOH/DCM (10%–20%) gave 1.05 g (60% yield) of Example 69: TLC (DCM/MeOH, 4/1): $R_f$=0.43; $^1$H NMR (DMSO-$d_6$, 300 MHz) δ10.98 (br s, 1H), 7.91–7.85 (m, 4H), 7.55–7.45 (m, 6H), 7.11 (d, 2H, J=8.4), 6.92 (d, 2H, J=8.4), 6.15 (s, 1H), 5.07 (s, 2H), 4.13–4.06 (m, 1H), 3.16–3.09 (m, 1H), 2.95–2.85 (m, 4H), 1.21 (t, 3H, J=7.5); low resolution MS (ES$^+$)m/e 580.95 (MH$^+$).

Example 70

(2S)-3-{4-[(5-ethyl-2-phenyl-1,3-thiazol -4-yl)methoxy]phenyl}-2-({(Z)-1-methyl-3-oxo-3-[4-(trIfluoromethyl)phenyl]-1-propenyl}amino)propanoic acid The title compound was prepared (as described above for the preparation of Example 2) from 1.35 g (2.72 mmol) of Intermediate 62, 630 mg (2.72 mmol) of Intermediate 24, and 0.8 mL triethylamine in MeOH (20 mL) and trimethylorthoformate (5 mL) to yield 1.04 g (65% yield) of Example 70 after silica gel chromatography (5%–15% MeOH in DCM): TLC (DCM/MeOH, 4/1): $R_f$=0.45; $^1$H NMR (DMSO-$d_6$, 300 MHz) δ11.57 (d, 1H, J=8.7), 7.96 (d, 2H, J=8.4), 7.85 (m, 2H), 7.71 (d, 2H, J=8.4), 7.44 (m, 3H), 6.92 (d, 2H, J=8.4), 5.6 (s, 1H), 5.05 (s, 2H), 4.21–4.27 (m, 1H), 3.27–3.22 (m, 1H), 2.89–2.81 (m, 4H), 1.72 (s, 3H), 1.19 (t, 3H, J=7.5); low resolution MS (ES$^+$)m/e 594.96 (MH$^+$).

Example 71

(2S)-3-{4-[(5-ethyl-2-phenyl-1,3-oxazol-4-yl)methoxy]phenyl}-2-{[(Z)-3-oxo-3-phenyl-1-trifluoromethyl)-1-propenyl]amino}propanoic acid The title compound was prepared (as described above for the preparation of Example 58) from 100 mg (0.27 mmol) of Intermediate 61, 91 mg (0.41 mmol) of Intermediate 44, and 0.14 mL diisopropylethylamine in 2 mL MeOH. Attempted recrystallization from hot CH$_3$CN without success. Silica gel chromatography with MeOH/DCM (10%–20%) gave 91 mg (59% yield) of Example 71: TLC (DCM/MeOH, 4/1): $R_f$=0.57; $^1$H NMR (DMSO-$d_6$, 300 MHz) δ10.96 (br s, 1H), 7.94–7.89 (m, 4H), 7.58–7.44 (m, 6H), 7.12 (d, 2H, J=8.4), 6.89 (d, 2H, J=8.1), 6.16 (s, 1H), 4.93 (s, 2H), 4.20–4.11 (m, 1H), 3.16–3.11 (m, 1H), 2.96–2.88 (m,1H), 2.77 (q, 2H, J=7.5), 1.17 (t, 3H, J=7.5); low resolution MS (ES$^+$)m/e 564.88 (MH$^+$).

Example 72

(2S)-3-(4-{[5-ethyl-2-(4-fluorophenyl)-1,3-oxazol-4-yl]methoxy}phenyl)-2-{[(Z)-3-oxo-3-phenyl-1-(trifluoromethyl)-1-propenyl]amino}propanoic acid The title compound was prepared (as described above for the preparation of Example 58) from 700 mg (1.82 mmol) of Intermediate 63, 610 mg (2.73 mmol) of Intermediate 44, and 0.95 mL diisopropylethylamine in 12 mL MeOH. Silica gel chromatography with MeOH/DCM (10%–20%) gave 580 mg (55% yield) of Example 72: TLC (DCM/MeOH, 4/1): $R_f$=0.50; $^1$H NMR (DMSO-$d_6$, 300 MHz) δ10.95 (br s, 1H), 7.99–7.89 (m, 4H), 7.58–7.53 (m, 3H), 7.34 (t, 2H, J=8.7), 7.12 (d, 2H, J=8.1), 6.89 (d, 2H, J=8.7), 6.16 (s, 1H), 4.92 (s, 2H), 4.21–4.11 (m, 1H), 3.16–3.11 (m, 2H), 2.96–2.91 (m, 1H), 2.79 (q, 2H, J=7.5), 1.17 (t, 3H, J=7.5); low resolution MS (ES$^+$)m/e 582.92 (MH$^+$).

Example 73

(2S)-2-({(Z)-1-ethyl-3-oxo-3-[4-(trifluoromethyl) phenyl]-1-propenyl}amino)-3-{4-[(5-ethyl-2-phenyl-1,3-oxazol-4-yl)methoxy]phenyl}propanoic acid The title compound was prepared (as described above for the preparation of Example 2) from 100 mg (0.27 mmol) of Intermediate 61, 67 mg (0.27 mmol) of Intermediate 25, and 0.08 mL triethylamine in MeOH (2.0 mL) and trimethylorthoformate (0.5 mL) to yield 54 mg (51% yield) of Example 73 after silica gel chromatography (5%–15% MeOH in DCM): TLC (DCM/MeOH, 4/1): $R_f$=0.54; $^1$H NMR (DMSO-$d_6$, 300 MHz) δ11.63 (d, 1H, J=9.3), 7.98–7.90 (m, 4H), 7.73 (d, 2H, J=8.1), 7.50–7.48 (m, 3H), 7.16 (d, 2H, J=8.7), 6.90 (d, 2H, J=8.7), 5.6 (s, 1H), 4.93 (s, 2H), 4.24–4.18 (m, 1H), 3.24–3.19 (m, 1H), 2.84–2.72 (m, 4H), 2.08–1.98 (m, 2H), 1.16 (t, 3H, J=7.8), 0.91 (t, 3H, J=7.5); low resolution MS (ES$^+$)m/e 593.10 (MH$^+$).

Example 74

(2S)-3-(4-{[5-ethyl-2-(4-fluorophenyl)-1,3-oxazol-4-yl]methoxy}phenyl)-2-({(Z)-1-ethyl-3-oxo-3-[4-(trifluoromethyl)phenyl]-1-propenyl}amino) propanoic acid The title compound was prepared (as described above for the preparation of Example 2) from 160 mg (0.42 mmol) of Intermediate 63, 102 mg (0.42 mmol) of Intermediate 25, and 0.12 mL triethylamine in MeOH (3.0 mL) and trimethylorthoformate (0.75 mL) to yield 117 mg (46% yield) of Example 74 after silica gel chromatography (5%–15% MeOH in DCM): TLC (DCM/MeOH, 4/1): $R_f$=0.57; $^1$H NMR (DMSO-$d_6$, 300 MHz) δ11.63 (d, 1H, J=9.6), 7.99–7.93 (m, 4H), 7.72 (d, 2H, J=8.1), 7.32 (t, 2H, J=8.7), 7.16 (d, 2H, J=8.7), 6.90 (d, 2H, J=8.1), 5.6 (s, 1H), 4.91 (s, 2H), 4.26–4.20 (m, 1H), 3.24–3.19 (m, 1H), 2.84–2.72 (m, 4H), 2.07–2.00 (m, 2H), 1.15 (t, 3H, J=7.5), 0.91 (t, 3H, J=7.5); low resolution MS (ES$^+$)m/e 611.10 (MH$^+$).

Example 75

(2S)-3-{4-[(5-ethyl-2-phenyl-1,3-oxazol-4-yl) methoxy]phenyl}-2-({(Z)-1-methyl-3-oxo-3-[4-(trifluoromethyl)phenyl]-1-propenyl}amino) propanoic acid The title compound was prepared (as described above for the preparation of Example 2) from 98 mg (0.27 mmol) of Intermediate 61, 62 mg (0.27 mmol) of Intermediate 24, and 0.08 mL triethylamine in MeOH (2.0 mL) and trimethylorthoformate (0.5 mL) to yield 95 mg (61% yield) of Example 75 after silica gel chromatography (5%–15% MeOH in DCM): TLC (DCM/MeOH, 4/1): $R_f$=0.59; $^1$H NMR (DMSO-$d_6$, 300 MHz) δ11.55 (d, 1H, J=9.0), 7.98–7.90 (m, 4H), 7.73 (d, 2H, J=8.4), 7.51–7.48 (m, 3H), 7.17 (d, 2H, J=8.4), 6.91 (d, 2H, J=8.4), 5.61 (s, 1H), 4.93 (s, 2H), 4.24–4.18 (m, 1H), 3.23–3.16 (m, 1H), 2.86–2.73 (m, 4H), 1.72 (s, 3H), 1.17 (t, 3H, J=7.5); low resolution MS (ES$^+$)m/e 579.05 (MH$^+$).

Example 76

(2S)-3-(4-{[5-ethyl-2-(4-fluorophenyl)-1,3-oxazol-4-yl]methoxy}phenyl)-2-({(Z)-1-methyl-3-oxo-3-[4-(trifluoromethyl)phenyl]-1-propenyl}amino) propanoic acid The title compound was prepared (as described above for the preparation of Example 2) from 176 mg (0.46 mmol) of Intermediate 63, 105 mg (0.46 mmol) of Intermediate 24, and 0.14 mL triethylamine in MeOH (3.0 mL) and trimethylorthoformate (0.75 mL) to yield 152 mg (56% yield) of Example 76 after silica gel chromatography (5%–15% MeOH in DCM): TLC (DCM/MeOH, 4/1): $R_f$=0.55; $^1$H NMR (DMSO-$d_6$, 300 MHz) δ11.55 (d, 1H, J=9.0), 7.99–7.94 (m, 4H), 7.73 (d, 2H, J=8.4), 7.33 (t, 2H, J=8.7), 7.16 (d, 2H, J=8.4), 6.90 (d, 2H, J=8.7), 5.61 (s, 1H), 4.93 (s, 2H), 4.23–4.18 (m, 1H), 3.22–3.18 (m, $_1$H), 2.85–2.73 (m, 4H), 1.72 (s, 3H), 1.17 (t, 3H, J=7.5); low resolution MS (ES$^+$)m/e 597.09 (MH$^+$).

Example 77

(2S)-2-({(Z)-1-ethyl-3-oxo-3-[4-(trifluoromethyl) phenyl]-1-propenyl}amino)-3-{4-[(5-ethyl-2-phenyl-1,3-thiazol-4-yl)methoxy]phenyl}propanoic acid The title compound was prepared (as described above for the preparation of Example 2) from 1.44 g (2.90 mmol) of Intermediate 62, 710 mg (2.90 mmol) of Intermediate 25, and 0.85 mL triethylamine in MeOH (20 mL) and trimethylorthoformate (5 mL) to yield 985 mg (56% yield) of Example 77 after silica gel chromatography (5%–15% MeOH in DCM): TLC (DCM/MeOH, 4/1): $R_f$=0.45; $^1$H NMR (DMSO-$d_6$, 300 MHz) δ11.65 (d, 1H, J=9.3), 7.97 (d, 2H, J=8.1), 7.85 (m, 2H), 7.71 (d, 2H, J=8.1), 7.44 (m, 3H), 7.44 (d, 2H, J=8.1), 7.16 (d, 2H, J=8.1), 5.61 (s, 1H), 5.05 (s, 2H), 4.26–4.19 (m, 1H), 3.26–3.21 (m, 1H), 2.89–2.77 (m, 4H), 2.07–2.0 (m, 2H), 1.19 (t, 3H, J=7.5), 0.91 (t, 3H, J=7.5); low resolution MS (ES$^+$)m/e 609.07 (MH$^+$).

Example 78

(2S)-3-(4-{2-[5-ethyl-2-(4-fluorophenyl)-1,3-oxazol-4-yl]ethoxy}phenyl)-2-({(Z)-1-ethyl-3-oxo-3-[4-(trifluoromethyl)phenyl]-1-propenyl}amino) propanoic acid The title compound was prepared (as described above for the preparation of Example 2) from 150 mg (0.29 mmol) of Intermediate 58 (TFA Salt), 108 mg (0.3 mmol) of Intermediate 25, and 0.1 mL triethylamine in MeOH and trimethylorthoformate to yield 70 mg (38% yield) of Example 78: TLC (DCM/MeOH, 90/10): $R_f$=0.26; $^1$H NMR (DMSO-$d_6$, 300 MHz) δ11.62 (d, 1H, J=9.3), 7.99–7.93 (m, 4H), 7.74 (d, 2H, J=8.4), 7.32 (t, 2H, J=8.9), 7.13 (d, 2H, J=8.4), 6.80 (d, 2H, J=8.5), 5.61 (s, 1H), 4.14 (m, 3H), 3.4–3.1 (m, 2H, obscured by water peak), 2.88 (t, 2H, J=6.4), 2.70 (q, 2H, J=7.4), 2.02 (m, 2H), 1.19 (t, 3H, J=7.5), 0.94 (t, 3H, J=7.5); low resolution MS (ES$^+$)m/e 625.2 (MH$^+$).

Example 79

(2S)-3-(4-{2-[5-ethyl-2-(4-fluorophenyl)-1,3-thiazol-4-yl]ethoxy}phenyl)-2-({(Z)-1-ethyl-3-oxo-3-[4-(trifluoromethyl)phenyl]-1-propenyl}amino) propanoic acid The title compound was prepared (as described above for the preparation of Example 2) from 150 mg (0.28 mmol) of Intermediate 56 (TFA Salt), 108 mg (0.3 mmol) of Intermediate 25, and 0.1 mL triethylamine in MeOH and trimethylorthoformate to yield 60 mg (33% yield) of Example 79: TLC (DCM/MeOH, 90/10): R$_f$=0.26; $^1$H NMR (DMSO-d$_6$, 300 MHz) δ11.63 (d, 1H, J=9.4), 7.98 (d, 2H, J=8.0), 7.9–7.85 (m, 2H), 7.74 (d, 2H, J=8.3), 7.27 (t, 2H, J=8.7), 7.13 (d, 2H, J=8.4), 6.80 (d, 2H, J=8.3), 5.62 (s, 1H), 4.25 (m, 3H), 3.4–3.2 (m, 2H, obscured by water peak), 3.07 (t, 2H, J=6.3), 2.85–2.77 (m, 2H), 2.06–1.99 (m, 2H), 1.21 (t, 3H, J=7.4), 0.93 (t, 3H, J=7.4); low resolution MS (ES$^+$)m/e 641.12 (MH$^+$).

Example 80

(2S)-2-({(Z)-1-ethyl-3-oxo-3-[4-(trifluoromethyl) phenyl]-1-propenyl}amino)-3-{4-[2-(5-ethyl-2-phenyl-1,3-thiazol-4-yl)ethoxy]phenyl}propanoic acid The title compound was prepared (as described above for the preparation of Example 2) from 150 mg (0.29 mmol) of Intermediate 57 (TFA Salt), 108 mg (0.3 mmol) of Intermediate 25, and 0.1 mL triethylamine in MeOH and trimethylorthoformate to yield 40 mg (22% yield) of Example 80: TLC (DCM/MeOH, 90/10): R$_f$=0.28; $^1$H NMR (DMSO-d$_6$, 300 MHz) δ11.62 (d, 1H, J=9.4), 7.98 (d, 2H, J=8.2), 7.85 (m, 2H), 7.74 (d, 2H, J=8.3), 7.48–7.42 (m, 3H), 7.13 (d, 2H, J=8.4), 6.80 (d, 2H, J=8.3), 5.63 (s, 1H), 4.23 (t, 2H, J=6.5), 4.2 (m, 1H), 3.2–3.05 (m, 3H), 2.89–2.75 (m, 3H), 2.07–2.03 (m, 2H), 1.23 (t, 3H, J=7.5), 0.94 (t, 3H, J=7.5); low resolution MS (ES$^+$)m/e 622.91 (MH$^+$).

The following Intermediates A–G were prepared to make radioligand for the binding assay described below.

Intermediate A: 2-(4-(2-(Phenylmethyloxycarbonylamino)ethyl)phenoxy)-2-methylbutanoic acid A solution of 4-(2-(phenylmethyloxycarbonylamino) ethyl)phenol (5.74 g; 21.16 mmole) in 2-butanone (17 mL) and chloroform (6 g) was added dropwise to a mixture of sodium hydroxide (9.0 g; 225 mmole) and 2-butanone. (67 mL) whilst keeping the reaction temperature below 30° C. The mixture was allowed to stir at 30° C. for 4 h. Ether (100 mL) was added and the resultant solid was collected by filtration and washed with ether (100 mL). The solid was dissolved in water (70 mL) and any residual ether removed by evaporation. 1N Hydrochloric acid was added to adjust the pH to 1, and the resulting oil was extracted with dichloroethane (3×50 mL). The combined extracts were dried (Na$_2$SO$_4$) and evaporated to afford a yellow oil (3.82 g; 49%). $^1$H-NMR (CDCl$_3$) δ7.26 (s, 5H), 7.09 (d, 2H, J=7.9 Hz), 6.88 (d, 2H, J=8.4 Hz), 5.09 (s, 2H), 4.75 (br s, 1H), 3.42–3.44 (m, 2H), 2.75 (t, 2H, J=6.7 Hz), 1.92–2.00 (m, 2H), 1.47 (s, 3H), 1.04 (t, 3H, J=2.6 Hz). Mass spectrometry ES$^-$, m/e (M+H)$^+$=372.

Intermediate B: Methyl 2-(4-(2-(phenylmethyloxycarbonylamino)ethyl)phenoxy)-2-methyl butyrate A solution of Intermediate A (2.0 g; 5.38 mmole) in dimethylformamide (12 mL) was treated with potassium carbonate (2.23 g; 16.14 mmole) and methyl iodide (1.54 g; 10.76 mmole) and the resulting mixture stirred at 23° C. for 2 h. The mixture was filtered and the solid collected was washed with ethyl acetate (70 mL). The filtrate was washed with brine (4×50 mL), dried (Na$_2$SO$_4$) and evaporated. The residue was purified by chromatography on silica gel using hexane then 33% ethyl acetate-hexane as eluent to afford a colorless oil (1.27 g; 61%). $^1$H-NMR (DMSO-d$_6$) δ7.31 (m, 5H), 7.06 (d, 2H, J=8.4 Hz), 6.68 (d, 2H, J=8.4 Hz), 4.98 (s, 2H), 3.67 (s, 3H), 3.15 (m, 2H), 2.62 (t, 2H, J=7.1 Hz), 1.86 (m, 2H), 1.38 (s, 3H), 0.86 (t, 3H, J=7.3 Hz). Mass spectrometry ES$^+$, m/e (M+Na)$^+$=408.

Intermediate C: Methyl 2-4-(2-aminoethyl) phenoxy)-2-methyl butyrate acetate salt A solution of Intermediate B (1.27 g; 3.29 mmole) in methanol (50 mL) and acetic acid (0.4 g) was treated with 10% palladium on carbon and shaken in a hydrogen atmosphere (50 psi) for 2 h. The catalyst was filtered through celite and the solvent was evaporated to afford a yellow oil in quantitative yield (1.04 g). $^1$H-NMR (CDCl$_3$): δ7.06 (d, 2H, J=8.4 Hz), 6.77 (d, 2H, J=8.4 Hz), 6.70 (br s, 2H), 3.76 (s, 3H), 3.02 (br s, 2H), 2.82 (m, 2H), 1.99 (s, 3H), 1.92 (m, 2H), 1.48 (s, 3H), 0.96 (t, 3H, J=7.4 Hz). Mass spectrometry ES$^+$, m/e (M+H)$^+$=252.

Intermediate D: Methyl 2-(4-(2-(2,4-dinitrophenylsulfonylamino)ethyl)phenoxy)-2-methyl butyrate A solution of Intermediate C (2 g; 6.42 mmole) in CH$_2$Cl$_2$ (40 mL) was treated with saturated sodium bicarbonate solution and the organic layer was separated. The aqueous layer was extracted with CH$_2$Cl$_2$ (5×50 mL) and the combined organic layers were dried (Na$_2$SO$_4$) and evaporated to afford the free base as a yellow oil (1.61 g; 100%). This was dissolved in CH$_2$Cl$_2$ (40 mL) and treated with pyridine (0.45 g; 5.61 mmole) and 2,4-dinitrophenylsulfonyl chloride (1.5 g; 5.61 mmole), and the mixture was allowed to stir at 23° C. for 3 h. Water (60 mL) was added and the organic layer separated, washed with water (3×40 mL) and saturated sodium bicarbonate (40 mL). The organic layer was dried (Na$_2$SO$_4$) and evaporated and the residue purified by chromatography using 15–20% EtOAc-Hexane as eluent to afford a light yellow solid (1.38 g; 51%). $^1$H-NMR (CDCl$_3$): δ8.63 (d,1H, J=2.3 Hz), 8.49 (dd, 1H, J=8.4 Hz, J'=2.3 Hz), 8.07 (d, 1H, J=8.4 Hz), 6.89 (d, 2H, J=8.4 Hz), 6.54 (d, 2H, J=8.4 Hz), 5.34 (t, 1H, J=5.3 Hz), 3.78 (s, 3H), 3.48 (q, 2H, J=8.3 Hz), 2.75 (t, 2H, J=6.6 Hz), 1.92 (m, 2H), 1.42 (s, 3H), 0.93 (t, 3H, J=7.5 Hz).

Intermediate E: Methyl 2-(4-(2-((2,4-dinitrophenylsulfonyl)(hept-2-en-1-yl))amino)ethyl) phenoxy)-2-methyl butyrate A solution of Intermediate D (315 mg; 0.654 mmole) in THF (15 mL) was treated with triphenylphosphine (343 mg; 1.308 mmole), hept-2-en-1-ol (150 mg; 1.308 mmole) and diethylazodicarboxylate (228 mg; 1.308 mmole) and the mixture allowed to stir at 23° C. for 1 h. The solvent was evaporated and the residue purified by chromatography using 10–15% EtOAc-Hexane as eluent to afford a semi-solid (400 mg; >100%). TLC and NMR shows that the desired compound is present along with 1,2-(diethoxycarbonyl)hydrazine.

Intermediate F: Methyl 2(4-(2-(hept-2-en-1-ylamino)ethyl)phenoxy)-2-methyl butanoate A solution of Intermediate E (400 mg; 0.654 mmole) in CH$_2$Cl$_2$ (5 mL) was treated with triethylamine (132 mg; 1.308 mmole) and mercaptoacetic acid (78 mg; 0.85 mmole) and the mixture was allowed to stir at 23° C. for 1 h. The mixture was diluted with EtOAc (30 mL) and washed with water (3×20 mL) and aqueous sodium bicarbonate (30 mL). The organic layer was dried (Na$_2$SO$_4$), evaporated and the residue purified by chromatography using 10% EtOAc- Hexane then 50% EtOAc-Hexane then MeOH as eluent to afford an oil (177 mg; 78% from intermediate 24). $^1$H-NMR (CDCl$_3$): δ7.06 (d, 2H, J=7.5 Hz), 6.75 (d, 2H, J=7.5 Hz), 5.59 (m, 2H), 3.76 (s, 3H), 3.30 (d, 2H, J=6.3 Hz), 2.87 (m, 4H), 1.47 (s, 3H, 1.28 (m, 5H), 0.96 (t, 3H, J=7.6 Hz), 0.86 (t, 3H, J=6.9 Hz).

Intermediate G: Methyl 2-(4-(2-(1-hept-2-enyl-3-(2, 4-difluorophenyl)ureido)ethyl)phenoxy)-2-methylbutyrate A solution of Intermediate F (157 mg; 0.452 mmole) in methylene chloride (5 mL) was treated with 2,4-difluorophenylisocyanate (140 mg; 0.904 mmole) and the mixture allowed to stand at 23° C. for 18 h. The solvent was evaporated and the residue purified by chromatography on silica gel using 10% then 15% ethyl acetate-hexane as eluent to afford a yellow semi-solid (212 mg; 93%). Contaminated with bis-(2,4-difluorophenyl)urea which co-elutes on column. $^1$H-NMR (CDCl$_3$): δ8.85 (br s, 1H), 8.02 (m, 1H), 7.09 (d, 2H, J=8.4 Hz), 6.77–6.90 (m, 4H), 5.70 (m, 1H), 5.36 (m, 1H), 3.76 (s, 3H), 3.54 (t, 2H, J=7.3 Hz), 2.84 (t, 2H, J=7.1 Hz), 1.55 (br s, 1H), 1.46 (s, 3H), 1.25–1.35 (m, 5H), 0.96 (t, 3H, J=7.3 Hz), 0.88 (t, 3H, J=7.4 Hz). Mass spectrometry CI/AP$^+$, m/e (M+H)$^+$=503.

2-(4-(2-(1-Hept-2-enyl-3-(2,4-difluorophenyl) ureido)ethyl)phenoxy)-2-methylbutanoic acid (Radioligand Precursor)

A solution of Intermediate G (370 mg; 0.736 mmole) in methanol (15 mL) was treated with 1N NaOH (7.5 mL) and the mixture heated under reflux for 2 h. The mixture was acidified with 1N HCl and extracted with ethyl acetate (3×25 mL). The combined organic layers were washed with brine, dried (Na$_2$SO$_4$) and evaporated. The residue was purified by chromatography on silica gel using 20% ethyl acetate-hexane then ethyl acetate as eluent to afford a tan oil (280 mg; 78%). $^1$H-NMR (CDCl$_3$) δ7.95–8.09 (m,1H), 7.14 (d, 2H, J=7.1 Hz), 6.90 (d, 2H, J=7.4 Hz), 6.81 (d, 2H, J=5.2 Hz), 5.66 (m, 1H), 5.37 (m,1H), 3.56 (t, 2H, J=7.4 Hz), 2.87 (t, 2H, J=7.4 Hz), 2.00 (m, 4H), 1.44 (s, 3H), 1.27 (m, 6H), 1.03 (t, 3H, J=7.3 Hz), 0.88 (t, 3H, J=7.3 Hz). Mass spectrometry ES$^-$, m/e (M+H)$^+$=489.

Radioligand: 2-(4-(2-(2,3-Ditritio-1-heptyl-3-(2,4-difluorophenyl)ureido)ethyl)phenoxy)-2-methylbutanoic acid A solution of radioligand precursor prepared above (10 mg) in anhydrous DMF (3.5 mL) was transferred to a reaction vessel containing 10% Pd/C (9.8 mg). The reaction vessel was evacuated and degassed via one freeze-thaw-evacuation cycle and then exposed to tritium gas (10.1 Ci). After 4 h, the mixture was filtered through celite, evaporated and the residue dissolved in acetonitrile. A portion of this solution (0.8 mL, 26.6 mCi) was purified by HPLC (Dynamax C8, 25 min gradient from 4:1 acetonitrile:0.1% TFA to 9:1 acetonitrile: 0.1% TFA, 235 nm). Fractions containg pure material were combined and evaporated under nitrogen. The residue was redissolved in acetonitrile to provide a solution of the title compound (82.0 Ci/mmol, radiochemical purity, 99%).

2-(4-(2-(1-Heptyl-3-(2,4-difluorophenyl)ureido) ethyl)phenoxy)-2-methylbutanoic acid The unlabelled ("cold") version of the above radioligand was prepared as a control. A solution of Intermediate G (10 mg) in anhydrous DMF (3.5 mL) was transferred to a reaction vessel containing 10% Pd/C (9.8 mg). The reaction vessel was evacuated and degassed via one freeze-thaw-evacuation cycle and then exposed to hydrogen gas. After 4 h, the mixture was filtered through celite and evaporated. The residue was purified by chromatography using 2% MeOH/CH$_2$Cl$_2$ as eluent to afford a gum (7 mg).

The radioligand prepared above was used in the PPARα binding assay described below (in addition to $^3$H-BRL 49653 for the PPARγ binding assay) to show that active compounds in the transfection assays were also ligands for PPARα and PPARγ.

Binding Assay

Compounds were tested for their ability to bind to hPPARγ or hPPARα using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand ($^3$H-BRL 49653 for PPARγ and 2-(4-(2-(2,3-Ditritio-1-heptyl-3-(2,4-difluorophenyl)ureido)ethyl)phenoxy)-2-methylbutanoic acid for hPPARα) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent K$_I$ values were estimated from nonlinear least squares fit of the data assuming simple competitive binding. The details of this assay have been reported elsewhere (see, Blanchard, S. G. et. al. *Development of a Scintillation Proximity Assay for Peroxisome Proliferator-Activated Receptor gamma Ligand Binding Domain. Anal. Biochem.* 1998, 257, 112–119).

Preferably, the compounds of this invention bind to both hPPARγ and hPPARα. All of the above Examples 1–80 did bind to both hPPARγ and hPPARα. Apparent pK$_i$ values were >6.3 for all Examples 1–80 in both the PPARγ and PPARα binding assays described above (pK$_i$=-log of the concentration of test compound required to achieve an apparent K$_i$ value according to the equation K$_i$=IC$_{50}$/1+[L]/K$_d$, where IC$_{50}$=the concentration of test compound required to inhibit 50% of the specific binding of the radioligand, [L] is the concentration of the radioligand used, and K$_d$ is the dissociation constant for the radioligand at the receptor).

Transfection Assay

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Simth-Oliver, T. A.; Wilkison, W. O.; Willson, T. M.; Kliewer, S. A., *An antidiabetic thiazolidinedione is a high affinity ligand for peroxisome proliferator-activated receptor γ (PPARγ), J. Biol. Chem.*, 1995, 270, 12953-6. The ligand binding domains for murine and human PPARα, and PPARγ, were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the β-galactosidase activity as an internal standard (see, for example, Kliewer, S. A., et. al. *Cell* 83, 813–819 (1995)). Rosiglitazone (BRL 49653) was used as a positive control in the hPPARγ assay. The positive control in the hPPARα assay was 2-[4-(2-(3-(4-fluorophenyl)-1-heptylureido)ethyl)-phenoxy]-2-methylpropionic acid, which can be prepared as described in Brown, Peter J., et. al. *Synthesis* Issue 7, 778–782 (1997), or patent publication WO 9736579.

All of the above Examples showed at least 50% activation of hPPARα and hPPARγ at concentrations of $10^{-7}$ M or less.

In vivo evaluation

Male Zucker Diabetic Fatty rats were lightly anesthetized with isofluorane gas and bleed by tail vein to obtain post-prandial baseline concentrations for plasma glucose, serum lipids and insulin. Animals were baseline matched by plasma glucose and randomized into vehicle or treatment groups with compound administration by oral gavage, b.i.d., beginning at 8.5 weeks of age. Selected compounds were administered as a suspension in 0.5% methylcellulose for 7 consecutive days. Changes in body weight and food consumption were monitored from representative animals from each group, over a 48 hr period. After 7 days of treatment animals were anesthetized, blood samples obtained and analyzed for plasma glucose and lactate, serum triglyceride, total and HDL cholesterol, non-esterified free fatty acids and insulin concentration. Livers were weighed and corrected for body weight. Values in Table 1 for % Glucose reduction represent a summary of the percent reduction from vehicle control animals at day 7 relative to normalization defined in this model as plasma glucose levels of 140 mg/dL.

TABLE 1

Biological activity

| Example | % Glucose Reduction |
| --- | --- |
| 1 | 39 |
| 7 | 34 |
| 12 | 61 |
| 16 | 59 |
| 20 | 50 |
| 21 | 82 |
| 22 | 49 |
| 23 | 86 |
| 24 | 45 |
| 40 | 79 |
| 48 | 81 |

What is claimed is:

1. A compound of formula (I), or a tautomeric form, pharmaceutically acceptable salt, or solvate thereof,

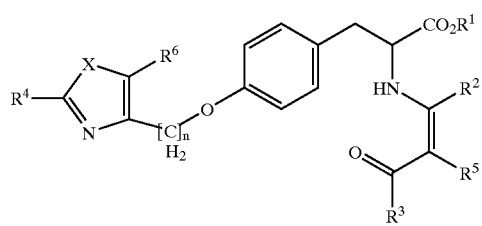

(I)

wherein;

$R^1$ is hydrogen or $C_{1-3}$alkyl;

$R^2$ is hydrogen, or $C_{1-8}$alkyl optionally substituted by one or more halogens;

$R^3$ is $C_{1-6}$alkyl, $C_{4-7}$cycloalkyl or cycloalkenyl, —$OC_{1-6}$alkyl, —NR'R' (where each R' is independently hydrogen or $C_{1-3}$alkyl), a 5 or 6 membered heterocyclic group containing at least one oxygen, nitrogen, or sulfur ring atom (optionally substituted by one or more halogen, $C_{1-6}$alkyl optionally substituted by one or more halogens, —$OC_{1-6}$alkyl optionally substituted by one or more halogens, —CN, or —$NO_2$), or phenyl (optionally substituted by one or more halogen, $C_{1-6}$alkyl optionally substituted by one or more halogens, —$OC_{1-6}$alkyl optionally substituted by one or more halogens, —CN, or —$NO_2$);

$R^4$ is a 5 or 6 membered heterocyclic group containing at least one oxygen, nitrogen, or sulfur ring atom (optionally substituted by one or more halogen, $C_{1-6}$alkyl optionally substituted by one or more halogens, —$OC_{1-6}$alkyl optionally substituted by one or more halogens, —CN, or —$NO_2$), or phenyl (optionally substituted by one or more halogen, $C_{1-6}$alkyl optionally substituted by one or more halogens, —$OC_{1-6}$alkyl optionally substituted by one or more halogens, —NR'R', —CN, or —$NO_2$);

$R^5$ is hydrogen, halogen, or $C_{1-3}$alkyl optionally substituted by one or more halogens;

$R^6$ is hydrogen or $C_{1-3}$alkyl;

X is O or S; and n is 1, 2, or 3.

2. A compound of claim 1 wherein $R^1$ is hydrogen or methyl.

3. A compound of claim 1 wherein $R^2$ is $C_{1-8}$alkyl optionally substituted by one or more halogens.

4. A compound of claim 1 wherein $R^3$ is, pyridine, pyrazine, thiophene, furan, thiazole, or phenyl (any of which may be optionally substituted by one or more halogen, $C_{1-6}$alkyl optionally substituted by one or more halogens, —$OC_{1-6}$alkyl optionally substituted by one or more halogens, —CN, or —$NO_2$) or $C_{4-7}$cycloalkyl.

5. A compound of claim 4 wherein $R^3$ is phenyl (optionally substituted by one or more halogen, $C_{1-6}$alkyl optionally substituted by one or more halogens, —$OC_{1-6}$ alkyl optionally substituted by one or more halogens, —CN, or —$NO_2$).

6. A compound of claim 1 wherein $R^4$ is phenyl (optionally substituted by one or more halogen, $C_{1-6}$alkyl optionally substituted by one or more halogens, or —$OC_{1-6}$alkyl optionally substituted by one or more halogens).

7. A compound of claim 1 wherein $R^5$ is hydrogen, or $C_{1-3}$alkyl optionally substituted by one or more halogens.

8. A pharmaceutical composition according to claim 7 further comprising a pharmaceutically acceptable diluent or carrier.

9. A compound of claim 1 wherein $R^6$ is methyl or ethyl.

10. A compound of claim 1 selected from the group consisting of:

(2S)-2-{[(Z)-1-methyl-3-oxo-3-phenyl-1-propenyl]amino}-3-{4-[2-(5-methyl-2-phenyl-1,3-oxazol-4-yl)ethoxy]phenyl}propanoic acid;

(2S)-3-(4-{2-[2-(4-fluorophenyl)-5-methyl-1,3-oxazol-4-yl]ethoxy}phenyl)-2-({(Z)-1-methyl-3-oxo-3-[4-(trifluoromethyl)phenyl]-1-propenyl}amino)propanoic acid;

(2S)-3-(4-{2-[2-(4-isopropoxyphenyl)-5-methyl-1,3-oxazol-4-yl]ethoxy}phenyl)-2-({(Z)-1-methyl-3-oxo-3-[4-(trifluoromethyl)phenyl]-1-propenyl}amino)propanoic acid;

(2S)-3-(4-{2-[2-(4-methoxyphenyl)-5-methyl-1,3-oxazol-4-yl]ethoxy}phenyl)-2-({(Z)-1-methyl-3-oxo-3-[4-(trifluoromethyl)phenyl]-1-propenyl}amino)propanoic acid;

(2S)-2-{[(Z)-1-ethyl-3-oxo-3-phenyl-1-propenyl]amino}-3-[4-(2-{5-methyl-2-[4-(trifluoromethyl)phenyl]-1,3-oxazol-4-yl}ethoxy)phenyl]propanoic acid;

(2S)-2-{[(Z)-1-ethyl-3-(4-fluorophenyl)-3-oxo-1-propenyl]amino}-3-(4-{2-[2-(4-methoxyphenyl)-5-methyl-1,3-oxazol-4-yl]ethoxy}phenyl)propanoic acid;

(2S)-2-{[(Z)-1-methyl-3-oxo-3-phenyl-1-propenyl]amino}-3-[4-(2-{5-methyl-2-[4-(trifluoromethyl)phenyl]-1,3-oxazol-4-yl}ethoxy)phenyl]propanoic acid;

(2S)-2-{[(Z)-1-ethyl-3-oxo-3-phenyl-1-propenyl]amino}-3-(4-{2-[2-(4-fluorophenyl)-5-methyl-1,3-oxazol-4-yl]ethoxy}phenyl)propanoic acid;

(2S)-2-{[(Z)-1-ethyl-3-(4-fluorophenyl)-3-oxo-1-propenyl]amino}-3-(4-{2-[2-(4-fluorophenyl)-5-methyl-1,3-oxazol-4-yl]ethoxy}phenyl)propanoic acid;

(2S)-2-({(Z)-1-methyl-3-oxo-3-[4-(trifluoromethyl)phenyl]-1-propenyl}amino)-3-{4-[2-(5-methyl-2-phenyl-1,3-thiazol-4-yl)ethoxy]phenyl}propanoic acid;

(2S)-2-{[(Z)-3-(4-fluorophenyl)-1-methyl-3-oxo-1-propenyl]amino}-3-{4-[2-(5-methyl-2-phenyl-1,3-oxazol-4-yl)ethoxy]phenyl}propanoic acid;

(2S)-2-{[(Z)-1-methyl-3-oxo-3-(2,3,4-trifluorophenyl)-1-propenyl]amino}-3-{4-[2-(5-methyl-2-phenyl-1,3-oxazol-4-yl)ethoxy]phenyl}propanoic acid;

(2S)-2-{[(Z)-1-methyl-3-(4-nitrophenyl)-3-oxo-1-propenyl]amino}-3-{4-[2-(5-methyl-2-phenyl-1,3-oxazol-4-yl)ethoxy]phenyl}propanoic acid;

(2S)-2-({(Z)-1-methyl-3-oxo-3-[4-(trifluoromethyl)phenyl]-1-propenyl}amino)-3-{4-[2-(5-methyl-2-phenyl-1,3-oxazol-4-yl)ethoxy]phenyl}propanoic acid;

(2S)-2-{[(Z)-1-ethyl-3-(4-fluorophenyl)-3-oxo-1-propenyl]amino}-3-(4-{2-[2-(4-isopropoxyphenyl)-5-methyl-1,3-oxazol-4-yl]ethoxy}phenyl)propanoic acid;

(2S)-2-{[(Z)-1-methyl-3-oxo-3-(2,4,5-trifluorophenyl)-1-propenyl]amino}-3-{4-[2-(5-methyl-2-phenyl-1,3-oxazol-4-yl)ethoxy]phenyl}propanoic acid;

(2S)-2-{[(Z)-1-ethyl-3-oxo-3-phenyl-1-propenyl]amino}-3-(4-{2-[2-(4-isopropoxyphenyl)-5-methyl-1,3-oxazol-4-yl]ethoxy}phenyl)propanoic acid;

(2S)-2-({(Z)-1-ethyl-3-oxo-3-[4-(trifluoromethyl)phenyl]-1-propenyl}amino)-3-{4-[2-(5-methyl-2-phenyl-1,3-oxazol-4-yl)ethoxy]phenyl}propanoic acid;

(2S)-2-{[(Z)-1-methyl-3-(4-methylphenyl)-3-oxo-1-propenyl]amino}-3-{4-[2-(5-methyl-2-phenyl-1,3-oxazol-4-yl)ethoxy]phenyl}propanoic acid;

(2S)-2-{[(Z)-1-ethyl-3-oxo-3-phenyl-1-propenyl]amino}-3-{4-[2-(5-methyl-2-phenyl-1,3-oxazol-4-yl)ethoxy]phenyl}propanoic acid;

(2S)-3-(4-{2-[2-(4-fluorophenyl)-5-methyl-1,3-thiazol-4-yl]ethoxy}phenyl)-2-{[(Z)-3-oxo-3-phenyl-1-(trifluoromethyl)-1-propenyl]amino}propanoic acid;

(2S)-2-({(Z)-1-ethyl-3-oxo-3-[4-(trifluoromethyl)phenyl]-1-propenyl}amino)-3-(4-{2-[2-(4-fluorophenyl)-5-methyl-1,3-thiazol-4-yl]ethoxy}phenyl)propanoic acid;

(2S)-2-{[(Z)-1-butyl-3-oxo-3-phenyl-1-propenyl]amino}-3-{4-[2-(5-methyl-2-phenyl-1,3-oxazol-4-yl)ethoxy]phenyl}propanoic acid;

(2S)-2-{[(Z)-3-(4-chlorophenyl)-1-methyl-3-oxo-1-propenyl]amino}-3-{4-[2(5-methyl-2-phenyl-1,3-oxazol-4-yl)ethoxy]phenyl}propanoic acid;

(2S)-2-{[(Z)-1-methyl-3-(3-nitrophenyl)-3-oxo-1-propenyl]amino}-3-{4-[2-(5-methyl-2-phenyl-1,3-oxazol-4-yl)ethoxy]phenyl}propanoic acid;

(2S)-2-({(Z)-3-[2-fluoro-3-(trifluoromethyl)phenyl]-1-methyl-3-oxo-1-propenyl}amino)-3-{4-[2-(5-methyl-2-phenyl-1,3-oxazol-4-yl)ethoxy]phenyl}propanoic acid;

(2S)-2-{[(Z)-3-(4-isopropoxyphenyl)-1-methyl-3-oxo-1-propenyl]amino}-3-{4-[2-(5-methyl-2-phenyl-1,3-oxazol-4-yl)ethoxy]phenyl}propanoic acid;

(2S)-2-{[(Z)-3-(2-chlorophenyl)-1-methyl-3-oxo-1-propenyl]amino}-3-{4-[2-(5-methyl-2-phenyl-1,3-oxazol-4-yl)ethoxy]phenyl}propanoic acid;

(2S)-2-{[(Z)-3-(2-furyl)-1-methyl-3-oxo-1-propenyl]amino}-3-{4-[2-(5-methyl-2-phenyl-1,3-oxazol-4-yl)ethoxy]phenyl}propanoic acid;

(2S)-2-{[(Z)-1-methyl-3-oxo-3-(2-pyrazinyl)-1-propenyl]amino}-3-{4-[2-(5-methyl-2phenyl-1,3-oxazol-4-yl)ethoxy]phenyl}propanoic acid;

(2S)-2-{[(Z)-3-(2,4-difluorophenyl)-1-methyl-3-oxo-1-propenyl]amino}-3-{4-[2-(5-methyl-2-phenyl-1,3-oxazol-4-yl)ethoxy]phenyl}propanoic acid;

(2S)-2-{[(Z)-1-methyl-3-oxo-3-(1,3-thiazol-2-yl)-1-propenyl]amino}-3-{4-[2-(5-methyl-2-phenyl-1,3-oxazol-4-yl)ethoxy]phenyl}propanoic acid;

(2S)-2-{[(Z)-1-methyl-3-oxo-3-(3-thienyl)-1-propenyl]amino}-3-{4-[2-(5-methyl-2-phenyl-1,3-oxazol-4-yl)ethoxy]phenyl}propanoic acid;

(2S)-2-{[(Z)-1-methyl-3oxo-3-(2-pyridinyl)-1-propenyl]amino}-3-{4-[2-(5-methyl-2-phenyl-1,3-oxazol-4-yl)ethoxy]phenyl}propanoic acid;

(2S)-2-{[(Z)-1-ethyl-3-(4-fluorophenyl)-3-oxo-1-propenyl]amino}-3-{4-[2-(5-methyl-2-phenyl-1,3-oxazol-4-yl)ethoxy]phenyl}propanoic acid;

(2S)-2-{[(Z)-1-methyl-3-oxo-3-phenyl-1-propenyl]amino3-{4-[2-(5-methyl-2-phenyl-1,3-thiazol-4-yl)ethoxy]phenyl}propanoic acid;

(2S)-2-{[(Z)-3-(2-fluorophenyl)-1-methyl-3-oxo-1-propenyl]amino}-3-{4-[2-(5-methyl-2-phenyl-1,3-oxazol-4-yl)ethoxy]phenyl}propanoic acid;

(2S)-2-{[(Z)-3-(2,3-difluorophenyl)-1-methyl-3-oxo-1-propenyl]amino}-3-{4-[2-(5-methyl-2-phenyl-1,3-oxazol-4-yl)ethoxy]phenyl}propanoic acid;

(2S)-2-{[(Z)-3-(2-hydroxyphenyl)-1-methyl-3-oxo-1-propenyl]amino}-3-{4-[2-(5-methyl-2-phenyl-1,3-oxazol-4-yl)ethoxy]phenyl}propanoic acid;

(2S)-3-{4-[2-(5-methyl-2-phenyl-1,3-oxazol-4-yl)ethoxy]phenyl}-2-{[(Z)-3oxo-3-phenyl-1-propyl-1-propenyl]amino}propanoic acid;

(2S)-2-{[(Z)-3-(4-methoxyphenyl)-1-methyl-3-oxo-1-propenyl]amino}-3-{4-[2-(5-methyl-2-phenyl-1,3-oxazol-4-yl)ethoxy]phenyl}propanoic acid;

(2S)-3-(4-{2-[2-(4-methoxyphenyl)-5-methyl-1,3-oxazol-4-yl]ethoxy}phenyl)-2-{[(Z)-1-methyl-3-oxo-3-phenyl-1-propenyl]amino}propanoic acid;

(2S)-2-{[(Z)-3-cyclohexyl-1-methyl-3-oxo-1-propenyl]amino}-3-{4-[2-(5-methyl-2-phenyl-1,3-oxazol-4-yl)ethoxy]phenyl}propanoic acid;

(2S)-3-(4-{2-[2-(4-isopropoxyphenyl)-5-methyl-1,3-oxazol-4-yl]ethoxy}phenyl)-2-{[(Z)-1-methyl-3-oxo-3-phenyl-1-propenyl]amino}propanoic acid;

(2S)-2-{[(Z)-1-heptyl-3-oxo-3-phenyl-1-propenyl]amino}-3-{4-[2-(5-methyl-2-phenyl-1,3-oxazol-4-yl)ethoxy]phenyl}propanoic acid;

(2S)-2-{[(Z)-1-methyl-3-(3-methylphenyl)-3-oxo-1-propenyl]amino}-3-{4-[2-(5-methyl-2-phenyl-1,3-oxazol-4-yl)ethoxy]phenyl}propanoic acid;

(2S)-2-{[(Z)-1-ethyl-3-oxo-3-phenyl-1-propenyl]amino}-3-(4-{2-[2-(4-methoxyphenyl)-5-methyl-1,3-oxazol-4-yl]ethoxy}phenyl)propanoic acid;

(2S)-3-{4-[2-(5-methyl-2-phenyl-1,3-oxazol-4-yl)ethoxy]phenyl}-2-{[(Z)-3-oxo-3-phenyl-1-(trifluoromethyl)-1-propenyl]amino}propanoic acid;

(2S)-3-{4-[2-(5-methyl-2-phenyl-1,3-thiazol-4-yl)ethoxy]phenyl}-2-{[(Z)-3-oxo-3-phenyl-1-(trifluoromethyl)-1-propenyl]amino}propanoic acid;

(2S)-2-({(Z)-1-ethyl-3-oxo-3-[4-(trifluoromethyl)phenyl]-1-propenyl}amino)-3-(4-{2-[2-(4-fluorophenyl)-5-methyl-1,3-oxazol-4-yl]ethoxy}phenyl)propanoic acid;

(2S)-2-({(Z)-1-ethyl-3-oxo-3-[4-(trifluoromethyl)phenyl]-1-propenyl}amino)-3-(4-{2-[2-(4-isopropoxyphenyl)-5-methyl-1,3-oxazol-4-yl]ethoxy}phenyl)propanoic acid;

(2S)-2-({(Z)-1-ethyl-3-oxo-3-[4-(trifluoromethyl)phenyl]-1-propenyl}amino)-3-(4-{2-[2-(4-methoxyphenyl)-5-methyl-1,3-oxazol-4-yl]ethoxy}phenyl)propanoic acid;

(2S)-3-(4-{2-[2-(4-fluorophenyl)-5-methyl-1,3-oxazol-4-yl]ethoxy}phenyl)-2-{[(Z)-3-oxo-3-phenyl-1-(trifluoromethyl)-1-propenyl]amino}propanoic acid;

(2S)-2-{([(Z)-1-methyl-3-oxo-3-phenyl-1-propenyl]amino}-3-{4-[(5-methyl-2-phenyl-1,3-oxazol-4-yl)methoxy]phenyl}propanoic acid;

(2S)-3-{4-[2-(5-ethyl-2-phenyl-1,3-oxazol-4-yl)ethoxy]phenyl}-2-{([(Z)-1-methyl-3-oxo-3-phenyl-1-propenyl]amino}propanoic acid;

(2S)-2-{[(Z)-1-methyl-3-oxo-3-phenyl-1-propenyl]amino}-3-{4-[2-(2-phenyl-5-propyl-1,3-oxazol-4-yl)ethoxy]phenyl}propanoic acid;

(2S)-2-{[(Z)-1-methyl-3-oxo-3-phenyl-1-propenyl]amino}-3-{4-[3-(5-methyl-2-phenyl-1,3-oxazol-4-yl)propoxy]phenyl}propanoic acid;

(2S)-3-{4-[2-(5-ethyl-2-phenyl-1,3-oxazol-4-yl)ethoxy]phenyl}-2-{[(Z)-3-oxo-3-phenyl-1-(trifluoromethyl)-1-propenyl]amino}propanoic acid;

(2S)-3-{4-[3-(5-methyl-2-phenyl-1,3-oxazol-4-yl)propoxy]phenyl}-2-{[(Z)-3-oxo-3-phenyl-1-(trifluoromethyl)-1-propenyl]amino}propanoic acid;

(2S)-3-{4-[2-(5-ethyl-2-phenyl-1,3-thiazol-4-yl)ethoxy]phenyl}-2-{[(Z)-3-oxo-3-phenyl-1-(trifluoromethyl)-1-propenyl]amino}propanoic acid;

(2S)-3-(4-{2-[5-ethyl-2-(4-fluorophenyl)-1,3-oxazol-4-yl]ethoxy}phenyl)-2-{[(Z)-3-oxo-3-phenyl-1-(trifluoromethyl)-1-propenyl]amino}propanoic acid;

(2S)-3-(4-{3-[5-ethyl-2-(4-fluorophenyl)-1,3-oxazol-4-yl]propoxy}phenyl)-2-{[(Z)-3-oxo-3-phenyl-1-(trifluoromethyl)-1-propenyl]amino}propanoic acid;

(2S)-3-(4-{2-[5-ethyl-2-(4-fluorophenyl)-1,3-thiazol-4-yl]ethoxy}phenyl)-2-{[(Z)-3-oxo-3-phenyl-1-(trifluoromethyl)-1-propenyl]amino}propanoic acid;

(2S)-3-(4-{3-[5-ethyl-2-(4-fluorophenyl)-1,3-oxazol-4-yl]propoxy}phenyl)-2-({(Z)-1-ethyl-3-oxo-3-[4-(trifluoromethyl)phenyl]-1-propenyl}amino)propanoic acid;

(2S)-2-({(Z)-1-ethyl-3-oxo-3-[4-(trifluoromethyl)phenyl]-1-propenyl}amino)-3-{4[3-(5-ethyl-2-phenyl-1,3-oxazol-4-yl)propoxy]phenyl}propanoic acid;

(2S)-3-(4-{3-[5-ethyl-2-(4-fluorophenyl)-1,3-oxazol-4-yl]propoxy}phenyl)-2-({(Z)-1-methyl-3-oxo-3-[4-(trifluoromethyl)phenyl]-1-propenyl}amino)propanoic acid;

(2S)-3-{4-[3-(5-ethyl-2-phenyl-1,3-oxazol-4-yl)propoxy]phenyl}-2-({(Z)-1-methyl-3-oxo-3-[4-(trifluoromethyl)phenyl]-1-propenyl}amino)propanoic acid;

(2S)-3-{4-[3-(5-ethyl-2-phenyl-1,3-oxazol-4-yl)propoxy]phenyl}-2-{[(Z)-3-oxo-3-phenyl-1-(trifluoromethyl)-1-propenyl]amino}propanoic acid;

(2S)-3-{4-[(5-ethyl-2-phenyl-1,3-thiazol-4-yl)methoxy]phenyl}-2-{[(Z)-3-oxo-3-phenyl-1-(trifluoromethyl)-1-propenyl]amino}propanoic acid;

(2S)-3-{4-[(5-ethyl-2-phenyl-1,3-thiazol-4-yl)methoxy]phenyl}-2-({(Z)-1-methyl-3-oxo-3-[4-(trifluoromethyl)phenyl]-1-propenyl}amino)propanoic acid;

(2S)-3-{4-[(5-ethyl-2-phenyl-1,3-oxazol-4-yl)methoxy]phenyl}-2-{[(Z)-3-oxo-3-phenyl-1-(trifluoromethyl)-1-propenyl]amino}propanoic acid;

(2S)-3-(4-{[(5-ethyl-2-(4-fluorophenyl)-1,3-oxazol-4-yl]methoxy{phenyl)-2-{[(Z)-3-oxo-3-phenyl-1-(trifluoromethyl)-1-propenyl]amino}propanoic acid;

(2S)-2-({(Z)-1-ethyl-3-oxo-3-[4-(trifluoromethyl)phenyl]-1-propenyl}amino)-3-{4-[(5ethyl-2-phenyl-1,3-oxazol-4-yl)methoxy]phenyl}propanoic acid;

(2S)-3-(4-{[5-ethyl-2-(4-fluorophenyl)-1,3-oxazol-4-yl]methoxy}phenyl)2-({(Z)-1-ethyl-3-oxo-3-[4-(trifluoromethyl)phenyl]-1-propenyl}amino)propanoic acid;

(2S)-3-{4-[(5-ethyl-2-phenyl-1,3-oxazol-4-yl)methoxy]phenyl}-2-({(Z)-1-methyl-3-oxo-3-[4-(trifluoromethyl)phenyl]-1-propenyl}amino)propanoic acid;

(2S)-3-(4-{[5-ethyl-2-(4-fluorophenyl)-1,3-oxazol-4-yl]methoxy}phenyl)-2-({(Z)-1-methyl-3-oxo-3-[4-(trifluoromethyl)phenyl]-1-propenyl}amino)propanoic acid;

(2S)-2-({(Z)-1-ethyl-3-oxo-3-[4-(trifluoromethyl)phenyl]-1-propenyl}amino)-3-{4-[(5-ethyl-2-phenyl-1,3-thiazol-4-yl)methoxy]phenyl}propanoic acid;

(2S)-3-(4-{2-[5-ethyl-2-(4-fluorophenyl)-1,3-oxazol-4-yl]ethoxy}phenyl)-2-({(Z)-1-ethyl-3-oxo-3-[4-(trifluoromethyl)phenyl]-1-propenyl}amino)propanoic acid;

(2S)-3-(4-{2-[5-ethyl-2-(4-fluorophenyl)-1,3-thiazol-4-yl]ethoxy}phenyl)-2-({(Z)-1-ethyl-3-oxo-3-[4-(trifluoromethyl)phenyl]-1-propenyl}amino)propanoic acid;

(2S)-2-({(Z)-1-ethyl-3-oxo-3-[4-(trifluoromethyl)phenyl]-1-propenyl}amino)-3-{4-[2-(5-ethyl-2-phenyl-1,3-thiazol-4-yl)ethoxy]phenyl}propanoic acid;

and pharmaceutically acceptable salts and solvates thereof.

11. A compound of claim 1 selected from the group consisting of (2S)-2-{[(Z)-1-methyl-3-oxo-3-phenyl-1-propenyl]amino}-3-{4-[2-(5-methyl-2-phenyl-1,3-oxazol-4-yl)ethoxy]phenyl}propanoic acid;

(2S)-2-{[(Z)-1-methyl-3-oxo-3-phenyl-1-propenyl]amino}-3-[4-(2-{5-methyl-2-[4-(trifluoromethyl)phenyl]-1,3-oxazol-4-yl}ethoxy)phenyl]propanoic acid;

(2S)-2-{[(Z)-1-methyl-3-oxo-3-(2,3,4-trifluorophenyl)-1-propenyl]amino}-3-{4-[2-(5-methyl-2-phenyl-1,3-oxazol-4-yl)ethoxy]phenyl}propanoic acid;

(2S)-2-{[(Z)-1-methyl-3-(4-nitrophenyl)-3-oxo-1-propenyl]amino}-3-{4-[2-(5-methyl-2-phenyl-1,3-oxazol-4-yl)ethoxy]phenyl}propanoic acid;

(2S)-2-({(Z)-1-methyl-3-oxo-3-[4-(trifluoromethyl)phenyl]-1-propenyl}amino)-3-{4-[2-(5-methyl-2-phenyl-1,3-oxazol-4-yl)ethoxy]phenyl}propanoic acid;

(2S)-2-{[(Z)-1-methyl-3-oxo-3-(2,4,5-trifluorophenyl)-1-propenyl]amino}-3-{4-[2-(5-methyl-2-phenyl-1,3-oxazol-4-yl)ethoxy]phenyl}propanoic acid;

(2S)-2-{[(Z)-1-ethyl-3-oxo-3-phenyl-1-propenyl]amino}-3-{4-[2-(5-methyl-2-phenyl-1,3-oxazol-4-yl)ethoxy]phenyl}propanoic acid;

(2S)-3-(4-{2-[2-(4-fluorophenyl)-5-methyl-1,3-thiazol-4-yl]ethoxy}phenyl)-2-{[(Z)-3-oxo-3-phenyl-1-(trifluoromethyl)-1-propenyl]amino}propanoic acid;

(2S)-2-({(Z)-1-ethyl-3-oxo-3-[4-(trifluoromethyl)phenyl]-1-propenyl}amino)-3-(4-{2-[2-(4-fluorophenyl)-5-methyl-1,3-thiazol-4-yl]ethoxy}phenyl)propanoic acid;

(2S)-2-{[(Z)-1-butyl-3-oxo-3-phenyl-1-propenyl]amino}-3-{4-[2-(5-methyl-2-phenyl-1,3-oxazol-4-yl)ethoxy]phenyl}propanoic acid;

(2S)-2-{[(Z)-3-(4-chlorophenyl)-1-methyl-3-oxo-1-propenyl]amino}-3-{4-[2-(5-methyl-2-phenyl-1,3-oxazol-4-yl)ethoxy]phenyl}propanoic acid;

(2S)-3-{4-[2-(5-methyl-2-phenyl-1,3-oxazol-4-yl)ethoxy]phenyl}-2-{[(Z)-3-oxo-3-phenyl-1-propyl-1-propenyl]amino}propanoic acid;

(2S)-3-{4-[2-(5-methyl-2-phenyl-1,3-oxazol-4-yl)ethoxy]phenyl}-2-{[(Z)-3-oxo-3-phenyl-1-(trifluoromethyl)-1-propenyl]amino}propanoic acid;

(2S)-2-({(Z)-1-ethyl-3-oxo-3-[4-(trifluoromethyl)phenyl]-1-propenyl}amino)-3-(4-{2-[2-(4-fluorophenyl)-5-methyl-1,3-oxazol-4-yl]ethoxy}phenyl)propanoic acid;

(2S)-2-({(Z)-1-ethyl-3-oxo-3-[4-(trifluoromethyl)phenyl]-1-propenyl}amino)-3-(4-{2-[2-(4-methoxyphenyl)-5-methyl-1,3-oxazol-4-yl]ethoxy}phenyl)propanoic acid;

(2S)-3-(4-{2-[2-(4-fluorophenyl)-5-methyl-1,3-oxazol-4-yl]ethoxy}phenyl)-2-{[(Z)-3-oxo-3-phenyl-1-(trifluoromethyl)-1-propenyl]amino}propanoic acid;

(2S)-2-{[(Z)-1-methyl-3-oxo-3-phenyl-1-propenyl]amino}-3-{4-[(5-methyl-2-phenyl-1,3-oxazol-4-yl)methoxy]phenyl}propanoic acid;

(2S)-3-{4-[2-(5-ethyl-2-phenyl-1,3-oxazol-4-yl)ethoxy]phenyl}-2-{[(Z)-1-methyl-3-oxo-3-phenyl-1-propenyl]amino}propanoic acid;

(2S)-2-{[(Z)-1-methyl-3-oxo-3-phenyl-1-propenyl]amino}-3-{4-[3-(5-methyl-2-phenyl-1,3-oxazol-4-yl)propoxy]phenyl}propanoic acid;

(2S)-3-{4-[2-(5-ethyl-2-phenyl-1,3-oxazol-4-yl)ethoxy]phenyl}-2-{[(Z)-3-oxo-3-phenyl-1-(trifluoromethyl)-1-propenyl]amino}propanoic acid;

(2S)-3-{4-[2-(5-ethyl-2-phenyl-1,3-thiazol-4-yl)ethoxy]phenyl}-2-{[(Z)-3-oxo-3-phenyl-1-(trifluoromethyl)-1-propenyl]amino}propanoic acid;

(2S)-3-(4-{2-[5-ethyl-2-(4-fluorophenyl)-1,3-oxazol-4-yl]ethoxy}phenyl)-2-{[(Z)-3-oxo-3phenyl-1-(trifluoromethyl)-1-propenyl]amino}propanoic acid;

(2S)-3-(4-{3-[5-ethyl-2-(4-fluorophenyl)-1,3-oxazol-4-yl]propoxy}phenyl)-2{[(Z)-3-oxo-3-phenyl-1-(trifluoromethyl)-1-propenyl]amino}propanoic acid;

(2S)-3-(4-{2-[5-ethyl-2-(4-fluorophenyl)-1,3-thiazol-4-yl]ethoxy}phenyl)-2-{[(Z)-3-oxo-3-phenyl-1-(trifluoromethyl)-1-propenyl]amino}propanoic acid;

(2S)-3-(4-{3-[5-ethyl-2-(4-fluorophenyl)-1,3-oxazol-4-yl]propoxy}phenyl)-2-({(Z)-1-ethyl-3-oxo-3-[4-(trifluoromethyl)phenyl]-1-propenyl}amino)propanoic acid;

(2S)-2-({(Z)-1-ethyl-3-oxo-3-[4-(trifluoromethyl)phenyl]-1-propenyl}amino)-3-{4-[3-(5-ethyl-2-phenyl-1,3-oxazol-4-yl)propoxy]phenyl}propanoic acid;

(2S)-3-(4-{3-[5-ethyl-2-(4-fluorophenyl)-1,3-oxazol-4-yl]propoxy}phenyl)-2-({(Z)-1-methyl-3-oxo-3-[4-(trifluoromethyl)phenyl]-1-propenyl}amino)propanoic acid;

(2S)-3-{4-[3-(5-ethyl-2-phenyl-1,3-oxazol-4-yl)propoxy]phenyl}-2-({(Z)-1-methyl-3-oxy-3-[4-(trifluoromethyl)phenyl]-1-propenyl}amino)propanoic acid;

(2S)-3-(4-{[5-ethyl-2-(4-fluorophenyl)-1,3-oxazol-4-yl]methoxy}phenyl)-2-{[(Z)-3-oxo-3-phenyl-1-(trifluoromethyl)-1-propenyl]amino}propanoic acid;

(2S)-3-{4-[(5-ethyl-2-phenyl-1,3-oxazol-4-yl)methoxy]phenyl}-2-({(Z)-1-methyl-3-oxo-3-[4-(trifluoromethyl)phenyl]-1-propenyl}amino)propanoic acid;

(2S)-3-(4-{[5-ethyl-2-(4-fluorophenyl)-1,3-oxazol-4-yl]methoxy}phenyl)-2-({(Z)-1-methyl-3-oxo-3-[4-(trifluoromethyl)phenyl]-1-propenyl}amino)propanoic acid;

(2S)-3-(4-{2-[5-ethyl-2-(4-fluorophenyl)-1,3-thiazol-4-yl]ethoxy}phenyl)-2-({(Z)-1-ethyl-3-oxo-3-[4-trifluoromethyl)phenyl]-1propenyl}amino)propanoic acid;

and pharmaceutically acceptable salts and solvates thereof.

12. A compound of claim 1 wherein said compound is a dual activator of hPPARγ and hPPARα.

13. A pharmaceutical composition comprising a therapeutically effective amount of a compound of claim 1.

14. A pharmaceutical composition of claim 13 further comprising a pharmaceutically acceptable diluent or carrier.

* * * * *